United States Patent
Cheng et al.

(10) Patent No.: US 11,701,062 B2
(45) Date of Patent: Jul. 18, 2023

(54) DETECTION OF NOISE SIGNALS IN CARDIAC SIGNALS

(71) Applicant: Medtronic, Inc., Minneapolis, MN (US)

(72) Inventors: Ya-Jian Cheng, Lino Lakes, MN (US); D'Anne E Kudlik, Saint Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 203 days.

(21) Appl. No.: 17/237,839

(22) Filed: Apr. 22, 2021

(65) Prior Publication Data

US 2021/0236063 A1 Aug. 5, 2021

Related U.S. Application Data

(62) Division of application No. 15/802,615, filed on Nov. 3, 2017, now Pat. No. 10,987,517.

(Continued)

(51) Int. Cl.
| | |
|---|---|
| *A61B 5/308* | (2021.01) |
| *A61B 5/00* | (2006.01) |
| *A61N 1/365* | (2006.01) |
| *A61N 1/37* | (2006.01) |
| *A61N 1/362* | (2006.01) |
| *A61B 5/25* | (2021.01) |

(Continued)

(52) U.S. Cl.
CPC .............. *A61B 5/7203* (2013.01); *A61B 5/25* (2021.01); *A61B 5/282* (2021.01); *A61B 5/287* (2021.01); *A61B 5/349* (2021.01); *A61B 5/35* (2021.01); *A61B 5/352* (2021.01); *A61B 5/686* (2013.01); *A61B 5/6823* (2013.01); *A61B 5/7264* (2013.01); *A61N 1/365* (2013.01); *A61N 1/3622* (2013.01); *A61N 1/371* (2013.01); *A61N 1/3704* (2013.01); *A61B 5/30* (2021.01); *A61B 5/366* (2021.01); *A61B 5/6801* (2013.01); *A61B 5/6852* (2013.01); *A61B 5/7217* (2013.01); *A61B 5/7278* (2013.01)

(58) Field of Classification Search
None
See application file for complete search history.

(56) References Cited

U.S. PATENT DOCUMENTS

| | | |
|---|---|---|
| 4,428,378 A | 1/1984 | Anderson et al. |
| 5,052,388 A | 10/1991 | Sivula et al. |

(Continued)

FOREIGN PATENT DOCUMENTS

| | | |
|---|---|---|
| CN | 102038497 A | 5/2011 |
| CN | 103857330 A | 6/2014 |

(Continued)

OTHER PUBLICATIONS

First Office Action and Search Report from counterpart Chinese Application No. 201880071871.9 dated Nov. 18, 2022, 10 pp.

(Continued)

*Primary Examiner* — Kennedy Schaetzle
(74) *Attorney, Agent, or Firm* — Shumaker & Sieffert, P.A.

(57) ABSTRACT

Medical device systems include processing circuitry configured to acquire sensed cardiac signals associated with cardiac activity of a heart of a patient, and to analyze the sensed cardiac signals to determine if a noise signal is present within the cardiac signals.

20 Claims, 20 Drawing Sheets

Related U.S. Application Data

(60) Provisional application No. 62/471,938, filed on Mar. 15, 2017.

(51) Int. Cl.

| | | |
|---|---|---|
| *A61B 5/35* | (2021.01) | |
| *A61B 5/282* | (2021.01) | |
| *A61B 5/287* | (2021.01) | |
| *A61B 5/349* | (2021.01) | |
| *A61B 5/352* | (2021.01) | |
| *A61B 5/30* | (2021.01) | |
| *A61B 5/366* | (2021.01) | |

(56) References Cited

U.S. PATENT DOCUMENTS

| | | | |
|---|---|---|---|
| 5,117,824 | A | 6/1992 | Keimel et al. |
| 6,980,675 | B2 | 12/2005 | Evron et al. |
| 7,286,866 | B2 | 10/2007 | Okerlund et al. |
| 7,308,297 | B2 | 12/2007 | Reddy et al. |
| 7,308,299 | B2 | 12/2007 | Burrell et al. |
| 7,321,677 | B2 | 1/2008 | Evron et al. |
| 7,346,381 | B2 | 3/2008 | Okerlund et al. |
| 7,454,248 | B2 | 11/2008 | Burrell et al. |
| 7,499,743 | B2 | 3/2009 | Vass et al. |
| 7,565,190 | B2 | 7/2009 | Okerlund et al. |
| 7,587,074 | B2 | 9/2009 | Zarkh et al. |
| 7,599,730 | B2 | 10/2009 | Hunter et al. |
| 7,613,500 | B2 | 11/2009 | Vass et al. |
| 7,676,264 | B1 | 3/2010 | Pillai et al. |
| 7,684,863 | B2 | 3/2010 | Parikh et al. |
| 7,742,629 | B2 | 6/2010 | Zarkh et al. |
| 7,747,047 | B2 | 6/2010 | Okerlund et al. |
| 7,778,685 | B2 | 8/2010 | Evron et al. |
| 7,778,686 | B2 | 8/2010 | Vass et al. |
| 7,813,785 | B2 | 10/2010 | Okerlund et al. |
| 7,996,063 | B2 | 8/2011 | Vass et al. |
| 8,060,185 | B2 | 11/2011 | Hunter et al. |
| 8,180,428 | B2 | 5/2012 | Kaiser et al. |
| 8,401,616 | B2 | 3/2013 | Verard et al. |
| 8,977,350 | B2 | 3/2015 | Sarkar et al. |
| 9,320,446 | B2 | 4/2016 | Gillberg et al. |
| 9,474,457 | B2 | 10/2016 | Ghosh et al. |
| 9,486,151 | B2 | 11/2016 | Ghosh et al. |
| 9,901,276 | B2 | 2/2018 | Sarkar |
| 9,936,890 | B2 | 4/2018 | Sarkar et al. |
| 10,987,517 | B2 | 4/2021 | Cheng et al. |
| 11,071,500 | B2 | 7/2021 | Cheng et al. |
| 2004/0049120 | A1 | 3/2004 | Cao et al. |
| 2005/0008210 | A1 | 1/2005 | Evron et al. |
| 2006/0074285 | A1 | 4/2006 | Zarkh et al. |
| 2008/0269813 | A1 | 10/2008 | Greenhut et al. |
| 2009/0099619 | A1 | 4/2009 | Lessmeier et al. |
| 2011/0066203 | A1 | 3/2011 | Rosenberg et al. |
| 2011/0112398 | A1 | 5/2011 | Zarkh et al. |
| 2011/0184297 | A1 | 7/2011 | Vitali et al. |
| 2011/0196247 | A1 | 8/2011 | Cao et al. |
| 2011/0319777 | A1 | 12/2011 | Mehrotra et al. |
| 2012/0029373 | A1 | 2/2012 | Stadler et al. |
| 2012/0238892 | A1* | 9/2012 | Sarkar ............... A61N 1/3621 600/516 |
| 2012/0283587 | A1 | 11/2012 | Gosh et al. |
| 2012/0284003 | A1 | 11/2012 | Gosh et al. |
| 2013/0116739 | A1 | 5/2013 | Brada et al. |
| 2014/0107507 | A1 | 4/2014 | Ghosh et al. |
| 2014/0249437 | A1 | 9/2014 | Zong et al. |
| 2014/0276928 | A1 | 9/2014 | Vanderpool et al. |
| 2014/0323882 | A1 | 10/2014 | Ghosh et al. |
| 2014/0323892 | A1 | 10/2014 | Ghosh et al. |
| 2014/0371832 | A1 | 12/2014 | Ghosh et al. |
| 2014/0371833 | A1 | 12/2014 | Ghosh et al. |
| 2015/0157231 | A1 | 6/2015 | Gillberg et al. |
| 2015/0157232 | A1 | 6/2015 | Gillberg et al. |
| 2015/0157865 | A1 | 6/2015 | Gillberg et al. |
| 2016/0022164 | A1 | 1/2016 | Brockway et al. |
| 2016/0030751 | A1 | 2/2016 | Ghosh et al. |
| 2016/0045737 | A1 | 2/2016 | Ghosh et al. |
| 2016/0045738 | A1 | 2/2016 | Ghosh et al. |
| 2016/0045744 | A1 | 2/2016 | Gillberg et al. |
| 2017/0273589 | A1 | 9/2017 | Sarkar et al. |
| 2018/0028083 | A1 | 2/2018 | Greenhut et al. |
| 2018/0028086 | A1 | 2/2018 | Cao et al. |
| 2018/0264258 | A1 | 9/2018 | Cheng et al. |
| 2020/0345309 | A1 | 11/2020 | Cheng et al. |

FOREIGN PATENT DOCUMENTS

| | | |
|---|---|---|
| WO | 03005900 A1 | 1/2003 |
| WO | 2013054242 A1 | 4/2013 |

OTHER PUBLICATIONS

U.S. Appl. No. 17/385,481, filed Jul. 26, 2021, by Cheng et al.

PCT/US2018/057989) PCT Notification of Transmittal of the International Search Report and the Written Opinion of the International Searching Authority, dated Feb. 2, 2019, 28 pages.

Ryu, et al., "Simultaneous Electrical and Mechanical Mapping Using 3d Cardiac Mapping System: Novel Approach for Optimal Cardiac Resynchronization Therapy," Journal of Cardiovascular Electrophysiology, Feb. 2010, vol. 21, No. 2, pp. 219-222. (4 pages).

Sperzel, et al., "Intraoperative Characterization of Interventricular Mechanical Dyssynchrony Using Electroanatomic Mapping System—A Feasibility Study," Journal of Interventional Cardiac Electrophysiology, published online Jun. 14, 2012, 35(2); (8 pages).

Sweeney, et al., "Analysis of Ventricular Activation Using Surface Electrocardiography to Predict Left Ventricular Reverse Volumetric Remolding During Cardiac Resynchronization Theraphy," Circulation, Journal of the American Heart Association, 2010:121:626-634, originally published online Jan. 25, 2010, (10 pages).

Van Deursen et al., "Vectrocardiography as a Tool for Easy Optimization of Cardiac Resynchronization Therapy in Canine Left Bundle Branch Block Hearts," Circulation Arrhythmia and Electrophysiology, 2012:5:544-552, originally published online Apr. 24, 2012, (10 pages).

Prosecution History from U.S. Appl. No. 15/802,615, dated Nov. 15, 2019 through Dec. 30, 2020, 100 pp.

Badilini et al., "Relationship Between 12-Lead ECG QT Discussion and 3D-ECG Repolarization Loop," Computers in Cardiology 1995 Vienna, Austria, Sep. 10-13, 1995, DOI:10.1109/CIC.1995.482782, pp. 785-788.

Communication pursuant to Article 94(3) EPC from counterpart European Application No. 18715846.4, dated Mar. 24, 2023, 7 pp.

Kemmelings et al., "Automatic QRS Detection during Body Surface Mapping of Ventricular Tachycardia," Proceedings of the Annual International Conference of the IEEE Engineering in Medicine and Biology Society: Paris, France, Oct. 29-Nov. 1, 1992, DOI:10.1109/IEMBS.1992.5761109, pp. 561-562.

\* cited by examiner

DETECTION OF NOISE SIGNALS IN CARDIAC SIGNALS

RELATED APPLICATION

This application is a divisional filing of U.S. patent application Ser. No. 15/802,615, filed 3 Nov. 2017, which claims the benefit of U.S. Provisional Patent Application No. 62/471,938, filed 15 Mar. 2017, the entire content of each of which is incorporated herein by reference.

TECHNICAL FIELD

The disclosure relates to medical systems and methods to detect noise signals in sensed cardiac signals.

BACKGROUND

Electrical signals that are sensed by monitoring the electrical activity associated with the heart of a patient, such as the heart of a human patient, may assist a user, such as a physician, in evaluating the condition of the patient and/or the efficacy of cardiac therapy, such as drug therapy or electrical stimulation therapy, that is being provided or has previously been provided to the patient. Monitoring of these electrical signals associated with the heart of a patient may be performed as part of a test, referred to as an electrocardiogram (ECG) test, which may be performed in order to evaluate whether or not a patient's heart is functioning properly, to detect certain types of problems with the patient's heart, and/or to help in the evaluation of various medical treatments, such as cardiac therapy, that the patient may be undergoing or is being considered as a treatment option for the patient. In other examples, monitoring of the electrical signals associated with the cardiac activity of the heart of a patient may be performed by an implantable medical device that has been implanted within the patient. The implantable medical device may be configured to simply monitor cardiac activity of the patient by sensing the cardiac electrical signals associated with cardiac activity of the patient. The implantable medical device may also be configured to monitor the cardiac signals of a patient as part of therapy treatment, such as cardiac pacing, that is being provided to the patient by the implantable medical device.

SUMMARY

The disclosure describes medical systems and methods for detection of noise signals, which may be referred to as a "low frequency noise signal," which may occur within one or more sensed cardiac signals associated with monitoring cardiac activity of a patient. The monitoring of electrical signals associated with the cardiac activity of the heart of a patient may be useful in evaluating a patient with respect to the physical state and health of the patient. Further, monitoring of the cardiac activity of the heart of a patient may be useful in order to determine what type of cardiac therapy, such as a drug therapy and/or an electrical stimulation therapy, may be beneficial to address a heart condition or other health condition of the patient, and/or to evaluate the efficacy of a therapy that is being or has been applied to the patient.

As further described below, one or more of the sensed cardiac signals may include a low frequency noise signal that corrupts the waveform of the sensed cardiac signal. When corrupted by noise signals, the analysis of the cardiac signals may become hindered or impossible, and in some instances, may result in a false-positive indication of a cardiac event, such as asystole, in a patient. For example, a low frequency noise signal may include a large voltage spike in the waveform of a sensed cardiac signal, the voltage spike in some examples extending over a time period in a range of a fraction of a second to one or more seconds. This voltage spike may corrupt a waveform of a cardiac signal being sensed, which may result in loss of the ability to properly analyze the waveform to determine the actual state of the cardiac activity that is occurring with respect to the patient who is being monitored. The devices, systems, methods, and techniques described herein allow for the analysis of a sensed cardiac signal to detect the presence of one or more noise signals occurring within the analyzed waveforms of one or more sensed cardiac signals.

In some examples, detection of the noise signal within a sensed cardiac signal comprises setting a first and second detection window superimposed onto a portion of a waveform representative of the sensed cardiac signal, determining an area-under-the-curve for a portion of the waveform falling with the second detection window based on a baseline voltage value calculated from the portion of the waveform that falls within the first detection window, and comparing the calculated values for the area-under-the-curve to a noise signal threshold value. A noise signal may be determined to exist within the sensed cardiac signal in response to a determination that the calculated value for the area-under-the-curve exceeds the noise signal threshold value.

In another example, detection of a noise signal within a sensed cardiac signal comprises generating a difference signal based on a waveform representative of the sensed cardiac signal, setting a first and second detection window superimposed onto a portion of the difference signal, determining a number of negative values or a percentage of negative values occurring at some sampling rate for the portion of the difference signal that falls within the second detection window, and comparing the determine number of negative values or the determined percentage of negative values to one or more threshold values. A noise signal may be determined to exist within the sensed cardiac signal in response to a determination that the calculated value for the number of negative values or the percentage of negative values falls outside a range of values bounded by the one or more threshold values.

The detection of a noise signal within a sensed cardiac signal allows the corrupted cardiac signal to be rejected as a valid indication of the actual cardiac activity of the heart of the patient, and thus may prevent improper diagnosis of the condition of the patient and may prevent false-positive indications of certain types of cardiac events, such as a false-positive indication of asystole in the patient being monitored. The detection of a noise signal may also allow the system sensing the cardiac activity to be reconfigured for example to stop using, either temperately or permanently, the particular sensing channel that includes the electrode or the electrodes providing the sensed signal on which the noise signal has been detected.

As an example, devices and system described herein may be configured to perform a method comprising receiving, by a processing circuitry, a cardiac signal generated in response to electrical activity of a heart of a patient, determining, by the processing circuitry, a baseline voltage value of the cardiac signal within a first detection window, the first window comprising a first time period extending from a sample time and for a predefined amount of time prior to the sample time, and determining, by the processing circuitry, a voltage level value for the cardiac signal within a second detection window, the second detection window comprising a second time period extending from the sample time and for a predefined amount of time following the sample time. The method may further comprise calculating, by the processing circuitry, a difference value between the voltage level value for the second detection window and the baseline voltage value, comparing, by the processing circuitry, the difference value to a noise signal threshold value, and determining, by the processing circuitry, that the cardiac signal includes a noise signal in response to a determination that the difference value exceeds the noise signal threshold value.

In another example, a medical device comprises processing circuitry configured to receive a cardiac signal generated in response to monitoring electrical activity of a heart of a patient using a plurality of electrodes, determine a baseline voltage value of the cardiac signal within a first detection window, the first window comprising a first time period extending from a sample time and for a predefined amount of time prior to the sample time, and determine a voltage level value for the cardiac signal within a second detection window, the second detection window comprising a second time period extending from the sample time and for a predefined amount of time following the sample time. The processing circuitry may further be configured to calculate a difference value between the voltage level value for the second detection window and the baseline voltage value, compare the difference value to a noise signal threshold value, and determine that the cardiac signal includes a noise signal in response to a determination that the difference value exceeds the noise signal threshold value.

Another example of devices and system described herein may be configured to perform a method comprising receiving, by a processing circuitry, a cardiac signal generated in response to electrical activity of a heart of a patient, and determining, by the processing circuitry, a difference signal from the cardiac signal, the difference signal comprising a set of voltage values determined by calculating a difference between the voltage value of the cardiac signal at time y(n) and the voltage value of the cardiac signal at time y(n−1), wherein y(n−1) is the time value at some predefined time prior to the time y(n). The method may further comprise setting, by the processing circuitry, a first detection window having a first time period extending from a sample time and for a predefined amount of time following the sample time and a second detection window having a second time period starting at the expiration of the first detection window and extending for a predefined amount of time following the expiration of the first detection window, determining, by the processing circuitry, a quantification value corresponding to a number of negative signs for the difference signal occurring within the second detection window, comparing, by the processing circuitry, the quantification value to one or more threshold values, and determining, by the processing circuitry, that the cardiac signal includes a noise signal in response to a determination that the quantification value exceeds one or more threshold values.

In another example, a medical device system comprises processing circuitry configured to receive a cardiac signal generated in response to monitoring electrical activity of a heart of a patient using a plurality of electrodes, determine a difference signal from the cardiac signal, the difference signal comprising a set of voltage values determined by calculating a difference between the voltage value of the cardiac signal at time y(n) and the voltage value of the cardiac signal at time y(n−1), wherein y(n−1) is the time value at some predefined time prior to the time y(n). The processing circuitry may further be configured to set a first detection window having a first time period extending from a sample time and for a predefined amount of time following the sample time and a second detection window having a second time period starting at the expiration of the first detection window and extending for a predefined amount of time following the expiration of the first detection window, determine a quantification value corresponding to a number of negative signs for the difference signal occurring within the second detection window, compare the quantification value to one or more threshold values, and determine that the cardiac signal includes a noise signal in response to a determination that the quantification value exceeds one or more threshold values. Other alternatives that may be used to calculate the quantification value may include determining a number of positive sample values, determining a number of non-negative sample values (e.g., a count of zero sample values plus positive sample values) or a number of non-positive sample values (e.g., a count of zero sample values plus negative sample values), representative of one or more sensed cardiac signals.

It should be understood that although the invention is described principally in the context of detecting one or more noise signals occurring within one or more waveforms, the invention is not limited to use in that context. The principles of the invention may be used to detect noise signal in other types of sensed signals associated with the sensing of a variety of physiological parameters associated with a patient, and/or to adapt medical devices configured for the monitoring of these parameters and/or for the delivery of therapy to a patient that performs one or more of these same functions.

BRIEF DESCRIPTION OF THE FIGURES

Throughout the specification, reference is made to the appended drawings, where like reference numerals designate like or similar elements.

DETAILED DESCRIPTION

Figure 1:
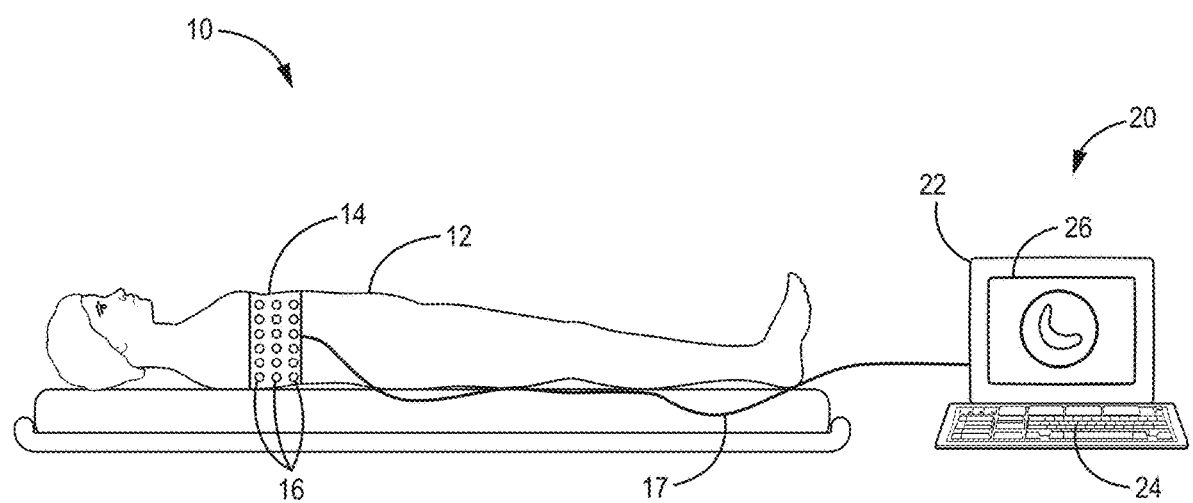
FIG. 1 is a conceptual drawing illustrating an example medical device system in conjunction with a patient according to various examples described in this disclosure.

The sensing of cardiac signals associated with the cardiac activity of the heart or other cardiac tissue of a patient may be performed by a variety of types of medical devices. In some examples, the devices and methods used to monitor the electrical signals associated with the cardiac activity of a patient are non-invasive. For example, a plurality of electrodes may be placed in contact with external portions of the patient, such as at various locations on the skin of the patient. The electrodes used to monitor cardiac activity in these non-invasive processes may be individually attached to the skin of the patient, for example using an adhesive, and electrically coupled to a monitoring device, such as a computing apparatus. In other examples, the electrodes used for the monitoring may be arranged as part of a vest, a belt, or located on a strap that is arranged to be worn by the patient in the area of the torso or the chest area of the patient. The electrodes are electrically coupled to an electronic device, such as an electrocardiograph, wherein the electrodes are configured to sense electrical signals associated with the electrical activity of the heart or other cardiac tissue of the patient, and to provide these sensed electrical signals to the electronic device for further processing and/or display of the electrical signals. The non-invasive devices and methods may be utilized on a temporary basis, for example to monitor a patient during a clinical visit, such as during a doctor's appointment, or for example for a predetermined period of time, for example for one day (twenty-four hours), or for a period of several days.

In some examples, the devices and methods used to monitor the electrical activity associated with the heart of a patient include use of one or more implantable medical devices (IMDs) that have been implanted within the patient. Various implantable medical devices that have been clinically implanted for therapeutically treating and/or monitoring one or more physiological conditions of a patient may be used to monitor the electrical activity of the heart of a patient. Such devices may be adapted to monitor and/or treat conditions or functions relating to heart, muscle, nerve, brain, stomach, endocrine organs or other organs and their related functions. The implantable medical devices may include electrodes for sensing cardiac signals that are located along a lead coupled to the implantable medical device. In some examples, a housing of the device itself may comprise one or more electrodes that may be used for sensing cardiac signals.

Advances in design and manufacture of miniaturized electronic and sensing devices have enabled development of implantable medical devices capable of therapeutic as well as diagnostic functions such as pacemakers, cardioverters, defibrillators, biochemical sensors, and pressure sensors, among others. Such devices may be associated with leads to position electrodes or sensors at a desired location or may be leadless, with the ability to wirelessly transmit data either to another device implanted in the patient or to another device located externally of the patient, or both. This transmitted data associated with the electrical activity of the heart of a patient may be used in a manner similar to that described above with respect to the electrical signals derived using the non-invasive devices. The implantable medical devices may be implanted within a patient on a temporary basis, for example during a trial period used for diagnosis of a patient's condition, and/or to determine the efficacy of the device for treatment of the patient. The implantable medical device may be implanted for use on a more permanent basis, which may extend for a period of months or years.

Regardless of which type or types of devices are used, when sensing a cardiac signal, a noise signal, which may be referred to as an ECG artifact, may appear in a waveform representative of a sensed cardiac signal. The ECG artifact or noise signal may be referred to a "low frequency noise signal" because the time duration of the signal may extend over a portion of a normal timeframe for a cardiac cycle of the heart, or may extend over a time span that would include a time span were multiple cardiac cycles may be expected to have occurred. This type of noise signal may be observed in a cardiac signal sensed using both subcutaneous and cutaneous monitoring devices. In some instances, a temporary and slight contact problem between at least one of the electrodes of the device being used to sense the cardiac signals (e.g., a particular sensing channel), and the tissue where the electrode is located causes the low frequency noise signal (e.g., a baseline drift of the voltage level of the sensed signal).

The presence of a noise signal in a sensed cardiac signal may cause a R-wave sensing algorithm being used to analyze the sensed cardiac signal to wrongly detect the noise signal as an R-wave. The noise signal may also cause the R-wave sensing algorithm to then fail to sense the following two or three R-waves because the noise signal may be much bigger in amplitude than the subsequent R-waves. These types of improper sensing of R-waves may lead to improper analysis of the actual cardiac activity occurring with respect to the patient being monitored. For example, the noise signal may potentially trigger a false-positive indication of a cardiac event, such as asystole, that is not actually occurring in the patient. Such false-positive indications could lead to improper implant of pacemakers or application of stimulation therapy to the patient, and/or other negative consequences such as sending false alerts to nurses and other medical personnel response for the care of the patient being monitored, and thus distracting and/or annoying them. Low pass filtering of the cardiac signal will generally not help solve these problems because filtering of the cardiac signals that include these types of noise signals may generate a flat line at the portion of the waveform where the low frequency noise occurs, wherein the flat line may also trigger a false-positive indication of an asystole detection.

Therefore, it is desirable to detect the presence of these noise signals in monitored cardiac signals so that these noise signals, or at least the portions of the cardiac signal that includes the detected noise signal, may be rejected for use in the analysis of the actual cardiac activity associated with the patient being monitored. The medical device systems, methods and techniques described herein provide solutions to these problems by utilizing various techniques to analyze the waveforms representative of a sensed cardiac signal, and to detect the occurrence of a noise signal within the analyzed waveform. In some examples, the analysis includes setting one or more detection windows that are superimposed over some portion or portions of the waveform being analyzed, and calculating an area-under-the-curve value associated with one or more of the detection windows. The calculated area-under-the-curve value may then be compared to a noise signal threshold value to determine whether the analyzed portion or portions of the waveform include a noise signal. In some examples, a difference signal, sometimes referred to as a "finite difference signal," may be calculated based on the waveform representative of a sensed cardiac signal. The analysis of the difference signal includes setting one or more detection windows that are superimposed over some portion or portions of the difference signal being analyzed, and calculating a number, a percentage and/or a ratio of values, for the difference signal meeting a particular criterion or set of criteria and that fall within the one or more detection windows. The calculated number, percentage, or ratio of values meeting a particular criterion or set of criteria that fall within a given detection window may be referred to as a quantification value. Once a quantification value for the one or more detection windows has been calculated, the quantification value may be compared to one or more threshold values to determine if the analyzed portion of the difference signal, and thus the corresponding portion of the waveform representing a sensed cardiac signal, includes a noise signal.

A detection of a noise signal in an analyzed cardiac signal may further result in the generation of an alarm output signal by the device performing the analysis. In some examples, the device performing the analysis of the cardiac signals is a computing apparatus that may be coupled to the electrodes sensing the cardiac signals. In some examples, the device performing the analysis of the cardiac signal is an implanted medical device that may or may not be coupled to the electrodes sensing the cardiac signals. When a noise signal has been detected in one or more of the cardiac signals being analyzed, the computing apparatus or implantable medical device may be configured to provide an output, such as a graphical display that is displayed on a display device, the graphical display indicative of the detection of the noise signal. In some examples, the alarm output signal is output from the device performing the noise detection analysis, such as an implanted IMD, to an external device, such as a computing apparatus or an IMD programming device. The external device may include an output device, such as a graphical display, that may provide an indication to a user, such as a physician, regarding the detection the noise signal.

The detection of a noise signal may include an indication, such as a graphical indication, indicative of which sensing channel or sensing devices, for example which electrode pair was being used to sense the cardiac signal where the noise signal was detected. In various examples, the system performing the analysis of the cardiac signal where the noise signal was detected may reconfigure the system to no longer utilize the sensing channel or sensing devices, either on a temporary or a permanent basis, having incurred the noise signal. In various examples, the system performing the analysis of the cardiac signal where a noise signal was detected may also be configured to provide therapy to the patient, such as electrical stimulation therapy, using one or more of the same electrodes used for sensing the cardiac signal. These systems may, based on the detection of the noise signal on a particular sensing channel, reconfigure one or more therapy parameters used to provide or to potentially provide therapy to the patient to not utilize one or more of these same electrodes associated with the noise signal for the delivery of therapy to the patient.

In some examples, the analysis of the sensed cardiac signal or signals may be performed in real-time, e.g., analysis is performed as the cardiac signal or signals is/are received from the sensing electrodes. However, the timeframe between when the cardiac signal or signals are sensed and when the analysis of the cardiac signals is performed is not limited to any particular time frame. In some examples, the data associated with a sensed cardiac signal or signals may be stored, and later retrieved to perform an analysis of the data to detect the presence of any noise signals that may have occurred within the sensed cardiac signal or signals. Various additional details and examples of the systems and techniques for detection of noise signals, and for controlling medical device systems based on the detection of a noise signal within a sensed cardiac signal, are illustrated and described below with respect to FIGS. 1-14.

FIG. 1 is a conceptual drawing illustrating an example medical device system 10 in conjunction with a patient 12 according to various examples described in this disclosure. FIG. 1 shows exemplary system 10 including an electrode apparatus 14 and a computing apparatus 20 including a display device 22. The electrode apparatus 14 as shown includes a plurality of electrodes 16 incorporated, or included, within a band wrapped around the chest, or torso, of the patient 12. The electrode apparatus 14 is operatively coupled to the computing apparatus 20 (e.g., through one or more wired electrical connections 17, or wirelessly, etc.) to provide electrical signals from the electrodes 16 to the computing apparatus 20 for further processing, display, analysis, and/or evaluation of the signals. Exemplary electrode apparatus 14 may be described in U.S. Pat. No. 9,320,446 entitled "Bioelectric Sensor Device and Methods" and issued on Apr. 26, 2016, which is incorporated herein by reference in its entirety. Additional examples of electrode apparatus 14 will be described in more detail in reference to FIG. 2 and FIG. 3 of this disclosure.

As shown in FIG. 1, the computing apparatus 20 including display device 22 may be configured to analyze data, such as electrical signals (e.g., electrocardiogram data) and/or other cardiac information representative of at least one of mechanical cardiac functionality and electrical cardiac functionality. Cardiac information may include for example electrical heterogeneity information or electrical dyssynchrony information, surrogate electrical activation information or data, etc. that is generated using electrical signals gathered, monitored, or collected, using the electrode apparatus 14. In at least one example, the computing apparatus 20 may be a server, a personal computer, a laptop computer, a tablet computer, or an electronic device configured to receive the electrical signals from electrode apparatus 14, and to process and/or display information related to the received signals. In addition, the computing apparatus 20 may be configured to receive inputs from an input apparatus 24, such as a computer keyboard, and to transmit outputs, such as outputs to control a graphical display, such as the display device 22. Display device 22 may comprise any type of device, such as a computer monitor or plasma display, arranged to visually display graphical information viewable by a user, such as a patient or a physician. Further, the computing apparatus 20 may include data storage circuitry that may store and allow access to processing programs or routines and/or one or more other types of data, e.g., for driving a graphical user interface configured to display information related to the sensed cardiac signals, and thereby assist a user in evaluating cardiac signals to determine for example various parameters associated with the condition of the patient being monitored, or other data, such as a pacing location (e.g., the location of an implantable electrode used for pacing, the location of pacing therapy delivered by a particular pacing vector, etc.).

The computing apparatus 20 may be operatively coupled to the input apparatus 24 and the display device 22 to, e.g., transmit data to and from each of the input apparatus 24 and the display device 22. For example, the computing apparatus 20 may be electrically coupled to each of the input apparatus 24 and the display device 22 using, e.g., analog electrical connections, digital electrical connections, wireless connections, bus-based connections, network-based connections, internet-based connections, etc. As described further herein, a user may provide inputs to the input apparatus 24 and/or to the display device 22 (e.g., wherein the display device comprises a touch screen), to manipulate or modify and/or otherwise control the one or more graphical depictions displayed on the display device 22, and to view and/or select one or more pieces of information related to the monitoring of the cardiac signals. Inputs provided to computing apparatus 20 may also be used to control the processes being performed as part of the monitoring of the electrical activity associated with cardiac activity of patient 12.

Although as depicted in FIG. 1 the input apparatus 24 is a keyboard, it would be understood that the input apparatus 24 may include any apparatus capable of providing inputs to the computing apparatus 20 to perform the functionality, methods, and/or logic described herein. For example, the input apparatus 24 may include a computer mouse, a trackball device, a touchscreen (e.g., capacitive touchscreen, a resistive touchscreen, a multi-touch touchscreen, etc.), etc. Likewise, the display device 22 may include any apparatus, such as graphical user interface 26, capable of displaying information to a user including cardiac information, textual instructions, graphical depictions of electrical activation information, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display device 22 may include a liquid crystal display, an organic light-emitting diode screen, a touchscreen, a cathode ray tube display, etc.

The processing programs or routines stored and/or executed by the computing apparatus 20 may include programs or routines for computational mathematics, matrix mathematics, dispersion determinations (e.g. standard deviations, variances, ranges, interquartile ranges, mean absolute differences, average absolute deviations, etc.), filtering algorithms, maximum value determinations, minimum value determinations, threshold determinations, threshold values, moving windowing algorithms, calculating a value for the areas-under-the-curve of a portion of a cardiac signal, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more exemplary methods and/or processes described herein. Data stored and/or used by the computing apparatus 20 may include, for example, electrical signal/waveform data from the electrode apparatus 14, dispersions signals, windowed dispersions signals, parts or portions of various signals, electrical activation times from the electrode apparatus 14, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, cardiac information, etc.), or any other data that may be necessary for carrying out the one and/or more processes or methods described herein.

In one or more examples, the exemplary systems, methods, and interfaces of system 10 may be implemented using one or more computer programs executed on one or more programmable computers, such as computers that includes one or more processors and/or processing circuitry configured to provide processing capabilities, data storage (e.g., volatile or non-volatile memory and/or storage elements), and to receive inputs from, provide output to, and otherwise interface with one or more input devices and output devices. Program code and/or logic described herein may be applied to input data to perform functionality described herein, and to generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in one or more of the exemplary systems, methods, and/or interfaces may be configured to implement by logic (e.g., object code) encoded in one or more non-transitory media that includes code for execution and, when executed by a processor, is operable to perform operations such as the methods, processes, and/or functionality described herein.

The computing apparatus 20 may be, for example, any fixed or mobile computer system (e.g., a controller, a microcontroller, a personal computer, minicomputer, tablet computer, etc.). The exact configuration of the computing apparatus 20 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable medium such as a disk or tape, etc.) containing digital bits (e.g., encoded in binary, trinary, etc.) that may be readable and/or writeable by computing apparatus 20 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

Electrical activation times of the patient's heart, and other parameters associated with and/or derived from sensed cardiac signals, may be useful to evaluate a patient's cardiac condition and/or cardiac therapy being delivered to a patient. Surrogate electrical activation information or data of one or more regions of a patient's heart may be monitored, or determined, using electrode apparatus 14 as shown in FIG. 1. The exemplary electrode apparatus 14 may be configured to measure body-surface potentials of a patient 12 and, more particularly, torso-surface potentials of a patient 12. In certain instances, a temporary and slight contact problem between one or more of the electrodes 16 relative to patient 12 may generate what may be referred to as a low frequency noise signal on the signal being provided by the affected electrode or electrodes. This low frequency noise signal may result in a baseline drift of the voltage value of the sensed signal, which may for example cause an R-wave sensing algorithm to wrongly detect the noise signal as a R-wave, and even worse, may then cause the R-wave sensing algorithm to fail to sense the following two or three R-waves because the noise is much bigger than the subsequent R-waves. These missteps in the detection of actual R-waves associated with cardiac signals may lead to improper conclusions and/or false-positive indication of the actual cardiac activity and/or the occurrence of a cardiac event associated with the patient being monitored.

Therefore, it is desirable to detect a low frequency noise signal occurring within a waveform of a sensed cardiac signal so that these types of signals can be rejected, and therefore do not result in improper detection and/or counting of sensed R-waves within the cardiac signal, and to prevent false-positive indications of cardiac events, such as asystole in a patient, that might be improperly detected as a result of the noise signal. Low pass filtering of these noise signals may not be useful for these low frequency noise signals because this type of filtering may, for example, generate a flat line in the portion of the signal were the low frequency noise is occurring, which may generate a false indication of asystole in the patient being monitored.

System 10 is arranged to provide techniques for analyzing the cardiac signal to determine if the analyzed signals include a low frequency noise signals, and by detecting the presence of these low frequency noise signals, allows rejection of the portion or portions of the cardiac signal(s) that include the detected low frequency noise signal or signals. Rejection of a signal or signals that are determined to include a low frequency noise signal may prevent miscounting of R-waves in the monitored signals, and may prevent the false-positive indication of a cardiac event, such as asystole, occurring for a monitored patient. Detection of the noise signal or signals may also allow the system to be reconfigured to stop using an affected lead and/or electrode pair providing the cardiac signal that includes the detected noise signal for the further monitoring of the patient. Detection of the noise signal or signals and may also allow the system to be reconfigured to stop using or to not use an affected lead and/or electrode pair providing the cardiac signal that included the detected noise signal for the purpose of providing therapy, such as electrical stimulation therapy, to the patient.

In one example, processing circuitry of computing apparatus 20 is configured to receive input signals including one or more cardiac signals generated in response to electrical activity of the heart of patient 12, as sensed by electrodes 16 of the electrode apparatus 14. The processing circuitry may perform an analysis on one, some, or all of the one or more cardiac signals to determine if the analyzed cardiac signal or signals include a noise signal. Using a pre-determined sampling rate or a triggering event sensed in the cardiac signal (e.g., detection of a R-wave), the processing circuitry of computing apparatus 20 may be configured to perform processing on a given cardiac signal as follows. The processing circuitry sets a first detection window that includes a portion of the cardiac signal to by analyzed that was sensed during a predefined time period extending from the sample time and for a predefined amount of time prior to the sample time. A first amplitude value, in some examples is a baseline voltage, is calculated for the cardiac signal based on the sensed voltage levels of the cardiac signal during the first detection window. A second detection window is set, the second detection window including a portion of the cardiac signal to be analyzed that was sensed during a time period extending from the sample time and for a pre-defined amount of time following the sample time. A second voltage value is calculated for the cardiac signal based on the sensed voltage levels of the cardiac signal during the second detection window. The second voltage value may be based on calculating an area-under-the-curve for the portion of the waveform that falls within the second detection window and that is above the baseline amplitude value calculated for the first detection window.

The processing circuitry may then calculate a difference value between the first voltage level (baseline voltage level) and the second voltage value (e.g., using the formula: difference value=second voltage value−baseline voltage level). The processing circuitry of computing apparatus 20 may then compare the calculated difference value associated with the sample time of the cardiac signal being analyzed to a noise signal threshold value. The noise signal threshold value may be a programmable value that is programmed into computing apparatus 20, for example by a user (physician, not shown in FIG. 1), and may be stored in a memory within or coupled to the computing apparatus 20. The processing circuitry may determine that the portion of the cardiac signal being analyzed at the sample time represents a noise signal in response to a determination that the calculated difference value associated with the sample time exceeds the noise signal threshold value. In some examples, the processing circuitry is configured to provide as an output, such as an output that is displayed visually on display device 22, indicating that a noise signal associated with one of the cardiac signals being analyzed was detected. The output may further indicate which electrode or electrodes of electrodes 16 (e.g., which sensing channel) provided the signal including the detected noise signal, and the time (e.g., the sample time) associated with the detected noise signal. In various examples, the output may include a graphical depiction of the cardiac signal that included the detected noise signal, along with a graphical depiction of the first and second detection windows superimposed over the cardiac signal, and/or other information, such as numerical and/or text information that is associated with the detected noise signal, such as a value for an area-under-the curve associated with the detected noise signal.

In examples using the first detection window and the second detection window, the processing circuitry may be configured to utilize a plurality of sample times, taken along a progressive series of sample times, so that the first detection window and the second detection window operate as a moving or sliding set of detection windows that may be set at each of the sample times in a manner as described above for the first and second detection windows. The processing circuitry may then perform the analysis for each of the sets of detection windows set at each of the sample times to determine a difference value as described above for each of the sample times based on the calculated values for the first and second detection windows associated with each sample time. Each of these determined difference values may be compared to the noise signal threshold value to determine if the portion of the waveform being analyzed and associated with the particular sample time includes a noise signal. In various examples, the processing circuitry may record information associated with detection of a noise signal, such as date, time, and sensing channel/electrode information. Additional details and examples using this technique for detection of a noise signal that may be present on one or more cardiac signals being analyzed by system 10 is illustrated and described with respect to FIG. 11B.

Referring again to FIG. 1, in another example, the processing circuitry of computing apparatus 20 may be configured to detect a noise signal in one or more cardiac signals using a calculation based on determining an area under a portion of the waveform representative of a sensed cardiac signal. In this example, the processing circuitry of computing apparatus 20 may be configured to receive input signals including one or more cardiac signals generated in response to electrical activity of the heart of patient 12, as sensed by electrodes 16 of the electrode apparatus 14. The processing circuitry may perform analysis on one, some, or all of the one or more cardiac signals individually to determine if any of the analyzed cardiac signals include a noise signal. For each cardiac signal to be analyzed, the processing circuitry may determine the position of a R-wave within the sensed cardiac signal. Based on the position of the sensed R-wave, the processing circuitry sets a first detection window beginning at the time of the detected R-wave, and extending over a period of time following the R-wave. The processing circuitry then sets a second detection window having a start time at the time of expiration of the first detection window, and extending over a pre-defined time span following the start time of the second detection window.

After setting the first and second detection windows associated with a sensed R-wave, the processing circuitry then determines an area-under-the-curve of the cardiac signal being analyzed that falls within the second detection window. The determined area-under-the-curve associated with the second detection window in some examples includes the area of the cardiac signal having values that exceed a baseline amplitude value calculated based on the voltage values falling within the first detection window, or based on some pre-defined baseline voltage value. The determined area-under-the-curve associated with the second detection window is then compared to a noise signal threshold value. The noise signal threshold value may be a programmable value that is programmed into computing apparatus 20, for example by a user (physician, not shown in FIG. 1), and may be stored in a memory within or coupled to the computing apparatus 20. The processing circuitry may then determine that the cardiac signal being analyzed includes a noise signal in response to a determination by the processing circuitry that the determined area-under-the-curve associated with the second detection window exceeds the noise signal threshold value.

In the examples using the above described technique for determined an area-under-the-curve associated with the second detection window set following the detection of a sensed R-wave, the processing circuitry may be configured to set a detection window and perform the area-under-the-curve calculation for one or more R-waves detected within a cardiac signal being analyzed. In some examples, the processing circuitry is configured to set the first and second detection windows for each R-wave detected in a cardiac signal being analyzed, and to perform analysis based on the voltage values falling with the second detection window as described above for each of the sets of detection windows. In other examples, the processing circuitry may be configured to set detection windows only following of detection of some number (N) of consecutive sensed R-waves, for example but not limited to every third, every fifth, or every tenth sensed R-wave. In some examples, the time spans of the first and/or the second detection windows associated with a particular sensed R-wave may extend into a time period when a subsequent R-wave of the cardiac signal may be detected, and thus may overlap, at least to some extent, with one or more of the detection windows associated with previously and/or subsequently occurring R-waves within that same cardiac signal.

In some examples, by setting detection windows associated with each detected R-wave, or with some N number of detected R-waves within a cardiac signal, the processing circuitry may perform a series of area-under-the-curve calculations, utilizing a plurality of detection windows, so that the detection windows operate as a moving or sliding set of time windows, each set of windows may be set based on the detection of a sensed R-wave within the cardiac signal as described above. The processing circuitry may then perform the analysis of the cardiac signal to determine a difference value as described above for each of the sets of detection windows based on the calculated areas under the waveforms representative of the cardiac signal falling within each of the second detection windows. In various examples, the processing circuitry may record information associated with detection of a noise signal, such as date, time, and/or sensing channel information. The detection of the noise signals may be further used by system 10 to reject false-positive indications of cardiac events, and/or may be displayed for example on display device 22 using for example any of the techniques described throughout this disclosure. This information related to the detection of noise signals may also be stored for later review and/or further analysis by a user, such as a physician. Additional details and examples of this technique for detection of a noise signal present on one or more cardiac signals using the area-under-the-curve calculation and sensed R-waves is further illustrated and described with respect to FIG. 11C.

Referring again to FIG. 1, in another example the processing circuitry of computing apparatus 20 may be configured to detect a noise signal in one or more cardiac signals using a calculation based on a count, a percentage, or a ratio calculation of a quantification value, for example a number of negative sample values, which may also be referred to as "negative signs," representative of a waveform of a sensed cardiac signal within a detection window. In this example, the processing circuitry may be configured to receive input signals including one or more cardiac signals generated in response to electrical activity of the heart of patient 12, as sensed by electrodes 16 of the electrode apparatus 14. The processing circuitry may perform analysis on one, some, or all of the one or more cardiac signals individually to determine if any of the analyzed cardiac signals include a noise signal. For each cardiac signal to be analyzed, the processing circuitry may generate a difference signal based on a sensed cardiac signal that is to be analyzed. The difference signal may comprise a set of values determined by calculating a difference between the value of the cardiac signal at time "y(n)" and the value of the cardiac signal at time "y(n−1)," wherein y(n−1) is the time value at some predefined time prior to the time y(n). The processing circuitry may also detect the position of R-waves within the difference signal representative of the cardiac signal being analyzed. For a given detected R-wave, the processing circuitry may be configured to set a detection window extending over a period of time following the R-wave and superimposed over the difference signal, the detection window having a start time following a blanking period following the position of the R-wave, and the detection window extending over a pre-defined time span following the start time, and ending at the expiration of the pre-defined time span.

Using the portion of the difference signal that corresponds to the portion of the cardiac signal that falls within the detection window, the processing circuitry then determines a quantification value, for example a number of negative sample values (e.g., negative signs) occurring in the difference signal falling within the detection window. For example, a negative sign may exist for a peak in the difference signal where the value of the difference signal is negative, e.g., less than zero, at some predefined sample time interval. Although described herein as determining a count of the number of negative sample values, other alternatives that may be used to calculate the quantification value may include determining a number of positive sample values, determining a number of non-negative sample values (e.g., a count of zero sample values plus positive sample values) or determining a number of non-positive sample values (e.g., a count of zero sample values plus negative sample values). The determined number of values, whether negative, non-negative, positive, or non-positive, may be used to determine a ratio or percentage value corresponding to the number of these values counted relative to a total number of samples taken.

The determined number of negative signs for the difference signal falling within the detection window, or for example a percentage of or for a ratio calculated for the quantization value associated with the sample times taken within the detection window, is then compared to one or more threshold values. The threshold values may be programmable values that are programmed into computing apparatus 20, for example by a user (physician, not shown in FIG. 1), and stored in a memory within or coupled to the computing apparatus. The processing circuitry may then determine that the cardiac signal being analyzed includes a noise signal in response to a determination by the processing circuitry that the number of negative signs, the percentage, or the ratio of negative signs calculated as the quantization value for the portion of the difference signal falling within the detection window imposed over the difference signal exceeds one or more threshold values. In some examples, the analyzed portion of the cardiac signal is determined to include a noise signal if the percentage of negative signs sampled at the sample times falling with the detection window exceeds a maximum percentage threshold value, or if the percentage of negative signs sampled at the sample times falling with the detection window is less than a minimum percentage threshold value. In other words, if the percentage of negative signs sampled at the sample times falling within the detection window does not fall within a range that is above the minimum threshold value and below the maximum threshold value, the portion of the signal occurring within the detection window is considered to be a noise signal.

The detection of the noise signal using this difference signal and based on the determination of the number, percentage, or ratio of samples falling within a detection window used to determine the quantization value associated with the detection window may be further used by system 10 to reject that portion of the cardiac signal, and/or to prevent a false-positive indication of cardiac events, and/or may be displayed for example on display device 22 using any of the techniques described throughout this disclosure. This information related to the detection of noise signals may also be stored for later review and/or further analysis by a user, such as a physician. Additional details and examples of this technique for detection of a noise signal present on one or more cardiac signals being analyzed by system 10 is further illustrated and described with respect to FIG. 11D.

Figure 2:
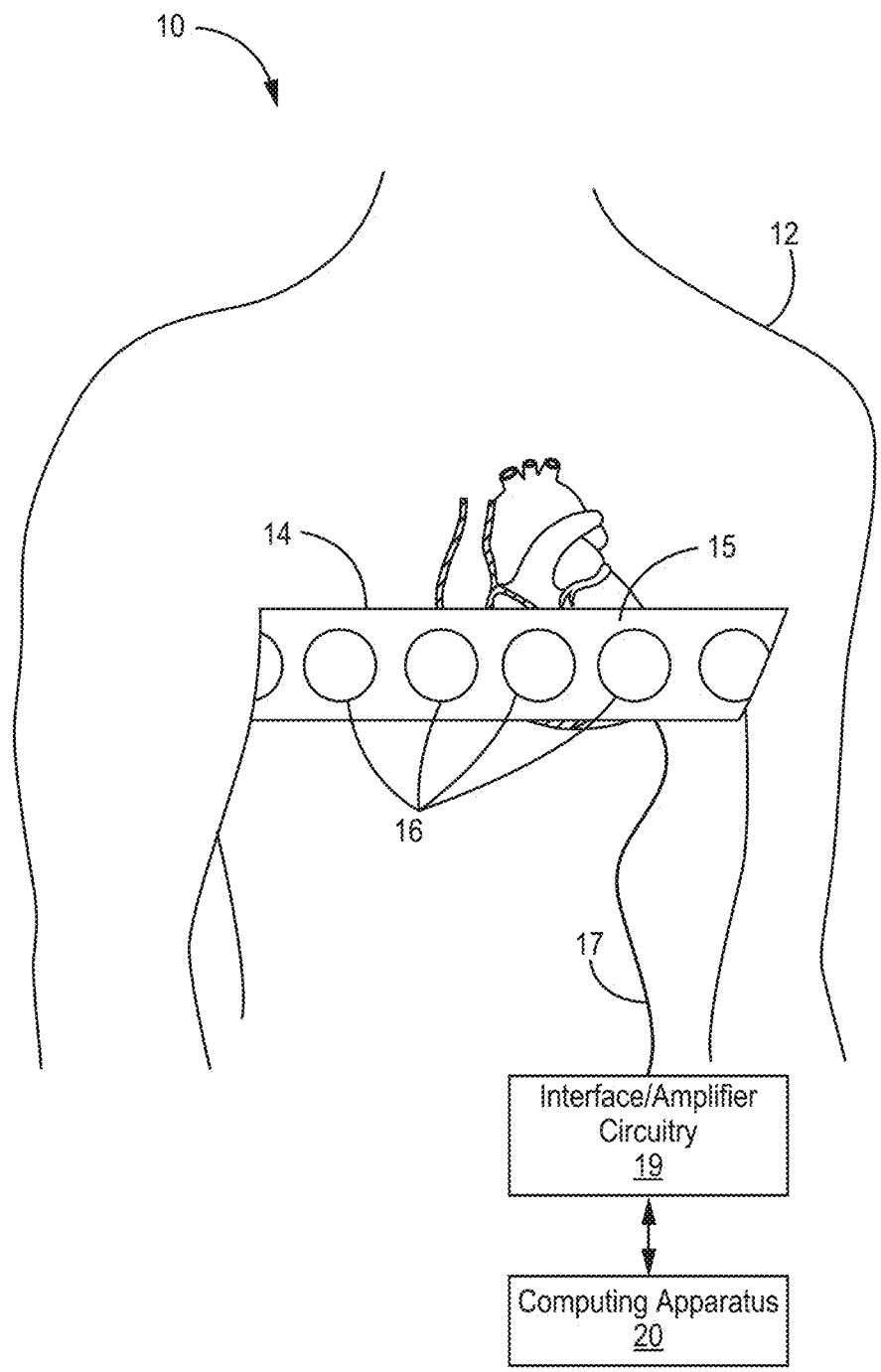
FIG. 2 is a conceptual drawing illustrating another example of the medical device system in conjunction with a patient according to various examples described in this disclosure.

FIG. 2 is a conceptual drawing illustrating another example of the medical device system 10 in conjunction with a patient 12 according to various examples described in this disclosure. As shown in FIG. 2, the exemplary electrode apparatus 14 may include a set or array of electrodes 16, a strap 15, and having the electrode apparatus 14 coupled to an interface/amplifier circuitry 19 that is coupled to computing apparatus 20. The electrodes 16 may be attached, or coupled, to the strap 15, and the strap 15 may be configured to be wrapped around the torso of a patient 12 such that the electrodes 16 surround and/or are placed in close proximity to some portion of the patient's heart. As further illustrated in FIG. 2, the electrodes 16 may be positioned around the circumference of a patient 12, including the posterior, lateral, posterolateral, anterolateral, and anterior locations of the torso of a patient 12. Electrode apparatus 14 may be configured to position electrodes 16 in physical contact with the skin of the patient when electrode apparatus 14 is positioned on patient 12.

Further, the electrodes 16 may be electrically connected to interface/amplifier circuitry 19 via wired connection 17. The interface/amplifier circuitry 19 may be configured to amplify the signals from the electrodes 16, and provide the amplified signals to the computing apparatus 20. Interface/amplifier circuitry 19 may provide other features related to the signals provided by electrodes 16, such as providing input/impedance buffering of the received signals, and/or other processing, such as analog-to-digital conversion of the received signals. Examples of system 10 as shown in FIG. 2 may use a wireless connection to transmit the signals sensed by electrodes 16 to the interface/amplifier circuitry 19 and, in turn, to the computing apparatus 20, e.g., as channels of data. For example, the interface/amplifier circuitry 19 may be electrically coupled to computing apparatus 20 using, e.g., analog electrical connections, digital electrical connections, wireless connections, bus-based connections, network-based connections, internet-based connections, etc.

Although in the example of system 10 as shown FIG. 2 the electrode apparatus 14 includes a strap 15, in other examples any of a variety of mechanisms, e.g., tape or adhesives, may be employed to aid in the spacing and placement of electrodes 16. In some examples, the strap 15 may include an elastic band, strip of tape, or cloth. In other examples, the electrodes 16 may be placed individually on the torso of a patient 12. Further, in other examples electrodes 16 (e.g., arranged in an array) may be part of, or located within, patches, vests, and/or other manners of securing the electrodes 16 to the torso of the patient 12.

The electrodes 16 may be configured to surround the heart of the patient 12 and record, or monitor, the electrical signals associated with the depolarization and repolarization of the heart after the signals have propagated through the torso of a patient 12. Each of the electrodes 16 may be used in a unipolar configuration to sense the torso-surface potentials that reflect the cardiac signals. The interface/amplifier circuitry 19 may also be coupled to a return or indifferent electrode (not shown) that may be used in combination with each electrode 16 for unipolar sensing. In some examples, there may be about twelve to about fifty electrodes 16 spatially distributed around the torso of patient. Other configurations may have more or fewer electrodes 16.

The computing apparatus 20 may record and analyze the torso-surface potential signals sensed by electrodes 16 and amplified/conditioned by the interface/amplifier circuitry 19. As described above, the processing circuitry of computing apparatus 20 may be configured to detect a noise signal in one or more cardiac signals sensed through electrodes 16 using any of the techniques described throughout this disclosure for analyzing the cardiac signals to detect noise signals occurring within the sensed cardiac signals. In the example illustrated in FIG. 2, the processing circuitry of computing apparatus 20 may be configured to receive input signals including one or more cardiac signals generated in response to electrical activity of the heart of patient 12, as sensed by electrodes 16 of the electrode apparatus 14. The processing circuitry may perform analysis on one, some, or all of the one or more cardiac signals individually to determine if any of the analyzed cardiac signals include a noise signal. The computing apparatus 20 may be configured to analyze the signals from the electrodes 16 to provide surrogate electrical activation information or data such as surrogate cardiac electrical activation times, e.g., representative of actual, or local, electrical activation times of one or more regions of the patient's heart.

For example, electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart. In one or more embodiments, measurement of activation times can be performed by measuring the period of time between an onset of cardiac depolarization (e.g., onset of QRS complex) and the next onset of cardiac depolarization. In one or more examples, measurement of activation times can be performed by measuring the period of time between an onset of cardiac depolarization (e.g., onset of QRS complex) and conclusion of cardiac repolarization (e.g., offset of QRS complex). In one or more embodiments, measurement of activation times can be performed by picking an appropriate fiducial point (e.g., peak values, minimum values, minimum slopes, maximum slopes, zero crossings, threshold crossings, etc. of a near or far-field EGM) and measuring time between fiducial points (e.g., within the electrical activity).

Additionally, the computing apparatus 20 may be configured to provide graphical user interfaces depicting the surrogate electrical activation times obtained using the electrode apparatus 14. Exemplary systems, methods, and/or interfaces may noninvasively use the electrical information collected using the electrode apparatus 14 to detect noise signals that may be present on the signals received from electrodes 16 in conjunction with monitoring cardiac activity associated with patient 12. Detection of the noise signal or signals using the example system 10 as illustrated in FIG. 2 may be used to reject signals determined to include noise signals, and to prevent indications of false-positives of cardiac events, such as asystole, associated with the monitoring of a patient. Computing apparatus 20 as shown in FIG. 2 may be configured to perform any of the functions, and to provide any of the features, including display of graphical information associated with sensed cardiac signals and the detection of noise signals, as described throughout this disclosure.

Figure 3:
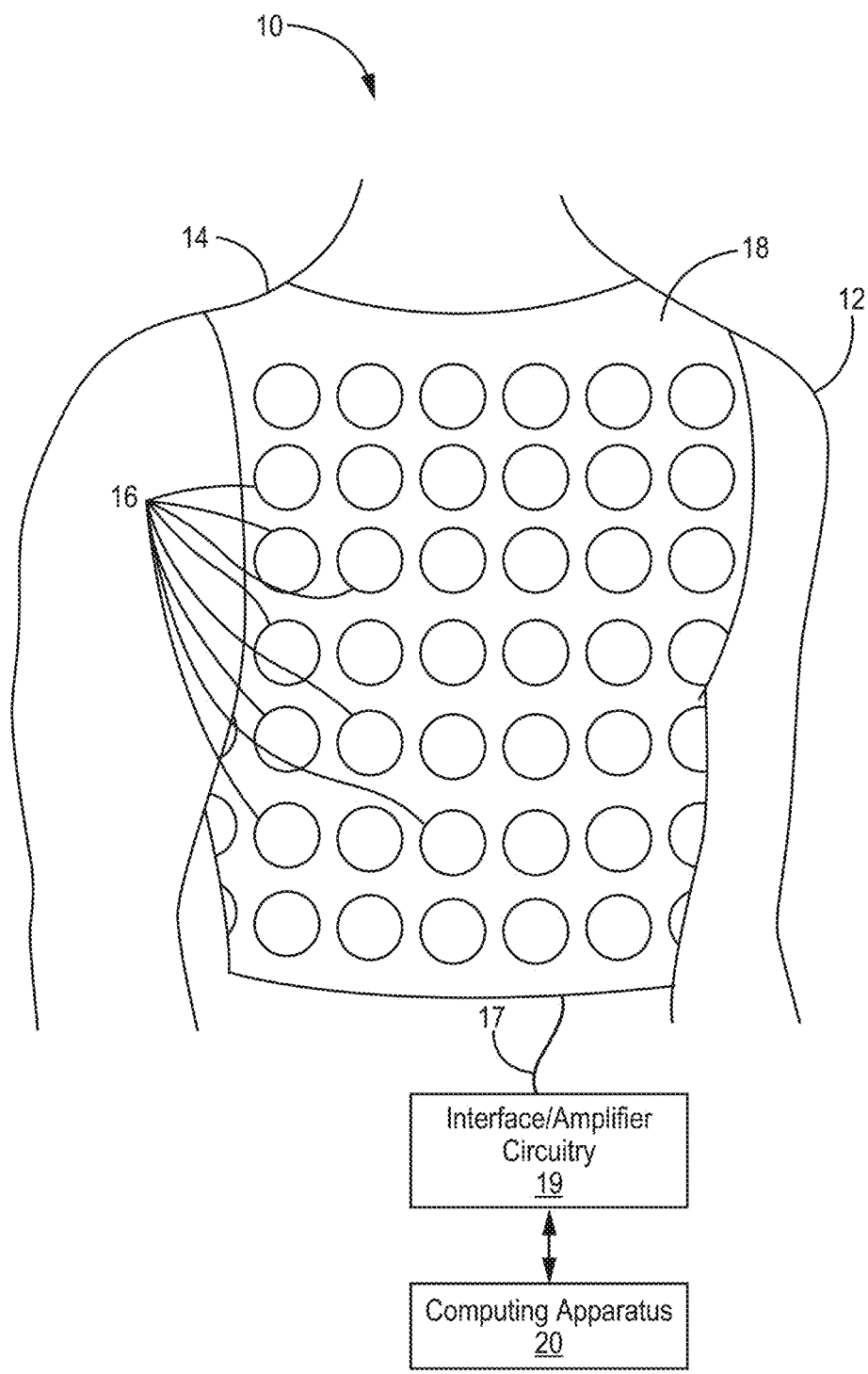
FIG. 3 is a conceptual drawing illustrating another example of the medical device system in conjunction with a patient according to various examples described in this disclosure.

FIG. 3 is a conceptual drawing illustrating another example of the medical device system 10 in conjunction with a patient 12 according to various examples described in this disclosure. FIG. 3 illustrates another exemplary electrode apparatus 14 that includes a plurality of electrodes 16 configured to surround the heart of the patient 12 and record, or monitor, the electrical signals associated with the depolarization and repolarization of the heart after the signals have propagated through the torso of the patient 12. The electrode apparatus 14 may include a vest 18 upon which the plurality of electrodes 16 may be attached, or to which the electrodes 16 may be coupled. In at least one example, the plurality of electrodes 16 may be used to collect electrical information related to the cardiac activity of the heart of patient 12. Similar to the electrode apparatus 14 of FIG. 2, the electrode apparatus 14 of FIG. 3 may include interface/amplifier circuitry 19 electrically coupled to each of the electrodes 16 through a wired connection 17, and configured to transmit signals from the electrodes 16 to computing apparatus 20.

As illustrated, the electrodes 16 may be distributed over the torso of a patient 12, including, for example, the anterior, lateral, posterolateral, anterolateral, and posterior surfaces of the torso of the patient 12. The vest 18 may be formed of fabric with the electrodes 16 attached to the fabric. The vest 18 may be configured to maintain the position and spacing of electrodes 16 on the torso of the patient 12. Further, vest 18 may be marked to assist in determining the location of the electrodes 16 on the surface of the torso of the patient 12. In some examples, there may be about twenty-five to about two-hundred fifty-six electrodes 16 distributed around the torso of the patient 12, though other configurations may have more or fewer electrodes. As described herein, the electrode apparatus 14 may be configured to measure electrical information (e.g., electrical signals) representing different regions of a patient's heart. For example, activation times of different regions of a patient's heart can be approximated from surface electrocardiogram (ECG) activation times measured using surface electrodes in proximity to surface areas corresponding to the different regions of the patient's heart.

The exemplary systems, methods, and interfaces described above with respect to FIG. 3 may be used to provide noninvasive assistance to a user in the evaluation of a patient's cardiac health or status, and/or the valuation of cardiac therapy (e.g., cardiac therapy being presently-delivered to a patient during implantation or after implantation). Further, the exemplary systems, methods, and interfaces may be used to assist a user in the configuration of the cardiac therapy being delivered to a patient. As described above, processing circuitry, such as the processing circuitry of computing apparatus 20, may be configured to detect a noise signal in one or more cardiac signals sensed using electrodes 16 using any of the techniques described throughout this disclosure for analyzing the cardiac signals that may be sensed by electrodes 16. Detection of the noise signal or signals using the example system 10 as illustrated in FIG. 3 may be used to reject signals determined to include noise signals, and to prevent indications of false-positives of cardiac events, such as asystole, associated with the monitoring of a patient. Computing apparatus 20 as shown in FIG. 3 may be configured to perform any of the functions, and to provide any of the features, including display of graphical information associated with cardiac signals and the detection of noise signals, as described throughout this disclosure.

Figure 4:
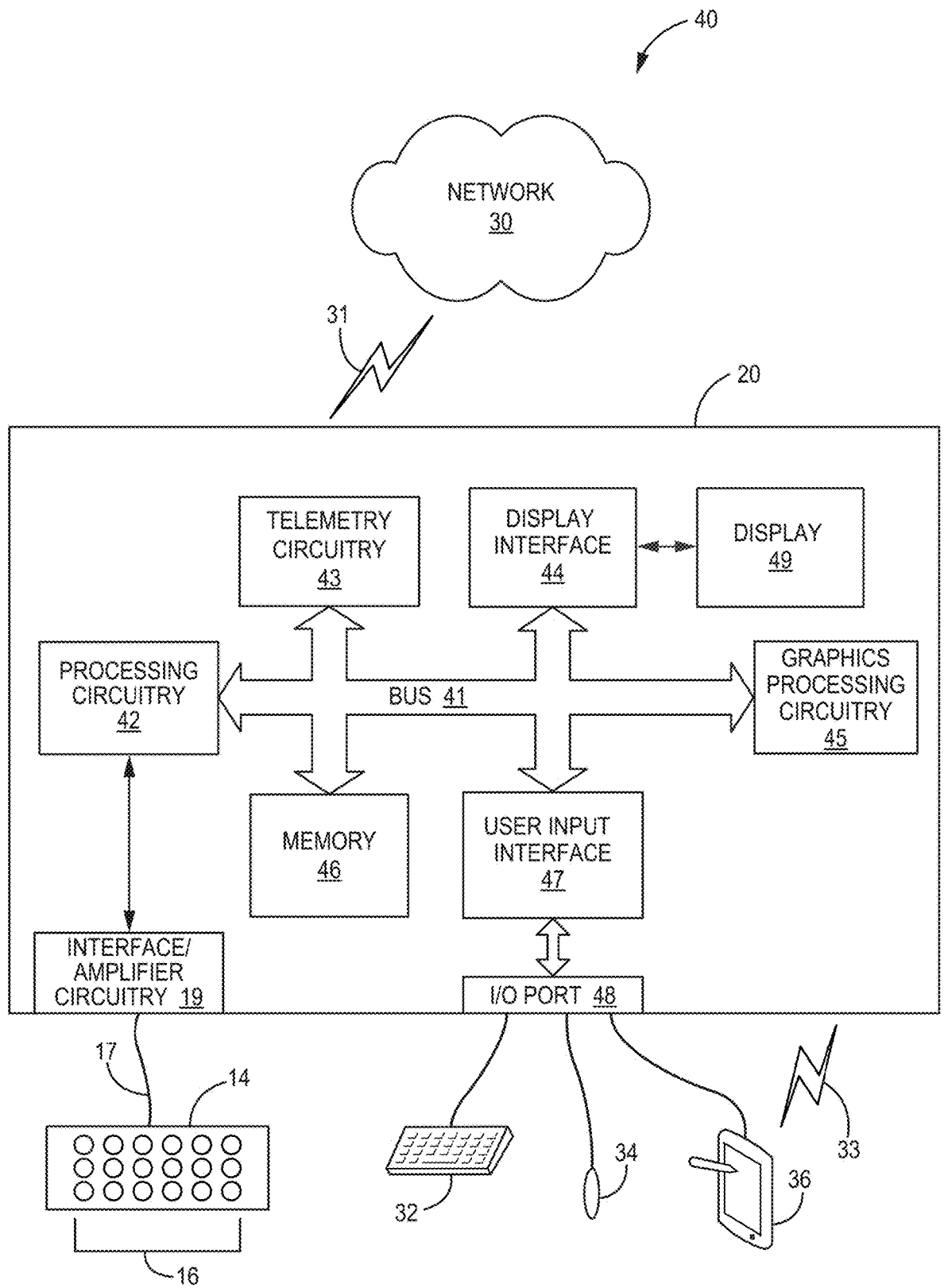
FIG. 4 is a block diagram illustrating an example of a workstation that may be used to implement techniques described this disclosure.

FIG. 4 is a block diagram illustrating an example of a workstation 40 that may be used to implement techniques described this disclosure. Workstation 40 includes computing apparatus 20 that may comprise a personal computer, a desktop computer, a laptop computer, a computer workstation, a wireless communication device (such as, e.g., a mobile telephone, a cellular telephone, a satellite telephone, and/or a mobile telephone handset), a handheld device such as a personal digital assistant (PDA), a mainframe computer or any other type of device that processes and/or displays graphical data.

As illustrated in the example of FIG. 4, computing apparatus 20 includes processing circuitry 42, telemetry circuitry 43, a display interface 44 coupled to a display device 49, graphics processing circuitry 45, memory 46, and a user input interface 47 coupled to an input/output (I/O) port 48. Processing circuitry 42, telemetry circuitry 43, display interface 44, graphics processing circuitry 45, memory 46, and user input interface 47 may communicate with each other using bus 41. Bus 41 may be any of a variety of bus structures, such as a third-generation bus (e.g., a HyperTransport bus or an InfiniBand bus), a second-generation bus (e.g., an Advanced Graphics Port bus, a Peripheral Component Interconnect (PCI) Express bus, or an Advanced eXentisible Interface (AXIM) bus) or another type of bus or device interconnect. It should be noted that the specific configuration of buses and communication interfaces between the different components shown in FIG. 4 is merely exemplary, and other configurations of computing devices and/or other graphics processing systems with the same or different components may be used to implement the techniques of this disclosure.

Processing circuitry 42 may comprise one or more general-purpose and/or a special-purpose processor circuits that control the operation of workstation 40 and computing apparatus 20. Processing circuitry 42 may include one or more processors, such as one or more microprocessors, application specific integrated circuits (ASICs), field programmable gate arrays (FPGAs), digital signal processors (DSPs), or other equivalent integrated or discrete logic circuitry. Processing circuitry 42 may be configured to execute one or more software applications, such as programs stored in memory 46, to perform any of the functions and to provide any of the features ascribed to computing apparatus 20 throughout this disclosure, and any equivalents thereof. For example, processing circuitry 42 may be configured to execute one or more programs that analyze waveforms representative of sensed cardiac signals according to any of the techniques described throughout this disclosure, or any equivalents thereof. In some examples, computing apparatus 20 includes interface/amplifier circuitry 19 coupled through an electrical connection 17 to an electrode apparatus 14 including a plurality of electrodes 16. In various examples, electrode apparatus 14 and electrodes 16 are configured to sense cardiac signals associated with a patient (not shown in FIG. 4), and to provide the sensed signals to processing circuitry 42 for analysis, including analysis to determine if one or more of the sensed cardiac signals includes a noise signal using any of the techniques described throughout this disclosure, or any equivalents thereof.

The software applications that execute on processing circuitry 42 may include, for example, an operating system, signal processing and/or analysis application(s) for analysis of sensed cardiac signals, a word processor application, an email application, a spread sheet application, a media player application, a graphical user interface application or another program that, when executed by the processing circuitry, provide one or any combination of the features and functions ascribed to computing apparatus 20. For example, the software applications that execute on processing circuitry 42 may include applications for performing analysis of one or more sensed cardiac signals received at workstation 40 to determine if the cardiac signals include noise signals. Performing analysis of one or more sensed cardiac signals may include accessing data associated with a patient and the sensed cardiac signals that may be stored in memory 46, and/or accessed through communication link 31 and network 30 and stored in a device located externally to workstation 40 (not shown in FIG. 4 but for example stored at external server 122 and/or one or more of computing devices 125A-125N as illustrated and described with respect to FIG. 9).

Referring again to FIG. 4, processing circuitry 42 may execute one or more graphics rendering applications to provide instructions to cause the rendering of graphical data associated with any of the graphical illustrations, including any waveforms associated with sensed cardiac signals, and any information associated with the analysis of these waveforms, as described throughout this disclosure. In various examples, the graphical data may be provided to graphics processing circuitry 45. Graphics processing circuitry 45 may include circuitry and/or additional software and/or processing circuitry that processes the graphical data, and provides data/and instruction to display interface 44 that allows display interface 44 to render a graphical image, such a rendered image of a waveform associated with a sensed cardiac signal. The graphical data used in rendering by display interface 44 may be provided to display device 49 for display, and may include additional data, such as an indication of the placement of detection windows relative to the displayed waveform, and/or text data and/or menu selectable data, and/or image annotations that may be associated with displayed waveforms. In various examples, the rendered image may include an indication, such as a graphical indication displayed on display device 49, indicative of the detection of a noise signal in a waveform of a cardiac signal being analyzed or otherwise depicted at workstation 40.

In some examples, the software instructions may conform to a graphics application programming interface (API), such as, e.g., an Open Graphics Library (OpenGL®) API, an Open Graphics Library Embedded Systems (OpenGL ES) API, an OpenCL API, a Direct3D API, an X3D API, a RenderMan API, a Weigel API, or any other public or proprietary standard graphics API. The techniques should not be considered limited to requiring a particular API.

In order to process the graphics rendering instructions, processing circuitry 42 may issue one or more graphics rendering commands to graphics processing circuitry 45 to cause graphics processing circuitry 45 to perform some or all of the rendering of the graphics data. In some examples, the graphics data to be rendered may include a list of graphics primitives, e.g., points, lines, triangles, quadrilaterals, triangle strips, etc. used in the generating of the three-dimensional graphical images displayed by display device 49.

Memory 46 may store one or more programs, and may store data, such as patient data and/or device data, and facilitate the transfer of programing and data going into and out of the memory. For example, memory 46 may receive memory read and write commands, and service such commands with respect to memory 46 in order to provide memory services for the components in workstation 40. Memory 46 may also be configured to store one or more parameters, such as numerical quantities or ranges of values that are associated with one or more threshold values that may be utilized by processing circuitry 42 in the analysis of sensed cardiac signals for the purpose of detecting noise signals that may have occurred within the sensed cardiac signals. Memory 46 may include one or more volatile or non-volatile memories or storage devices, such as, for example, random access memory (RAM), static RAM (SRAM), dynamic RAM (DRAM), read-only memory (ROM), erasable programmable ROM (EPROM), electrically erasable programmable ROM (EEPROM), flash memory, a magnetic data media or an optical storage media. Memory 46 may store program modules and/or instructions that are accessible for execution by processing circuitry 42 and for graphics processing circuitry 45, and/or may store data for use by the programs executing on processing circuitry 42 and for graphics processing circuitry 45. For example, memory 46 may store user applications and graphics data associated with the applications. Memory 46 may additionally store information for use by and/or generated by other components of workstation 40. For example, memory 46 may act as a device memory for processing circuitry 42 and for graphics processing circuitry 45, and may store data to be operated on by processing circuitry 42 and/or graphics processing circuitry 45.

In some examples, memory 46 is a non-transitory storage medium. The term "non-transitory" indicates that the storage medium is not embodied in a carrier wave or a propagated signal. However, the term "non-transitory" should not be interpreted to mean that memory 46 is non-movable or that its contents are static. As one example, memory 46 may be removed from workstation 40, and moved to another device. As another example, memory, substantially similar to memory 46, may be inserted into computing apparatus 20. In certain examples, a non-transitory storage medium may store data that can, over time, change (e.g., in RAM). Telemetry circuitry 43 may be configured to receive and transmit, by wired connection or by telemetry, signals incoming to and outgoing from computing apparatus 20. For example, telemetry circuitry 43 may be configured to provide and manage communications, illustrated by communication link 31, that occur between computing apparatus 20 and network 30.

Input devices, such as a keyboard 32, a computer mouse 34, and/or a tablet 36 may be coupled to computing apparatus 20 through I/O port 48, and allow a user to provide inputs to computing apparatus 20. For example, text inputs may be provided to computing apparatus 20 via inputs made to keyboard 32. Actuation, manipulation, and/or selection inputs may be provided to computing apparatus 20 via inputs made using computer mouse 34. For example, movements and/or a continuously variable trackball type inputs provided through computer mouse 34 may be used to manipulate portions of the image(s) provided at display device 49, for example via manipulation of movement and selection using a computer cursor generated in the images provided at display device 49. Inputs to the computer mouse, such as actuation of a "clickable" component of the computer mouse, may be provided as inputs to the computing apparatus 20 to allow a user to indicate a selection, and/or to manipulate (e.g., move, rotate, enlarge, or shrink) graphical features being displayed by display device 49. Tablet 36 may be used to provide inputs, such as selections of menu items provided on the tablet, or through other motions such as gesture motions made across the surface of the tablet to provide inputs to computing apparatus 20 for selection and/or manipulation of the of graphical images being displayed by display device 49. In various examples, one or more of keyboard 32, computer mouse 34, and/or tablet 36 are wireless devices that communicate with computing apparatus 20 via a wireless connection, such as a radio frequency (RF) or an infra-red (IR) technology, illustratively shown as communication link 33 in FIG. 4.

Various examples of computing apparatus 20 may include more or less devices as illustrated in FIG. 4. For example, in some examples, computing apparatus 20 may not include a graphics processing circuitry 45 and/or display interface 44, and wherein processing circuitry 42 performs the functions as described above related to rendering graphical interfaces and/or controlling the display device 49. In various examples, computing apparatus 20 may not include interface/amplifier circuitry 19, wherein interface/amplifier 19 may be located externally relative to computing apparatus 20, or wherein processing circuitry 42 performs the functions and provides one or more of the features ascribed throughout this disclosure to interface/amplifier circuitry 19. Computing apparatus 20 and workstation 40 as illustrated and described with respect to FIG. 4 are intended to be illustrative of non-limiting examples of devices and systems that may be configured to perform the various techniques described in this disclosure, and any equivalents thereof, for detection of noise signals in sensed cardiac signals.

Figure 5:
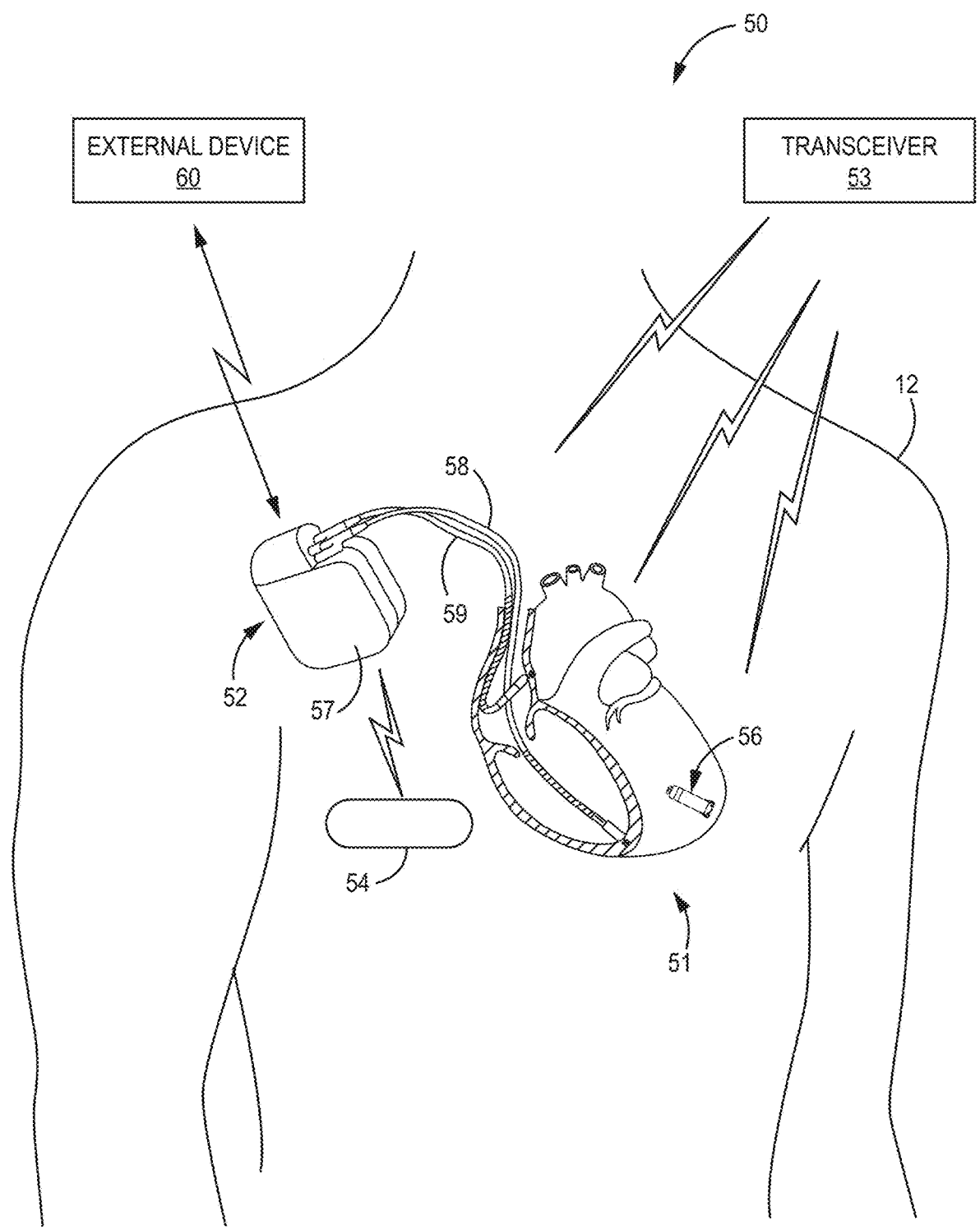
FIG. 5 is a conceptual drawing illustrating an example medical device system in conjunction with a patient according to various examples described in this disclosure.

FIG. 5 is a conceptual drawing illustrating an example medical device system 50 in conjunction with a patient 12 according to various examples described in this disclosure. For purposes of this description, knowledge of cardiovascular anatomy is presumed and details are omitted except to the extent necessary or desirable to explain the context of the techniques of this disclosure. As shown in FIG. 5, system 50 includes implantable medical devices (IMDs) 52, 54, and 56 implanted at various locations within patient 12. System 50 is not limited to example systems that necessarily include all three of these IMDs as illustrated in FIG. 5, and may include only one, any two of these devices, or in some examples all three of these IMDs. Each of these IMDs may include sensors (e.g., electrodes) that are configured to sense cardiac activity of patient 12, and provide cardiac signals based on the sensed cardiac activity of the patient. In various examples, the devices themselves may perform analysis of the sensed cardiac signals to detect the presence of one or more noise signals within the cardiac signals being sensed in accordance with any of the techniques described in this disclosure, and any equivalents thereof. In various examples, one or more of the IMDs 52, 54, and 56 may provide the sensed cardiac signal or signals as an output to another device, such as another one of the IMDs, or for example to an external device, such as external device 60 and/or transceiver 53, wherein the analysis of the cardiac signal or signals to detect noise signal(s) within the sensed cardiac signal(s) may be performed by the external device or other devices external to patient 12, and in accordance with any of the noise signal detection techniques described throughout this disclosure, and any equivalents thereof.

In the illustrated example shown in FIG. 5, medical device system 50 may include an IMD 52 coupled to a ventricular lead 58 and an atrial lead 59. In various examples, IMD 52 is an implantable cardioverter-defibrillator (ICD) capable of delivering pacing, cardioversion and defibrillation therapy to the heart 51 of a patient 12. Ventricular lead 58 and atrial lead 59 are electrically coupled to IMD 52 and extend into the heart 51 of patient 12. Ventricular lead 58 includes electrodes (not labeled in FIG. 5) positioned on the lead in the patient's right ventricle (RV) for sensing ventricular EGM signals and pacing in the RV. Atrial lead 59 includes electrodes (not labeled in FIG. 5) positioned on the lead in the right atrium (RA) of patient 12 for sensing atrial EGM signals and pacing in the RA. Ventricular lead 58 and/or atrial lead 59 may also include coil electrodes used to deliver cardioversion and defibrillation shocks. The term "anti-tachyarrhythmia shock" may be used herein to refer to both cardioversion shocks and defibrillation shocks. IMD 52 may use both ventricular lead 58 and atrial lead 59 to acquire cardiac electrogram (EGM) signals from patient 12 and to deliver therapy in response to the acquired data. IMD 52 is shown as having a dual chamber IMD configuration, but other examples may include one or more additional leads, such as a coronary sinus lead extending into the right atrium, through the coronary sinus and into a cardiac vein to position electrodes along the left ventricle (LV) for sensing LV EGM signals and delivering pacing pulses to the LV. In other examples, a medical device system may be a single chamber system, or otherwise not include atrial lead 59. In some examples IMD 52 may be an extravascular ICD coupled to subcutaneous or substernal leads, instead of or in addition to intracardiac leads as shown.

Processing circuitry, sensing circuitry, and other circuitry configured for performing the techniques described herein with respect to IMD 52 may be housed within a sealed housing 57 of IMD 52. Housing 57 (or a portion thereof) may be conductive so as to serve as an electrode for pacing or sensing, or as an active electrode during defibrillation. As such, housing 57 may also be referred to herein as "housing electrode" 57. Housing 57 may include one or more electrodes with a high-capacitance portion and a low-capacitance portion. The high-capacitance portion and the low-capacitance portion may be formed using two different materials.

IMD 52 may sense cardiac activity associated with heart 51, and may analyze the sensed cardiac signals to detect noise signals present within the sensed cardiac signals. In some examples, IMD 52 may provide an output signal in response to a detection of a noise signal detected within any of the sensed cardiac signals sensed by IMD 52. IMD 52 may provide an alarm output signal to an external device when a noise signal is detected in the sensed cardiac signals. In some examples, IMD 52 may modify for example the electrodes being used to sense cardiac signals of heart 51, and/or may modify therapy parameters including which electrodes of leads 58, 59, and/or use of housing 57 are used to deliver stimulation therapy based on the detection of one or more noise signals within the sensed cardiac signals. In some examples, IMD 52 may transmit EGM signal data and cardiac rhythm episode data, as well as data regarding delivery of therapy by IMD 52 and/or the detection of a noise signal within a sensed cardiac signal, to an external device such as external device 60. For example, external device 60 as illustrated in FIG. 5 may be a computing device, e.g., used in a home, ambulatory, clinic, or hospital setting, to communicate with IMD 52 via wireless telemetry. External device 60 may be coupled to a remote patient monitoring system, such as Carelink®, available from Medtronic plc, of Dublin, Ireland. External device 60 may be, as examples, a programmer, external monitor, or consumer device, e.g., smart phone.

External device 60 may be used to program commands or operating parameters into IMD 52 for controlling its functioning, e.g., when configured as a programmer for IMD 52. External device 60 may be used to interrogate IMD 52 to retrieve data, including device operational data as well as physiological data accumulated in IMD 52 memory. The interrogation may be automatic, e.g., per a schedule, or in response to a remote or local user command. Examples of communication techniques used by IMD 52 and external device 60 may include TCC and RF telemetry, which may be an RF link established via Bluetooth®, WiFi, or medical implant communication service (MICS). External device 60 may receive data corresponding to the sensed cardiac signals sensed by IMD 52, and may perform analysis of the received data to detect the presence of noise signals within the sensed cardiac signals using any of the techniques described in this disclosure, and any equivalents thereof. Upon the detection of a noise signal in an analyzed cardiac signal, external device 60 may communicate with IMD 52 regarding instructions related to the configuration and performance of sensing and/or therapy delivery being performed or potentially performed by IMD 52. For example, upon a determination by external device 60 that data received from IMD 52 related to a sensed cardiac signal includes a detected noise signal, external device 60 may communicate back to IMD 52 one or more instructions related to the detection of the noise signal, including instruction to discontinue use of one or more electrodes associated with the noise signal for sensing purposes, and/or modification to the therapy treatment that may be administered by IMD 52, for example based on a false-positive indication of asystole in patient 12 caused by corruption to the sensed cardiac signal due to the noise signal.

In addition, system 50 may include transceiver 53 wirelessly coupled to communicate with IMD 52. Transceiver 53 may server as an access point for communications to and from IMD 52 with other external devices (not shown in FIG. 5, but for example external device 122 as illustrated and described with respect to FIG. 9), and may provide any of the features and perform any of the functions, in some examples in conjunction with other external devices, described above with respect to external device 60.

Referring again to FIG. 5, medical device system 10 includes IMD 54, which may be referred to as an implantable monitoring device, or an implantable hub device, or an implantable loop recorder. In the illustrated example, IMD 54 is an insertable cardiac monitor (ICM) capable of sensing and recording cardiac electrogram (EGM) (also referred to as an ECG or EKG electrocardiogram when external electrodes are placed on the skin) signals from a position outside of heart 51 via electrodes coupled to or forming part of IMD 54. In some examples, IMD 54 includes or is coupled to one or more additional sensors, such as accelerometers, that generate one or more signals that vary based on patient motion and/or posture, blood flow, or respiration. IMD 54 may monitor a physiological parameter indicative of patient state, such as posture, heart rate, activity level, and/or respiration rate. IMD 54 may be implanted outside of the thorax of patient 12, e.g., subcutaneously or submuscularly, such as the pectoral location illustrated in FIG. 5. In some examples, IMD 54 may take the form of a Reveal LINQ® ICM, available from Medtronic plc, of Dublin, Ireland.

In some examples, IMD 54 may transmit data and other information to an external device, such as external device 60 and/or transceiver 53, in a manner similar to that described above with respect to IMD 52. In various examples, IMD 54 is configured to wirelessly communicate with one or more of these external devices. External device 60 may be used to program commands or operating parameters into IMD 54 for controlling the functioning of the IMD. External devices such as external device 60 or external devices coupled through transceiver 53 may be used to interrogate IMD 54 to retrieve data, including information and data associated with sensed cardiac signals sensed by IMD 54. The interrogation may be automatic, e.g., according to a schedule, or in response to a remote or local user command. One or more of these external devices may also be referred to as an "instrument" or as a group of instruments. The communications between IMD 54 and the external devices is not limited to any particular communication technique or communication protocol, and in some examples, include tissue conductance communication (TCC) or RF telemetry, which may be an RF link established via Bluetooth®, WiFi, or medical implant communication service (MICS).

External devices such as external device 60 and/or external devices coupled through transceiver 53 may receive data corresponding to the sensed cardiac signals sensed by IMD 54, and may perform analysis of the received data to detect the presence of noise signals within the sensed cardiac signals using any of the techniques described in this disclosure, and any equivalents thereof. In some examples, IMD 54 is configured to transmit data associated with sensed cardiac signals to another IMD, such as IMD 52, wherein IMD 52 is configured to receive the data associated with the sensed cardiac signals, and to perform analysis of the received data to detect the presence of any noise signals that may have occurred within the cardiac signals. In some examples where IMD 54 performs the analysis of the sensed cardiac signals, IMD 54 may provide an alarm output signal in response to a detection of a noise signal detected within any of the sensed cardiac signals. IMD 54 may provide the alarm output signal to another IMD, such as IMD 52, or to an external device when a noise signal is detected by IMD 54. In some examples, IMD 54 may modify for example the electrodes being used to sense cardiac signals of heart 51 based on the detection of one or more noise signals within the sensed cardiac signals sensed by IMD 54.

In some examples, medical device system 50 may also include an intracardiac pacing device IMD 56. In the illustrated example, IMD 56 is implanted in the left-ventricle of patient 12, e.g., internal to the heart 51 of patient 12. In some examples, one or more IMDs like IMD 56 (not shown in FIG. 5) may additionally or alternatively be implanted within other chambers of heart 51, or attached to the heart epicardially. IMD 56 may be configured to sense electrical activity of heart 51 and deliver pacing therapy, e.g., bradycardia pacing therapy, cardiac resynchronization therapy (CRT), anti-tachycardia pacing (ATP) therapy, and/or post-shock pacing, to heart 51. In some examples, IMD 56 may communicate with IMD 52 when IMD 52 is present in system 50 to receive the sensed electrical signal associated with the activity of heart 51, and/or receive information related to the sensed electrical activity from IMD 54 when IMD 54 is provided as part of system 50. IMD 56 may be attached to an interior wall of heart 51 via one or more fixation elements (not shown in FIG. 5) that penetrate the tissue in the vicinity of IMD 56. These fixation elements may secure IMD 56 to the cardiac tissue and retain an electrode (e.g., a cathode or an anode) on the housing of IMD 56 in contact with the cardiac tissue. In addition to delivering pacing pulses, IMD 56 may be capable of sensing electrical signals using the electrodes carried on the housing of IMD 56. These electrical signals may be electrical signals generated by cardiac muscle and indicative of depolarizations and repolarizations of heart 51 at various times during the cardiac cycle.

In some examples, IMD 52 and IMD 56 may both be configured to deliver pacing therapy. In such examples, IMD 52 and IMD 56 may delivery pacing therapy to the right and/or left ventricles of heart 51, respectively, to provide CRT pacing. Additionally, IMD 52 and IMD 56 may both be configured to detect tachyarrhythmias, and deliver anti-tachyarrhythmia therapy. IMD 52 and IMD 56 may be configured to coordinate their cardiac rhythm detection and treatment activities. In some examples, IMD 52 and IMD 56 may engage in wireless communication between IMD 52 and IMD 56 to facilitate such coordinated activity. The wireless communication may by via TCC, and may be one-way communication in which one device is configured to transmit communication messages and the other device is configured to receive those messages, or two-way communication in which each device is configured to transmit and receive communication messages. In some examples, one or both of IMD 52 and IMD 54 may act as a bridge for communications between IMD 56 and one or more of external device 60 and/or transceiver 53.

In some examples, IMD 56 may include sensor circuitry and processing circuitry configured to perform analysis of the cardiac signals sensed by IMD 56, including analysis of the sensed cardiac signal to detect the presence of one or more noise signals within the sensed cardiac signals according to any of the techniques described in this disclosure, and any equivalents thereof. IMD 56 may provide an alarm output signal in response to a detection of a noise signal detected within any of the sensed cardiac signals sensed by IMD 56. IMD 56 may provide the alarm output signal to an external device when a noise signal is detected, such as external device 60 and/or transceiver 53, or to another IMD such as IMD 52. In some examples, IMD 56 may modify for example the electrodes of IMD 56 being used to sense cardiac signals of heart 51, and/or modify therapy parameters including which electrodes (not shown in FIG. 5) of IMD 56 that are being or that may be used to deliver stimulation therapy based on the detection of one or more noise signals within the sensed cardiac signals. In some examples, IMD 56 may transmit data corresponding to sensed cardiac signals to another device, such as IMD 52 and/or external devices such as external device 60 and/or transceiver 53, wherein the other device or devices are arranged to perform the analysis of the cardiac signals sensed by IMD 56. Upon detection of a noise signal within the cardiac signals sensed by IMD 56, these other devices may be configured to communication with IMD 56 regarding the detection of the noise signal in any manner as described above with respect to IMD 52 and/or IMD 54.

Thus, as shown in FIG. 5, a medical device system 50 may include one or more IMDs implanted in a patient 12, each of the IMDs configured to sense cardiac activity associated with the heart 51 of patient 12, and to generate sensed cardiac signals corresponding to the cardiac activity. The IMDs themselves may perform analysis of these sensed cardiac signals to detect any occurrences of noise signals within the sensed cardiac signal, or may transmit the data corresponding to the sensed cardiac signal to another device which may perform the analysis. Analysis of the sensed cardiac signals may include use of any of the techniques described throughout this disclosure, and any equivalents thereof, associated with the detection of noise signals within sensed cardiac signals. Upon detection of a noise signal occurring within a sensed cardiac signal, an alarm output signal may be generated by the device performing the analysis. The alarm output signal may be further processed to reconfigure the sensing channels, for example the particular electrodes, that may be utilized by an IMD for further sensing of cardiac activity associated with patient 12. In addition, the alarm output signal may be further processed by the system to configure and/or control the application of, or the potential application of, stimulation therapy to patient 12. For example, detection of a noise signal may result in reconfiguration of the particular electrodes being used by an IMD of system 50 for sensing cardiac signals associated with the cardiac activity of patient 12. In some examples, detection of a noise signal may be used to prevent or to alter the application of a particular stimulation therapy to patient 12 based on a false-positive indication of a cardiac event, such as asystole, caused by the corruption of the sensed cardiac signal due to the occurrence of the noise signal.

Figure 6:
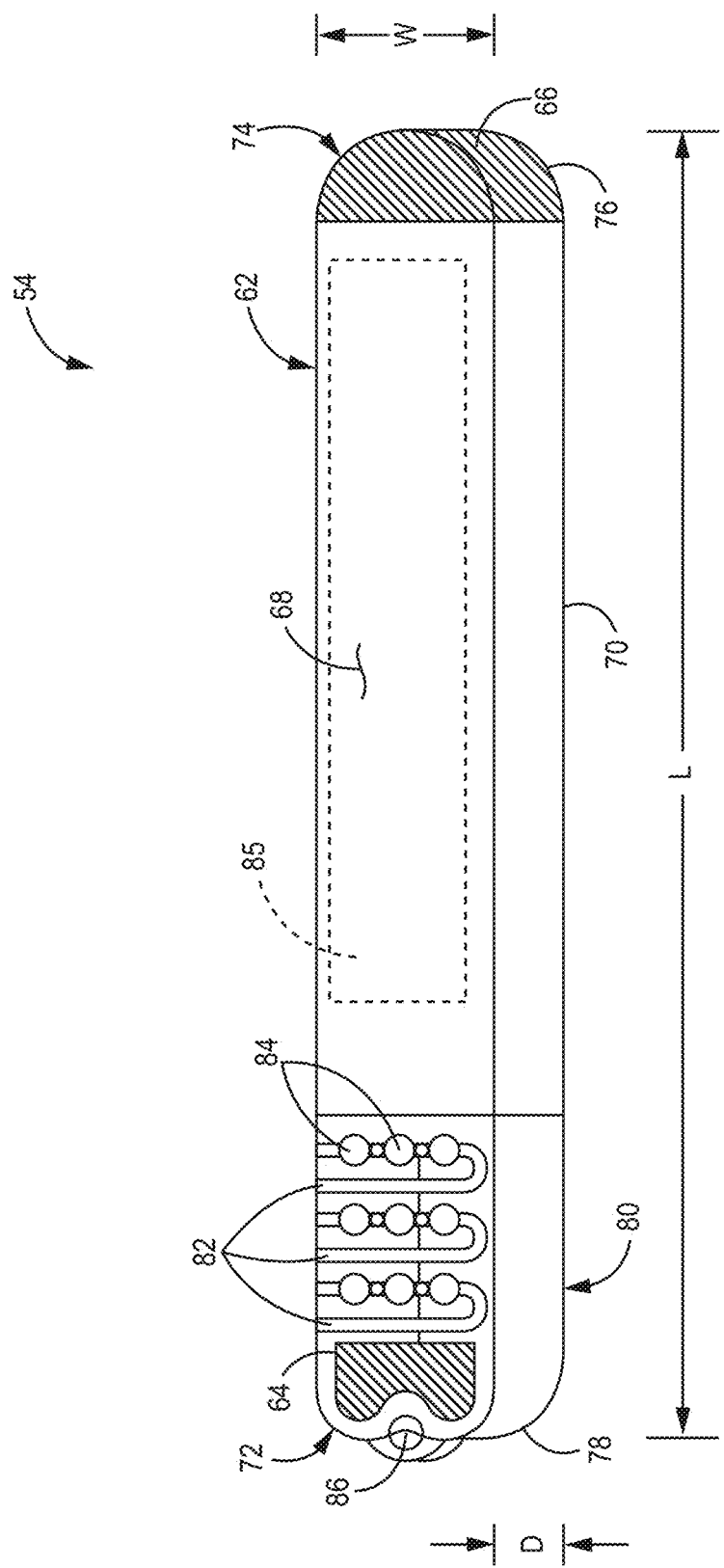
FIG. 6 is a conceptual drawing illustrating an example configuration of an IMD of FIG. 5.

FIG. 6 is a conceptual drawing illustrating an example configuration of IMD 54 of FIG. 5. As shown in FIG. 6, IMD 54 is an example of an implantable medical device that may sense cardiac signals, and in some examples, may analyze these signals to determine if the sensed cardiac signals include a noise signal. In the example shown in FIG. 6, IMD 54 may be an implantable loop recorder diagnostic device, such as the Medtronic Reveal LINQ® Insertable Cardiac Monitor developed by Medtronic, plc, of Dublin, Ireland. IMD 54 may be embodied as a monitoring device having housing 62, proximal electrode 64 and distal electrode 66. Housing 62 may further comprise first major surface 68, second major surface 70, proximal end 72, and distal end 74. Housing 62 encloses electronic circuitry located inside the IMD 54, and protects the circuitry contained therein from body fluids when IMD 54 is implanted in a patient. Electrical feedthroughs may provide electrical connection of electrodes 64 and 66 or, in some examples, electrode 66 may comprise an uninsulated portion of an electrically conductive housing 62. These electrodes may be used to sense cardiac signals once IMD 54 has been implanted within a patient. IMD 54 may also analyze the sensed cardiac signals using any of the techniques described in this disclosure, and any equivalents thereof, to detect noise signals present within the cardiac signals, and to provide an alarm output signal indicative of the detection of any noise signals within the analyzed cardiac signals. A power source 85, such as a battery, may be provided within IMD 54, which provides power to the electronic circuitry of IMD 54, and may comprise a rechargeable power source that may be inductively recharged after IMD 54 has been implanted in a patient without the need to remove and re-implant IMD 54.

In the example shown in FIG. 6, IMD 54 may be defined by a length L, a width W, and thickness or depth D, in some examples in the form of an elongated rectangular prism wherein the length L is much larger than the width W, which in turn is larger than the depth D. In one example, the geometry of the IMD 54, in particular a width W greater than the depth D, is selected to allow IMD 54 to be inserted under the skin of the patient using a minimally invasive procedure and to remain in the desired orientation during insertion. For example, the device shown in FIG. 6 includes radial asymmetries (notably, the rectangular/prismatic shape) along the longitudinal axis that maintains the device in the proper orientation following insertion. In one example, the spacing between proximal electrode 64 and distal electrode 66 may range from thirty millimeters (mm) to fifty-five mm, thirty-five mm to fifty-five mm, and from forty mm to fifty-five mm, and may be any range or individual spacing from twenty-five mm to sixty mm. In addition, IMD 54 may have a length L that ranges from thirty mm to about seventy mm. In other examples, the length L may range from forty mm to sixty mm, forty-five mm to sixty mm, and may be any length or range of lengths between about thirty mm and about seventy mm. In addition, the width W of major surface 68 may range from three mm to ten mm, and may be any single or range of widths between three mm and ten mm. The thickness of depth D of IMD 54 may range from two mm to nine mm. In other examples, the depth D of IMD 54 may range from two mm to five mm and may be any single or range of depths from two mm to nine mm.

In addition, IMD 54 according to an example of the present disclosure has a geometry and size designed for ease of implant and patient comfort. Examples of IMD 54 described in this disclosure may have a volume of three cubic centimeters (cm) or less, one-and-a-half cubic cm or less, or any volume between three and one-and-a-half cubic centimeters. In addition, in the example shown in FIG. 6, proximal end 72 and distal end 74 are rounded to reduce discomfort and irritation to surrounding tissue once inserted under the skin of the patient. IMD 54, including instrument, introducer, and method for inserting IMD 54 are described, for example, in U.S. Patent Application Publication No. 2014/0276928, incorporated herein by reference in its entirety.

In the example shown in FIG. 6, once inserted within the patient, the first major surface 68 faces outward, toward the skin of the patient while the second major surface 70 is located opposite the first major surface 68. Consequently, the first and second major surfaces may face in directions along a sagittal axis of a patient (see e.g., FIG. 5), and this orientation may be consistently achieved upon implantation due to the dimensions of IMD 54. Additionally, an accelerometer, or axis of an accelerometer, may be oriented along the sagittal axis.

As shown in FIG. 6, proximal electrode 64 and distal electrode 66 are used to sense cardiac signals, e.g. ECG signals, intra-thoracically or extra-thoracically, which may be submuscularly or subcutaneously. ECG signals may be stored in a memory of the IMD 54, and ECG data may be transmitted via integrated antenna 82 (receiving antenna) to another medical device, which may be another implantable device or an external device, such as external device 60 illustrated in FIG. 5. In some examples, the external device may analyze the data transmitted by IMD 54 to determine if any noise signals are present within the sensed cardiac signals associated with the transmitted data. Referring again to FIG. 6, in some examples electrodes 64 and 66 may additionally or alternatively be used for sensing any biopotential signal of interest, which may be, for example, an electrogram (EGM), electroencephalogram (EEG) signal, electromyography (EMG) signal, or a nerve signal, from any implanted location.

In the example shown in FIG. 6, proximal electrode 64 is in close proximity to the proximal end 72 and distal electrode 66 is in close proximity to distal end 74. In this example, distal electrode 66 is not limited to a flattened, outward facing surface, but may extend from first major surface 68 around rounded edges 76 and/or end surface 78 and onto the second major surface 70 so that the electrode 66 has a three-dimensional curved configuration. In the example shown in FIG. 6, proximal electrode 64 is located on first major surface 68 and is substantially flat, outward facing. However, in other examples proximal electrode 64 may utilize the three-dimensional curved configuration of distal electrode 66, providing a three-dimensional proximal electrode (not shown in this example). Similarly, in other examples distal electrode 66 may utilize a substantially flat, outward facing electrode located on first major surface 68 similar to that shown with respect to proximal electrode 64. The various electrode configurations allow for configurations in which proximal electrode 64 and distal electrode 66 are located on both first major surface 68 and second major surface 70. In other configurations, such as that shown in FIG. 6, only one of proximal electrode 64 and distal electrode 66 is located on both major surfaces 68 and 70, and in still other configurations both proximal electrode 64 and distal electrode 66 are located on one of the first major surface 68 or the second major surface 70 (i.e., proximal electrode 64 located on first major surface 68 while distal electrode 66 is located on second major surface 70). In another example, IMD 54 may include electrodes on both major surface 68 and 70 at or near the proximal and distal ends of the device, such that a total of four electrodes are included on IMD 54. Electrodes 64 and 66 may be formed of a plurality of different types of biocompatible conductive material, e.g. stainless steel, titanium, platinum, iridium, or alloys thereof, and may utilize one or more coatings such as titanium nitride or fractal titanium nitride.

In the example shown in FIG. 6, proximal end 72 includes a header assembly 80 that includes one or more of proximal electrode 64, integrated antenna 82, anti-migration projections 84, and/or suture hole 86. Integrated antenna 82 is located on the same major surface (i.e., first major surface 68) as proximal electrode 64 and is also included as part of header assembly 80. Integrated antenna 82 allows IMD 54 to transmit and/or receive data. In other examples, integrated antenna 82 may be formed on the opposite major surface as proximal electrode 64, or may be incorporated within the housing 62 of IMD 54. Antenna 82 may be coupled to recharging circuitry (not shown in FIG. 3), wherein antenna 82 is configured to enable inductive power transfer of energy inductively generated in the antenna 82 by electromagnetic fields imposed on the antenna for the purpose of recharging, by the recharging circuitry, the power source 85 provided within IMD 54. In the example shown in FIG. 6, anti-migration projections 84 are located adjacent to integrated antenna 82 and protrude away from first major surface 68 to prevent longitudinal movement of the device. In the example shown in FIG. 6, anti-migration projections 84 includes a plurality (e.g., nine) small bumps or protrusions extending away from first major surface 68. As discussed above, in other examples anti-migration projections 84 may be located on the opposite major surface as proximal electrode 64 and/or integrated antenna 82. In addition, in the example shown in FIG. 6 header assembly 80 includes suture hole 86, which provides another means of securing IMD 54 to the patient to prevent movement following insert. In the example shown, suture hole 86 is located adjacent to proximal electrode 64. In one example, header assembly 80 is a molded header assembly made from a polymeric or plastic material, which may be integrated or separable from the main portion of IMD 54.

Figure 7:
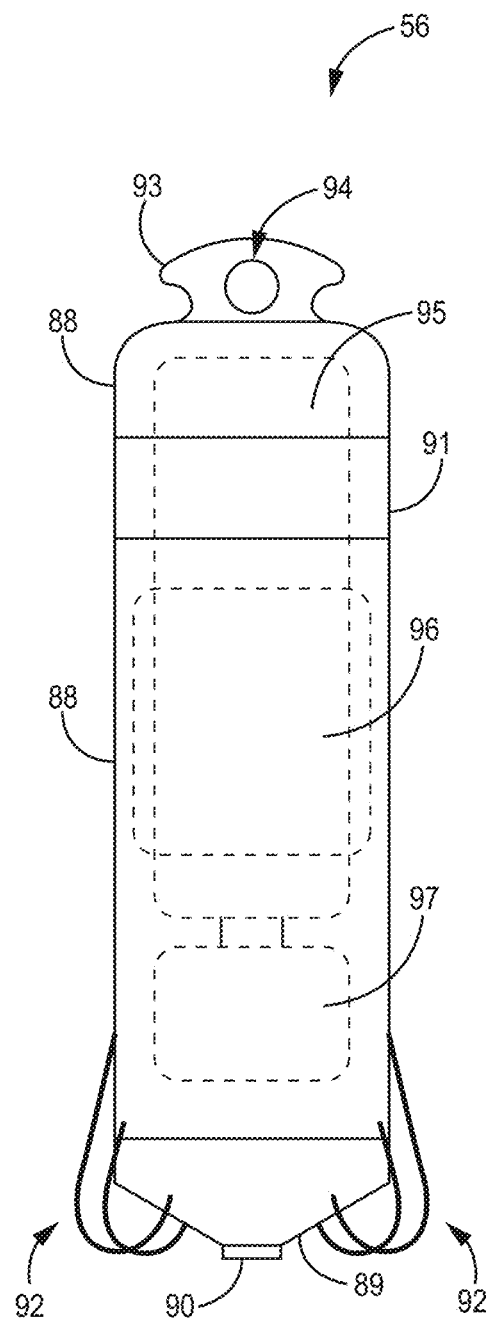
FIG. 7 is a conceptual drawing illustrating an example configuration of another IMD of FIG. 5.

FIG. 7 is a conceptual drawing illustrating an example configuration of another IMD 56 of FIG. 5. As shown in FIG. 7, IMD 56 comprises an intracardiac pacing device, sometimes referred to as a leadless pacing device, that may be configured to sense cardiac signals that may be analyzed for a noise signal according to the various examples described in this disclosure, and any equivalents thereof. In some examples, IMD 56 is a Medtronic® Micra® Transcatheter Pacing System developed by Medtronic, plc, of Dublin, Ireland. IMD 56 may be configured to be implanted in the left ventricle of the heart of a patient, as depicted in FIG. 5. IMD 56 as shown in FIG. 7 is an example of an implantable medical device that may sense cardiac signals when implanted within a patient, and may analyze the sensed cardiac signals to determine if there are any noise signals present within the sensed cardiac signals. IMD 56 may also be configured to output an alarm output signal, for example to an external device, in response to a detection of a noise signal within a cardiac signal being sensed by IMD 56. IMD 56 may also be configured to sense cardiac signals, and to transmit data associated with the sensed cardiac signals to an external device or external devices, the external device or devices configured to perform analysis of the data to determine if a noise signal exists within the sensed cardiac signal sensed by IMD 56. In some examples, upon detection of a noise signal by the external device or devices, the external device(s) may transmit information and/or instructions back to IMD 56 to further control IMD 56 based on the detection of the noise signal(s). As shown in FIG. 7, IMD 56 includes electronic circuitry 97 including communication circuitry coupled to an antenna 96, and a power source 95, for example a battery, that is coupled to the electronic circuitry and configured to provide power to the electronic circuitry. Electronic circuitry 97 of IMD 56 may include processing circuitry, comprising one or more computer processors, that may be configured to analyze sensed cardiac signals sensed by IMD 56, and to determine if any noise signals are present within the sensed cardiac signals using any of the techniques described in this disclosure, and any equivalents thereof. The processing circuitry may provide an alarm output signal in response to detection of a noise signal in any of the sensed cardiac signal, for example to one or more external devices outside IMD 56.

Communication circuitry included in electronic circuitry 97 of IMD 56 may be configured to provide wireless communication between IMD 56 and other devices, such as external device 60 as shown in FIG. 5. In addition, antenna 96 of IMD 56 as shown in FIG. 7 may be configured to receive electrical energy imposed on IMB 56 as electromagnetic fields, and to recharge battery 95 using energy inductively coupled to antenna 96 from these fields (also known as wireless power transfer). In order to save space and keep IMD 56 as small as possible, antenna 96 may be a planar antenna, such as an antenna formed as a conductive trace on a substrate, or three-dimensional antenna for example.

IMB 56 includes case 88, cap 89, electrode 90, electrode 91, fixation mechanisms 92, flange 93, and opening 94. Together, case 88 and cap 89 may be considered the housing of IMD 56. In this manner, case 88 and cap 89 may enclose and protect the various electrical components, e.g., circuitry, within IMD 56. Case 88 may enclose substantially all of the electrical components, and cap 89 may seal case 88 and create the hermetically sealed housing of IMB 56. Although IMD 56 is generally described as including one or more electrodes, IMD 56 may typically include at least two electrodes (e.g., electrodes 90 and 91) to deliver an electrical signal (e.g., therapy such as cardiac pacing) and/or provide at least one sensing vector including sensed cardiac signals from cardiac activity of a patient where IMD 56 has been implanted.

Electrodes 90 and 91 are carried on the housing created by case 88 and cap 89. In this manner, electrodes 90 and 91 may be considered leadless electrodes. In the example of FIG. 7, electrode 90 is disposed on the exterior surface of cap 89. Electrode 90 may be a circular electrode positioned to contact cardiac tissue upon implantation. Electrode 91 may be a ring or cylindrical electrode disposed on the exterior surface of case 88. Both case 88 and cap 89 may be formed from electrically insulating material.

Electrode 90 may be used as a cathode and electrode 91 may be used as an anode, or vice versa, for delivering cardiac pacing such as bradycardia pacing, CRT, ATP, or post-shock pacing. However, electrodes 90 and 91 may be used in any stimulation configuration. In addition, electrodes 90 and 91 may be used to detect intrinsic electrical signals from cardiac muscle. Tip electrode 90 may be configured to contact cardiac tissue such as an interior wall of the left ventricle of the heart of a patient where IMD 56 is implanted.

Fixation mechanisms 92 may attach and secure IMD 56 to cardiac tissue. Fixation mechanisms 92 may be active fixation tines, screws, clamps, adhesive members, or any other mechanisms for attaching a device to tissue. Fixation mechanisms 92 may be constructed of a memory material, such as a shape memory alloy (e.g., nickel titanium), that retains a preformed shape, e.g., as shown in FIG. 7. During implantation, fixation mechanisms 92 may be flexed forward to pierce tissue and allowed to flex back towards case 88. In this manner, fixation mechanisms 92 may be embedded within the target tissue.

Flange 93 may be provided on one end of case 88 to enable tethering or extraction of IMD 56. For example, a suture or other device may be inserted around flange 93 and/or through opening 94 and attached to tissue. In this manner, flange 93 may provide a secondary attachment structure to tether or retain IMD 56 within the heart. Flange 93 and/or opening 94 may also be used to extract IMD 56 once the IMD needs to be explanted (or removed) from the patient if such action is deemed necessary. IMD 56 is one example of a pacing device configured to include one or more electrodes according to this disclosure. However, other implantable medical devices may be configured to include one or more electrodes similar to those described with respect to IMD 56.

Figure 8:
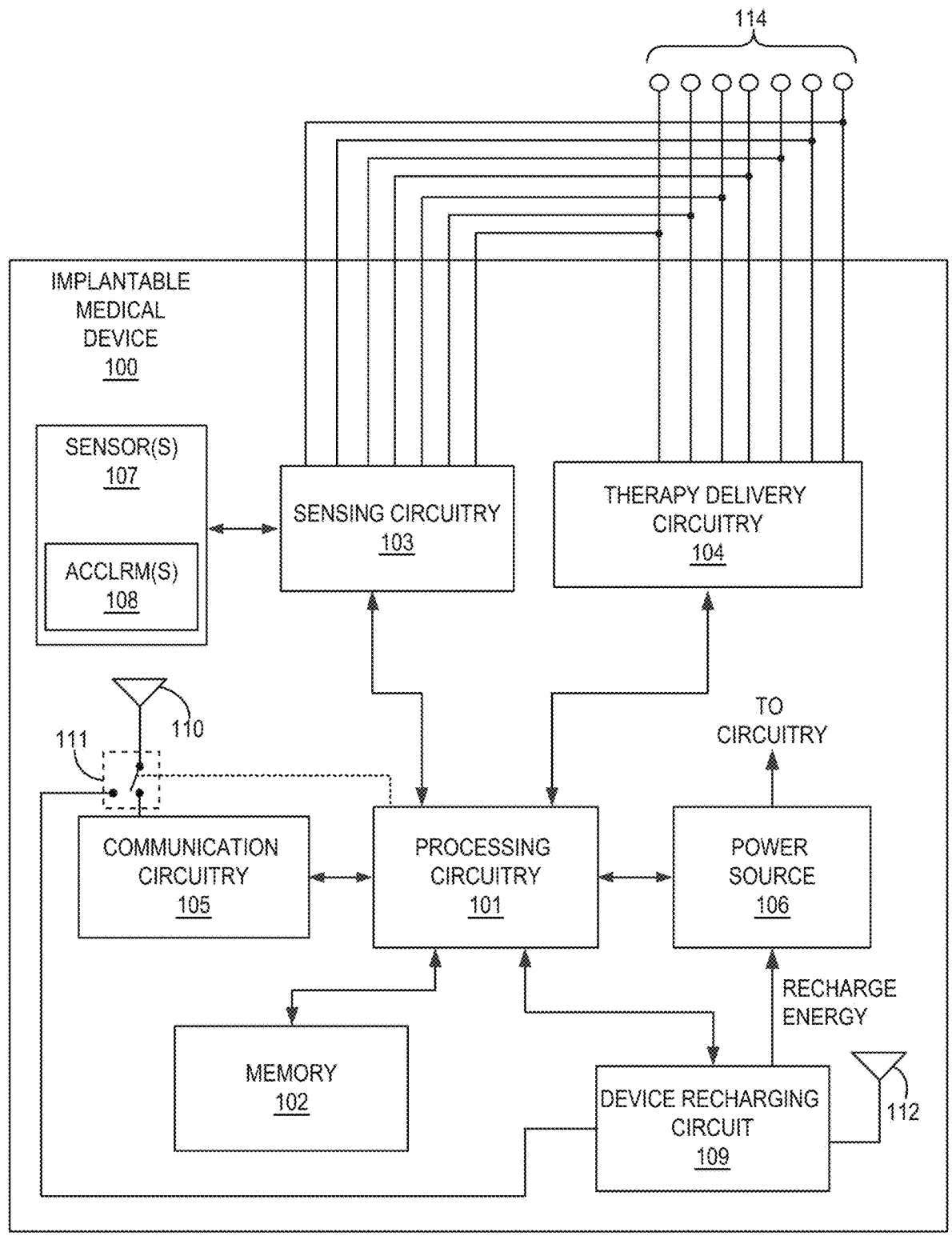
FIG. 8 is a functional block diagram illustrating an example configuration of an IMD according to various examples described in this disclosure.

FIG. 8 is a functional block diagram illustrating an example configuration of an IMD 100 according to various examples described in this disclosure. IMD 100 may correspond to any of IMDs 52, 54, or 56 described and illustrated with respect to FIGS. 5, 6, and 7, or another IMD configured to detect noise signals within sensed cardiac signals according to any of the techniques described herein, and any equivalents thereof. IMD 100 includes a power source 106 that may be coupled to the electronic circuitry provided in IMD 100, and is configured to provide electrical power to these circuits. IMD 100 may be inductively rechargeable by providing electromagnetic energy to the IMD 100, wherein energy from these imposed fields may induce an electrical energy into antenna 110 coupled to communication circuitry 105. In addition, antenna 110 may also be coupled to device recharging circuitry 109. Device recharging circuitry 109 is coupled to power source 106, and may be configured to receive electrical energy induced in antenna 110 by one or more electromagnetic fields imposed on antenna 110, and to regulate and provide a level of energy to power source 106 for the purpose of recharging power source 106 and/or to provide the electrical energy to operate IMD 100.

Device recharging circuit 109 may perform various energy conditioning functions to the energy inductively generated in antenna 110, for example by providing rectification, voltage level regulation, current level regulation, and/or other signal processing functions in order to generate the "recharging energy" provided to power source 106. Thus, IMD 100 may be configured to couple electromagnetic energy captured by an antenna (including, but not necessarily the telemetry antenna), directed into a suitable rectifying circuit that delivers the electrical energy to an energy storage device such as a rechargeable battery. A switch 111 may be included in IMD 100 that is controlled to select whether the telemetry or the power recharge system is active, and whether antenna 110 is coupled to the communication circuitry 105 or the device recharging circuit 109. In other examples, a second antenna 112 is coupled to device recharging circuitry 109, and is configured to receive inductively coupled energy provided to antenna 112, and to provide the inductively coupled energy to device recharging circuit 109 to recharge power source 106.

In the illustrated example, IMD 100 includes processing circuitry 101 and an associated memory 102, sensing circuitry 103, therapy delivery circuitry 104, one or more sensors 107, and the communication circuitry 105 coupled to antenna 110 as described above. However, IMD 100 need not include all of these components, or may include additional components. For example, IMD 100 may not include therapy delivery circuitry 104 in some examples. Memory 102 may include computer-readable instructions that, when executed by processing circuitry 101, causes IMD 100 and processing circuitry 101 to perform various functions attributed to IMD 100 and processing circuitry 101 herein (e.g., sensing cardiac signals associated with cardiac activity of a patient, analyzing the sensed cardiac signals to detect any noise signals present within the sensed cardiac signals, providing an alarm output signal indicative of the detection of a noise signal within the sensed cardiac signals, and/or reconfiguring the parameters, including the electrodes 114, that are being used for sensing the cardiac signals, and/or for use in delivering stimulation therapy to the patient based on the detected noise signals).

Memory 102 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital or analog media. Memory 102 may store threshold(s) for time of day, posture, heart rate, activity level, respiration rate, noise signal threshold values, baseline amplitude values, and other parameters that may be associated with analysis of cardiac signals. Memory 102 may also store data indicating cardiovascular pressure measurements.

Processing circuitry 101 may include fixed function circuitry and/or programmable processing circuitry. Processing circuitry 101 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 101 may include multiple components, such as any combination of one or more microprocessors, one or more controllers, one or more DSPs, one or more ASICs, or one or more FPGAs, as well as other discrete or integrated logic circuitry. The functions attributed to processing circuitry 101 herein may be embodied as software, firmware, hardware or any combination thereof.

As shown in FIG. 8, sensing circuitry 103 and therapy delivery circuitry 104 are coupled to electrodes 114. Electrodes 114 may correspond to, for example, electrodes located on leads 58 and 59 of IMD 52 (FIG. 5), proximal electrode 64 and distal electrode 66 of IMD 54 (FIGS. 5 and 6), or electrodes 90 and 91 of IMD 56 (FIGS. 5 and 7). Sensing circuitry 103 may monitor signals from a selected two or more of electrodes 114 in order to monitor electrical activity of heart, impedance, or some other electrical phenomenon. In some of examples, at least one of electrodes 114 is a housing electrode formed on or from the housing of the IMD. 100. Sensing of a cardiac electrical signal may be done to determine heart rates or heart rate variability, or to detect arrhythmias (e.g., tachyarrhythmias or bradycardia) or other electrical signals. In some examples, sensing circuitry 103 may include one or more filters and amplifiers for filtering and amplifying a signal received from electrodes 114. In some examples, sensing circuitry 103 may sense or detect physiological parameters, such as heart rate, blood pressure, respiration, and other physiological parameters associated with a patient.

The resulting cardiac electrical signal may be passed to cardiac event detection circuitry, e.g., included as part of sensing circuitry 103, that detects a cardiac event when the cardiac electrical signal crosses a sensing threshold. The cardiac event detection circuitry may include a rectifier, filter and/or amplifier, a sense amplifier, comparator, and/or analog-to-digital converter. The cardiac event detection circuitry may further detect the presence of noise signal(s) on the sensed cardiac signal, and further process these signals to prevent the detected noise signal(s) from generating false-positive indications for example with respect to a cardiac event, such as an asystole, in the patient being monitored by IMD 100. Sensing circuitry 103 may output an indication to processing circuitry 101 in response to sensing of a cardiac event (e.g., detected P-waves or R-waves), and perform analysis of the sensed cardiac signal, including outputting an alarm output signal indicative of the detection of a noise signal on any of the sensed cardiac signals.

In this manner, processing circuitry 101 may receive detected cardiac event signals corresponding to the occurrence of detected R-waves and P-waves in the respective chambers of heart. Indications of detected R-waves and P-waves may be used for detecting ventricular and/or atrial tachyarrhythmia episodes, e.g., ventricular or atrial fibrillation episodes. Some detection channels may be configured to detect cardiac events, such as P- or R-waves, and provide indications of the occurrences of such events to processing circuitry 101, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Sensing circuitry 103 may also include a switch module to select which of the available electrodes 114 (or electrode polarities) are used to sense the heart activity. In examples with several electrodes 114, processing circuitry 101 may select the electrodes that function as sense electrodes, i.e., select the sensing configuration, via the switch module within sensing circuitry 103. Sensing circuitry 103 may also pass one or more digitized EGM signals to processing circuitry 101 for analysis, e.g., for use in cardiac rhythm discrimination, and/or for analysis to determine if noise signal(s) are present within the cardiac signals. The switch module may be controllable, for example based on commands issued by processing circuitry 101, to reconfigure which electrodes 114 are to be used to sense cardiac signal in response to a detection of noise signal(s) on one or more of the cardiac signals being sensed using electrodes 114. The switch module may also be controllable to reconfigure which of electrodes 114 are to be used to sense cardiac signal and/or to apply any stimulation therapy to the patient based on the detection of noise signal(s) in one or more of the cardiac signals being sensed using electrodes 114.

In the example of FIG. 8, IMD 100 includes one or more sensors 107 coupled to sensing circuitry 103. Although illustrated in FIG. 8 as included within IMD 100, one or more of sensors 107 may be external to IMD 100, e.g., coupled to IMD 100 via one or more leads, or configured to wirelessly communicate with IMD 100. In some examples, sensors 107 transduce a signal indicative of a patient parameter, which may be amplified, filtered, or otherwise processed by sensing circuitry 103. In such examples, processing circuitry 101 determines values of patient parameters based on the signals. In some examples, sensors 107 determine the patient parameter values, and communicate them, e.g., via a wired or wireless connection, to processing circuitry 101.

In some examples, sensors 107 include one or more accelerometers 108, e.g., one or more three-axis accelerometers. Signals generated by the one or more accelerometers 108 may be indicative of, as examples, gross body movement (e.g., activity) of the patient, patient posture, heart sounds or other vibrations or movement associated with the beating of the heart, or coughing, rales, or other respiration abnormalities. Accelerometers 108 may produce and transmit signals to processing circuitry 101 for a determination as to the posture of the patient. In various examples, signals from the accelerometers 108 are processed to determine an activity, such as when the patient is taking a step or steps or for example when the patient is running, that is used to provide an activity count associated with patient initiated physical activity of the patient. In some examples, sensors 107 may include sensors configured to transduce signals indicative of blood flow, oxygen saturation of blood, or patient temperature, and processing circuitry 101 may determine patient parameters values based on these signals.

In some examples, processing circuitry 101 determines one or more patient parameter values based on pressure signals. Patient parameter values determined based on pressure may include, as examples, systolic or diastolic pressure values, such as pulmonary artery diastolic pressure values. In some examples, a separate device such as sensor circuits include one or more sensors and sensing circuitry configured to generate a pressure signal, and processing circuitry 101 determines patient parameter values related to blood pressure based on information received from IMD 100.

Therapy delivery circuitry 104 is configured to generate and deliver electrical therapy to the heart. Therapy delivery circuitry 104 may include one or more pulse generators, capacitors, and/or other components capable of generating and/or storing energy to deliver as pacing therapy, defibrillation therapy, cardioversion therapy, other therapy or a combination of therapies. In some instances, therapy delivery circuitry 104 may include a first set of components configured to provide pacing therapy and a second set of components configured to provide anti-tachyarrhythmia shock therapy. In other instances, therapy delivery circuitry 104 may utilize the same set of components to provide both pacing and anti-tachyarrhythmia shock therapy. In still other instances, therapy delivery circuitry 104 may share some of the pacing and shock therapy components while using other components solely for pacing or shock delivery.

Therapy delivery circuitry 104 may include charging circuitry, one or more charge storage devices, such as one or more capacitors, and switching circuitry that controls when the capacitor(s) are discharged to electrodes 114 and the widths of pulses. Charging of capacitors to a programmed pulse amplitude and discharging of the capacitors for a programmed pulse width may be performed by therapy delivery circuitry 104 according to control signals received from processing circuitry 101, which are provided by processing circuitry 101 according to parameters stored in memory 102. Processing circuitry 101 controls therapy delivery circuitry 104 to deliver the generated therapy to the heart via one or more combinations of electrodes 114, e.g., according to parameters stored in memory 102. Therapy delivery circuitry 104 may include switch circuitry to select which of the available electrodes 114 are used to deliver the therapy, e.g., as controlled by processing circuitry 101. Processing circuitry 101 may further control and/or modify the therapy that is being or that may potentially be delivered by therapy delivery circuitry 104 based on the detection of a noise signal or noise signals in the sensed cardiac signals sensed by sensing circuitry 103 of IMD 100. In some examples, processing circuitry 101 may further control and/or modify the therapy that is being or that may potentially be delivered by therapy delivery circuitry 104 based on analysis of data corresponding to sensed cardiac signals sensed by another device, such as another IMD, and/or based on receiving an indication of an alarm output signal generated by another device that has detected a noise signal in sensed cardiac signal(s) associated with cardiac activity in the same patient where IMD 100 has been implanted.

Communication circuitry 105 includes any suitable hardware, firmware, software or any combination thereof for communicating with another device, such as an external device 60 and/or transceiver 53 as shown in FIG. 5, or another IMD. Under the control of processing circuitry 101, communication circuitry 105 may receive downlink telemetry from and send uplink telemetry to an external device 60 or another device that may be internal and/or external to IMD 100. In some examples, communication circuitry 105 may communicate with a local external device, for example through transceiver 53, and processing circuitry 101 may communicate with a networked computing device via the local external device and a computer network, such as the Medtronic® CareLink® Network developed by Medtronic, plc, of Dublin, Ireland. In some examples (i.e. where a single antenna is used) the antenna signal can be switched from the telemetry communication circuitry to the recharge circuit. In other examples, the recharge antenna/coil is separate from the communication/telemetry antenna. For example, antenna 110 may be switched between being coupled to communication circuitry 105 and device recharging circuitry 109 by switch 111, wherein switch 111 may be controlled by processing circuitry 101 to determine when antenna 110 is coupled to the communication circuitry 105 and when antenna 110 is to be coupled to the device recharging circuitry 109.

A clinician or other user may retrieve data from IMD 100 using an external device or another local or networked computing device configured to communicate with processing circuitry 101 via communication circuitry 105, for example through a transceiver such as transceiver 53. The clinician may also program parameters of IMD 100 using an external device or another local or networked computing devices. In some examples, the clinician may select patient parameters used to determine times of day and target activity levels to determine when to trigger taking cardiovascular pressure measurements.

In various examples, processing circuitry 101 is configured to receive signals from sensing circuitry 103, sensors 107, and/or sensor signals provided by sensors external to IMD 100, to process these sensor signals to generate one or more input parameters based either directly on or derived from the sensor signals. The input parameters are associated with current value(s) for one or more physiological parameters associated with a patient, such as patient 12. The physiological parameters associated with the input parameters may include activity counts, respiration rates, breathing rates, movements, postures, and changes in postures associated with a patient. The current values associated with these input parameters can be values measured directly from the input parameters, or derived for these input parameters. For example, a value of a heartrate, measured for example in heartbeats per minute or cardiac cycle length, may be determined as the current value (e.g., the most recent value) for the input parameter associated with the heart rate of the patient measured over some predefined time period. Similarly, a value of a breathing rate, measured for example in breaths per minute or breathing cycle length, may be determined as the current value (e.g., the most recent value) for the input parameter associated with the breathing rate of the patient as measured over some predefined time period. Similarly, current values can be determined for other input parameters, such as activity count (e.g., based on movement of the patient measured for example in steps taken by the patient per minute), body temperature, and for example a current value for a posture of the patient (e.g., lying down, standing, sitting). A current value of a physiological parameter may be, in some examples, a mean or median of measured values over a period of time.

In any of these instances, processing circuitry 101 may be configured to perform analysis of the data corresponding to sensed cardiac signals, and to detect the presence of a noise signal or noise signals occurring within the analyzed signals. Processing circuitry 101 may be further configured to perform one or more of the functions and to provide one or more of the features associated with the detection of a noise signal as described throughout this disclosure, including generation of an alarm output signal, reconfiguring of the sensing electrodes 114, and/or modification of the therapy being provided and/or potentially provided by therapy delivery circuitry 104 of IMD 100, based on the detection of the noise signal or signals.

Figure 9:
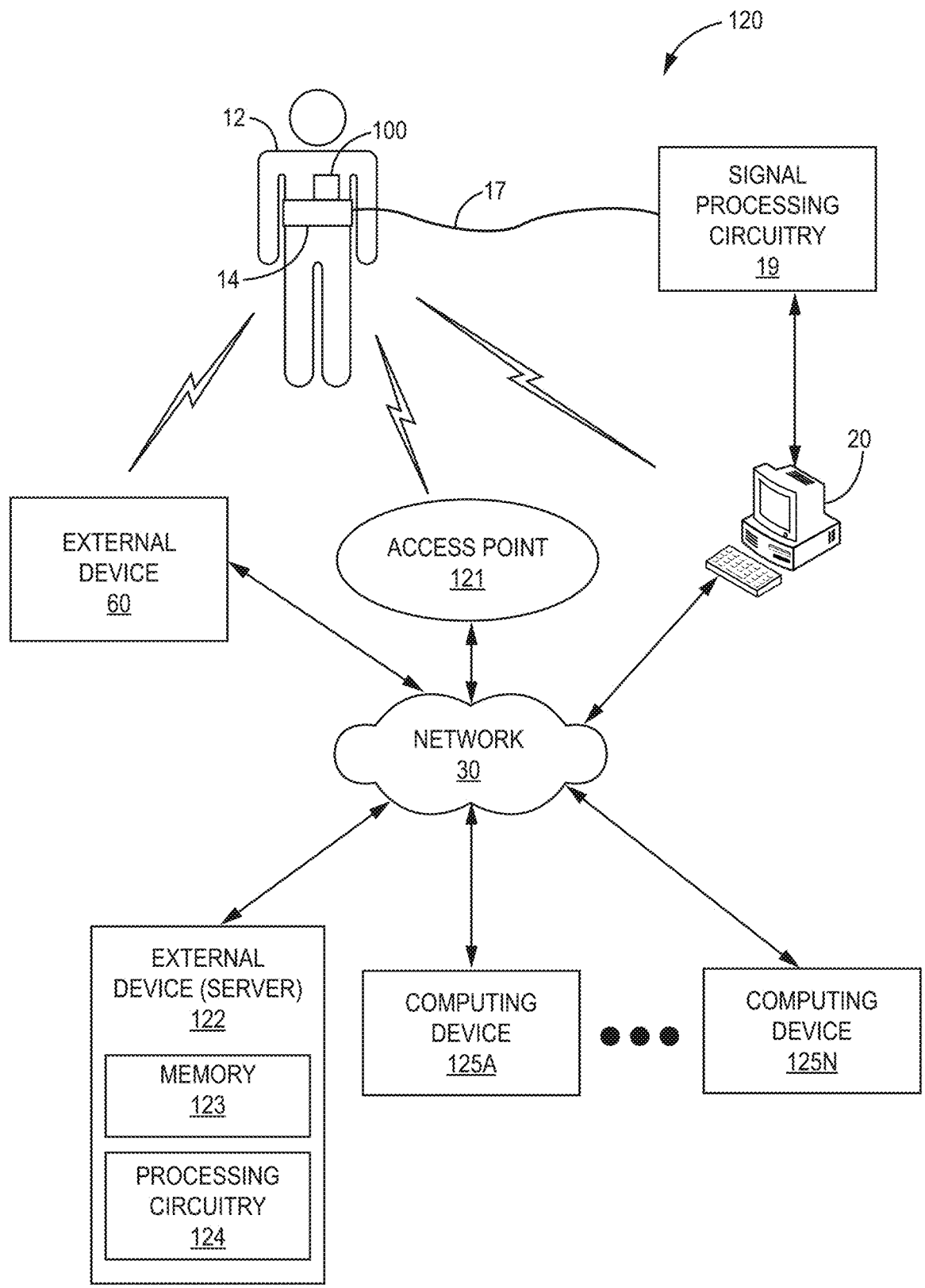
FIG. 9 is a functional block diagram illustrating an example medical device system according to various examples described in this disclosure.

FIG. 9 is a functional block diagram illustrating an example medical device system 120 according to various examples described in this disclosure. As shown in FIG. 9, a patient 12 may be coupled to an electrode apparatus 14, such as any of the electrode apparatuses illustrated and described with respect to FIGS. 1-3, which includes electrodes configured to sense cardiac signals associated with cardiac activity of patient 12. As shown in FIG. 9, electrode apparatus 14 may be electrically coupled, for example via wired connection 17, to signal processing circuitry 19, and to computing apparatus 20. Electrode apparatus 14 may be configured to monitor cardiac signals associated with patient 12 through the electrodes included with electrode apparatus 14, and to provide one or more sensed cardiac signals to signal processing circuitry 19 and computing apparatus 20. In some examples, signal processing circuitry 19 may be a device that is separate from computing apparatus 20, and in other examples signal processing circuitry 19 may be incorporated within computing apparatus 20.

Signal processing circuitry 19 and computing apparatus 20 may be arranged to provide any of the features and to perform any of the functions ascribed to these devices throughout this disclosure, including but not limited to receiving, processing, and analyzing sensed cardiac signals using any of the techniques described to detect noise signals in the received cardiac signals as described herein, and any equivalents thereof. Computing apparatus 20 may be configured to display graphical information related to the sensed cardiac signals on a display device included with computing apparatus 20, and to provide graphical information related to the detection of one or more noise signals detected in the cardiac signals. In some examples, computing apparatus 20 may be configured to reject signals provided by electrode apparatus 14, and/or reconfigure which electrodes of electrode apparatus 14 are to be used for further monitoring of cardiac signals with respect to patient 12 based on the detection of one or more noise signals within the sensed cardiac signals being provided to computing apparatus 20 by electrode apparatus 14.

As also shown in FIG. 9, a patient 12 may have an IMD 100 implant that is configured to monitor cardiac activity of patient 12, and to generate sensed cardiac signals corresponding to cardiac activity of the patient. IMD 100 includes electrodes, such as any of the electrodes illustrated and described with respect to IMDs 52, 54, or 56 in FIGS. 5-7, or electrodes 114 as illustrated and described with respect to IMD 100 in FIG. 8. The electrodes of IMD 100 as shown in FIG. 9 may be configured to sense cardiac signals associated with cardiac activity of patient 12.

IMD 100 as illustrated in FIG. 9 may provide any of the features and may be configured to perform any of the functions ascribed to the IMD devices described throughout this disclosure, and any equivalents thereof, including but not limited to receiving, processing, and analyzing sensed cardiac signals using any of the techniques, and the equivalents thereof, as described herein to detect noise signals in the received cardiac signals. In various examples, IMD 100 is configured to transmit data related to the sensed cardiac signals to one or more external devices, such as external device 60 and/or to other external devices through access point 121. In some examples, these external devices perform the analysis of the sensed cardiac signals to determine if a noise signal is present within the sensed cardiac signals. These external devices may, in response to a detection of a noise signal within the sensed cardiac signals, generate an alarm output signal indicative of the detection of the noise signal or noise signals. An indication of the detection of a noise signal or noise signals may be provided as an output provided as a graphical display on a display device coupled to one or more of the external devices.

Computing apparatus 20 may be configured to display graphical information related to the sensed cardiac signal on a display device included with computing apparatus 20, and to provide graphical information related to the detection of one or more noise signals detected in the cardiac signals. In some examples, computing apparatus 20 may be configured to reject signals provided by electrode apparatus 14, and/or reconfigure which electrodes of electrode apparatus 14 are to be used for further monitoring of cardiac signals with respect to patient 12 based on the detection of one or more noise signals within the sensed cardiac signals being provided to computing apparatus 20 by electrode apparatus 14.

System 120 further includes external computing devices, such as a server 122, and one or more other computing devices 125A-125N, that may be coupled to IMD 100, and external device 60 via a network 30. In this example, IMD 100 may use its communication circuitry to, e.g., at different times and/or in different locations or settings, communicate with external device 60 via a first wireless connection, and to communicate with an access point 121 via a second wireless connection. In the example of FIG. 9, computing apparatus 20, access point 121, external device 60, server 122, and computing devices 125A-125N are interconnected, and able to communicate with each other, through network 30.

Access point 121 may comprise a device that connects to network 30 via any of a variety of connections, such as telephone dial-up, digital subscriber line (DSL), or cable modem connections. In other examples, access point 121 may be coupled to network 30 through different forms of connections, including wired or wireless connections. In some examples, access point 121 may be co-located with the patient. Access point 121 may interrogate IMD 100, e.g., periodically or in response to a command from the patient or network 30, to retrieve physiological measurements and/or other operational or patient data from IMD 100. Access point 121 may provide the retrieved data to server 122 via network 30. In various examples, access point 121 may be any example of transceiver 53 described above.

In some examples, server 122 may be configured to provide a secure storage site for data that has been collected from IMD 100, and/or from external device 60. In some cases, server 122 may assemble data in web pages or other documents for viewing by trained professionals, such as clinicians, via computing devices 125A-125N. The illustrated system of FIG. 9 may be implemented, in some aspects, with general network technology and functionality similar to that provided by the Medtronic® CareLink® Network developed by Medtronic plc, of Dublin, Ireland.

In some examples, one or more of access point 121, server 122, and/or computing devices 125A-125N may be configured to perform, e.g., may include processing circuitry configured to perform, some or all of the techniques described herein, e.g., with respect to processing circuitry 101 of IMD 100 and external device 60, relating to detection of noise signals occurring within sensed cardiac signals. In the example system 120 as shown in FIG. 9, server 122 includes a memory 123 to store physiological and other data received from IMD 100 and/or external device 60, and processing circuitry 124, which may be configured to provide some or all of the functionality ascribed to processing circuitry of IMD 100 and/or computing device 20 as described herein. For example, processing circuitry 124 provide programming and/or parameters that are used to detect noise signals occurring within the sensed cardiac signals being sensed by IMD 100 and/or using electrode apparatus 14.

Figure 10A:
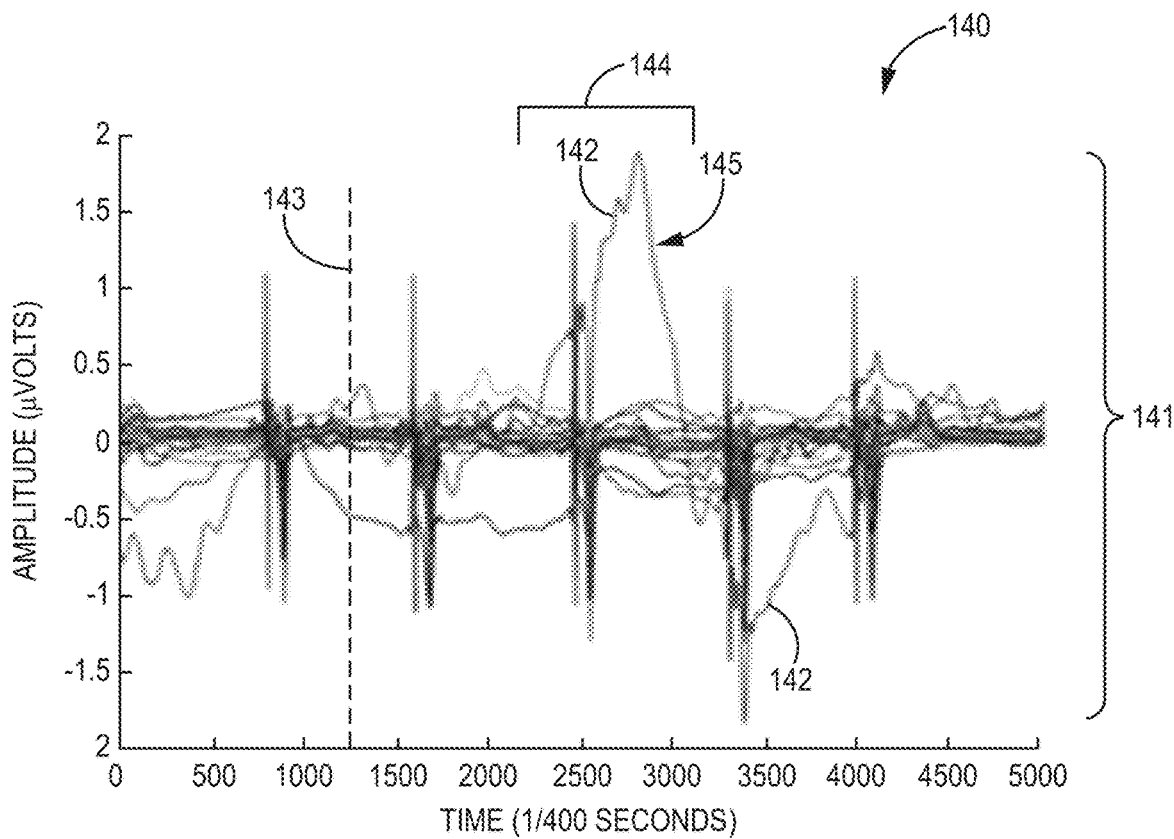
FIG. 10A includes a graphical illustration of illustrative waveforms including low frequency noise.

FIG. 10A includes a graphical illustration 140 of illustrative waveforms including low frequency noise. Graphical illustration 140 includes a plurality of waveforms 141, each waveform representative of a sensed cardiac signal. The plurality of waveforms 141 are plotted against a vertical axis representative of the amplitude of the waveforms in microvolts (μV) over time in seconds, time as represented by the horizontal axis in graphical illustration 140. Each of the plurality of waveforms 141 as depicted in graphical illustration 140 are superimposed on each other so that each point in each of the individual waveforms 141 along any vertical line, such as vertical line 143, represents the voltage levels for each individual waveform at the particular time indicated at that vertical line.

In various examples, each of the illustrative waveforms 141 may be representative of a sensed voltage level, e.g., a cardiac signal, that was sensed between a particular set of two electrodes configured to monitor electrical activity associated with cardiac activity of a patient. For example, each of the waveforms 141 illustrated in graphical illustration 140 may be representative of a sensed voltage that was sensed between two of a plurality of electrodes, such as any two of electrodes 16 as shown in FIGS. 1-3, or any of the electrodes of IMDs 52, 54, 56, or 100 as shown in FIGS. 5-8. As shown in FIG. 10A, at some point in time the particular waveform 142 of the plurality of waveforms 141 includes a positive voltage spike 145 occurring during the time period generally indicated by time span 144. Using one or more of the techniques described in this disclosure, waveform 142 may be analyzed to determine whether the positive voltage spike 145 is caused by a noise signal. In some examples, using the techniques described herein allows an analysis of waveform 142 to determine that the positive voltage spike 145 is a noise signal, for example caused by loss of contact between the patient being monitored and at least one of the electrodes providing the signal being sensed as waveform 142.

A determination that the positive voltage spike 145 in waveform 142 is a noise signal may be used to further process the signals represented by waveforms 141 using any of the techniques described herein, including rejecting waveform 142 by removing waveform 142 from the plurality of waveforms 141 being analyzed to determine the condition of the patient, or for example to prevent a false-positive indication of a cardiac event, such as asystole, occurring in the patient. In some examples, a determination that waveform 142 includes a noise signal may be used to determine one or more alternative pairs of electrodes to be used for further monitoring and/or for therapy treatments with respect to the patient being monitored, thus eliminating possible false indication and/or unnecessary alteration of a therapy treatment based on improper analysis of the cardiac signals represented by waveforms 141.

Figure 10B:
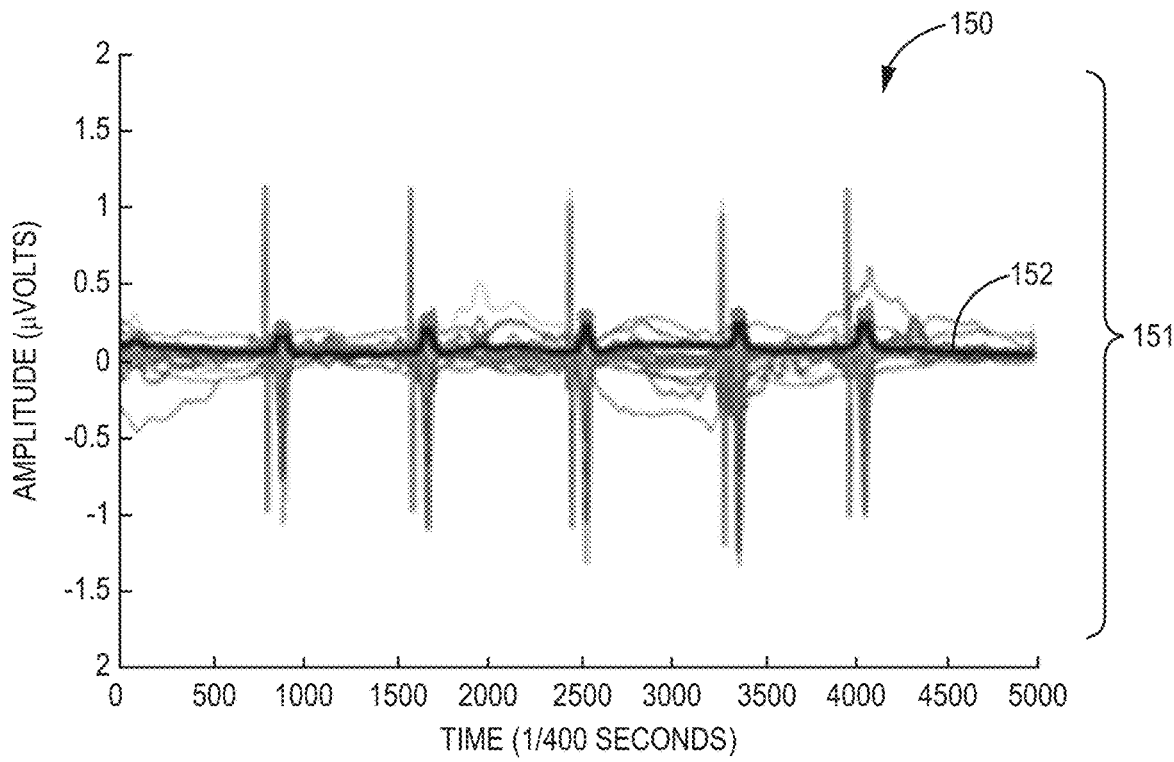
FIG. 10B includes a graphical illustration of illustrative waveforms analyzed and processed according to one or more example techniques described in this disclosure.

FIG. 10B includes a graphical illustration 150 of illustrative waveforms 151 analyzed and processed according to one or more example techniques described in this disclosure. The graphical illustration of the plurality of waveforms 151 as shown in graphical illustration 150 depicts the plurality of waveforms 141 from graphical illustration 140 having waveform 142 removed. In some examples, a determination that waveform 142 as described above with respect to graphical illustration 140 includes a noise signal may result in further processing of the waveforms 141 to generate the plurality of waveforms 151 as shown in graphical illustration 150 in FIG. 10B. In various examples, with the removal of waveform 142 from the plurality of waveforms 151, the further processing of the plurality of waveforms 151 may be performed to generate additional information, such as generation of waveform 152 representative of a mean or median value of the combination of the plurality of waveforms included in waveforms 151. With the noise signal present in waveform 142 removed from the calculations used to determine waveform 152, further analysis of waveform 152 may be performed, for example to determine the condition of a patient being monitored or to evaluate the efficacy of treatment being administered to the patient without the possible corruption that the noise signal from waveform 142 may cause.

Figure 11A:
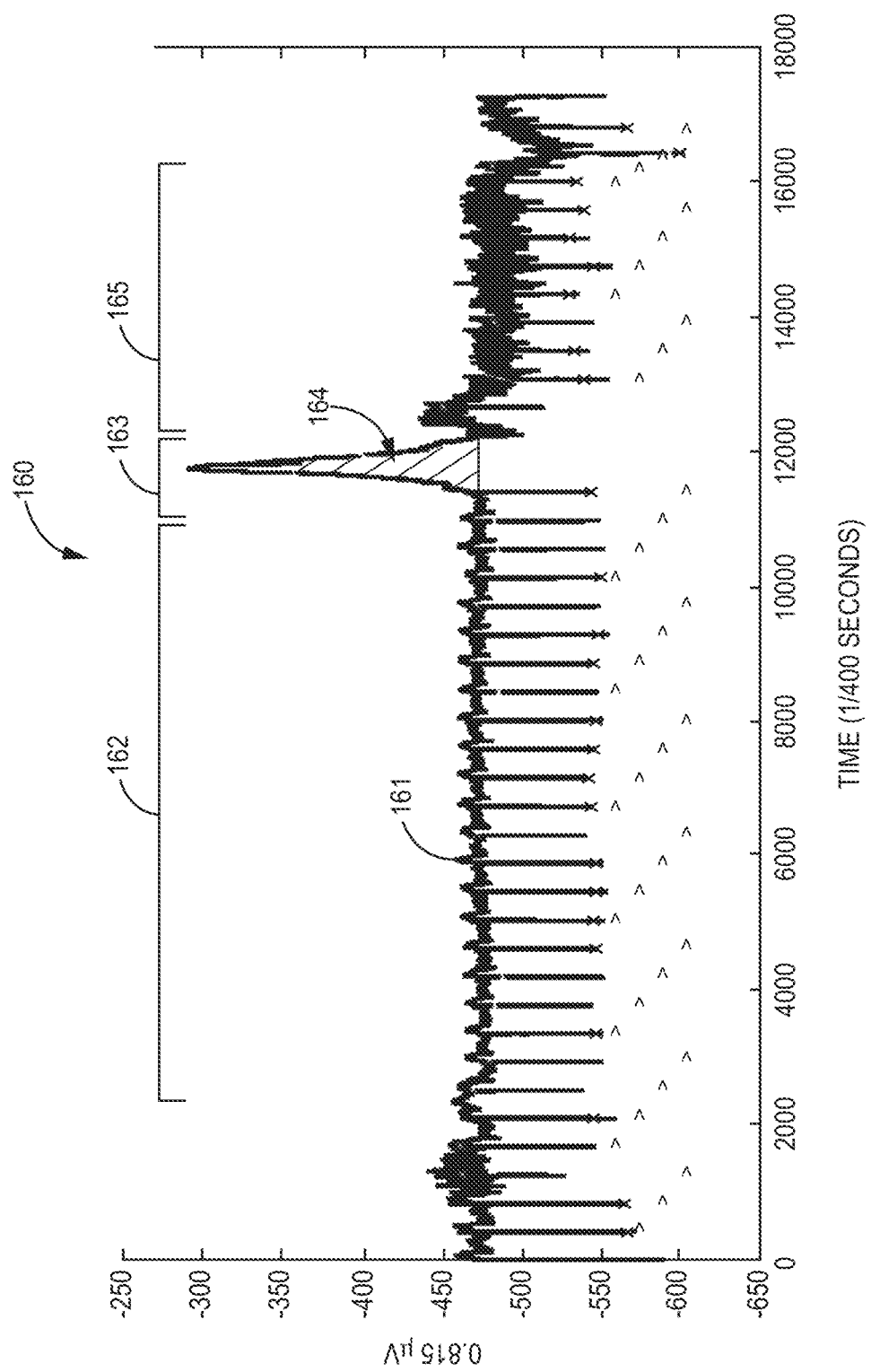
FIG. 11A includes a graphical illustration of an illustrative waveform according to various techniques described in this disclosure.

FIG. 11A includes a graphical illustration 160 of an illustrative waveform 161 according to various techniques described in this disclosure. Graphical illustration 160 includes a single waveform 161 representative of a sensed cardiac signal. Waveform 161 is plotted against a vertical axis representative of the amplitude of the waveform in μVolts, over time in seconds, time represented by the horizontal axis in graphical illustration 160. As shown in graphical illustration 160, over the time span generally indicated by bracket 162, waveform 161 includes a somewhat consistent pattern of peaks and variations in amplitude that is repeated at a relatively consistent interval in time. During the time span generally indicated by bracket 163 in graphical illustration 160, waveform 161 does not continue to provide the consistent pattern previously provided during the time span indicated by bracket 162, but instead provides a large positive voltage spike 164 having an amplitude and a duration that is much larger than any of the peaks provided in waveform 161 during the time span indicated by bracket 162.

Figure 11B:
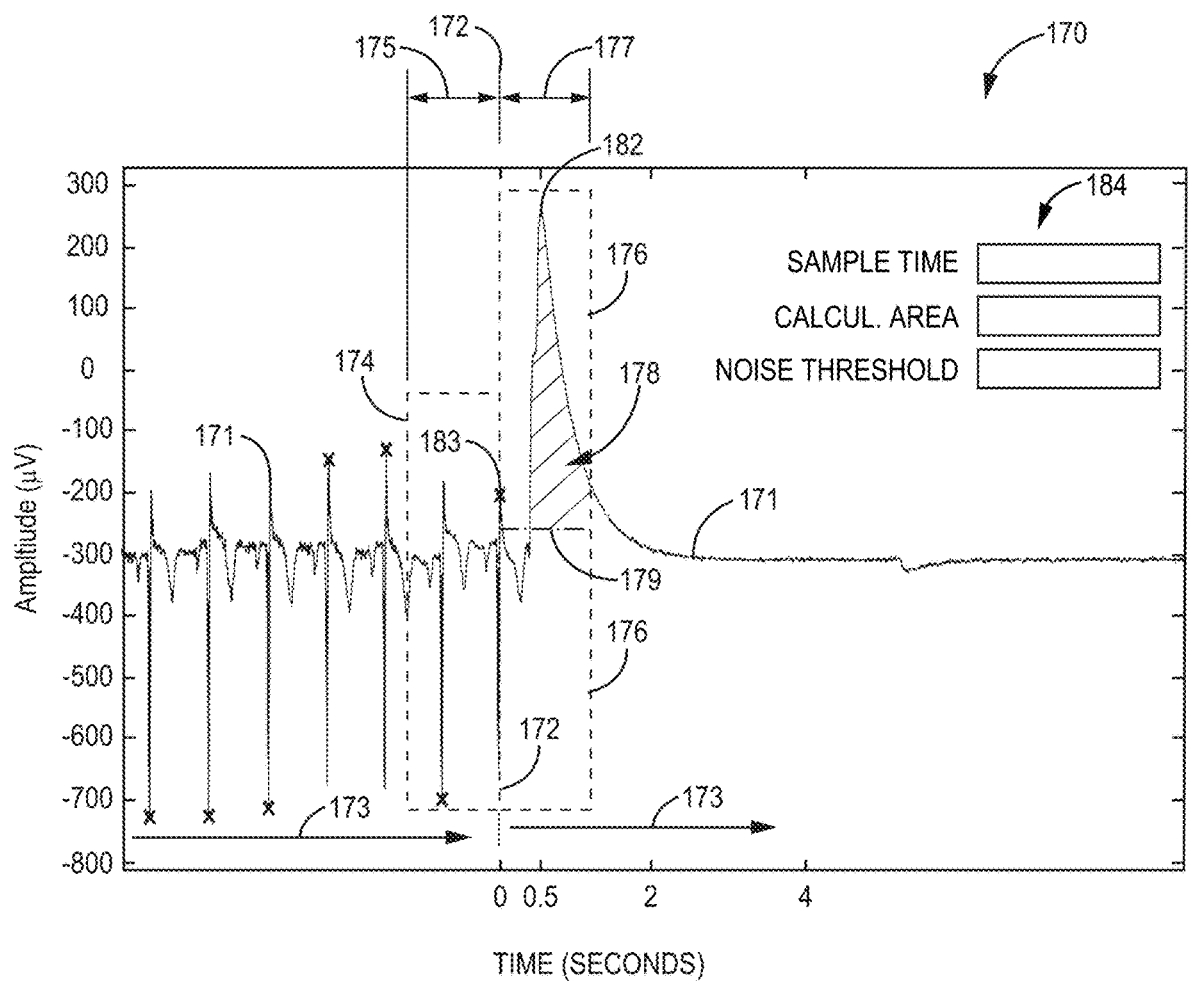
FIG. 11B includes a graphical illustration of an illustrative waveform and a set of detection windows used to detect a noise signal according to various techniques described in this disclosure.
Figure 11C:
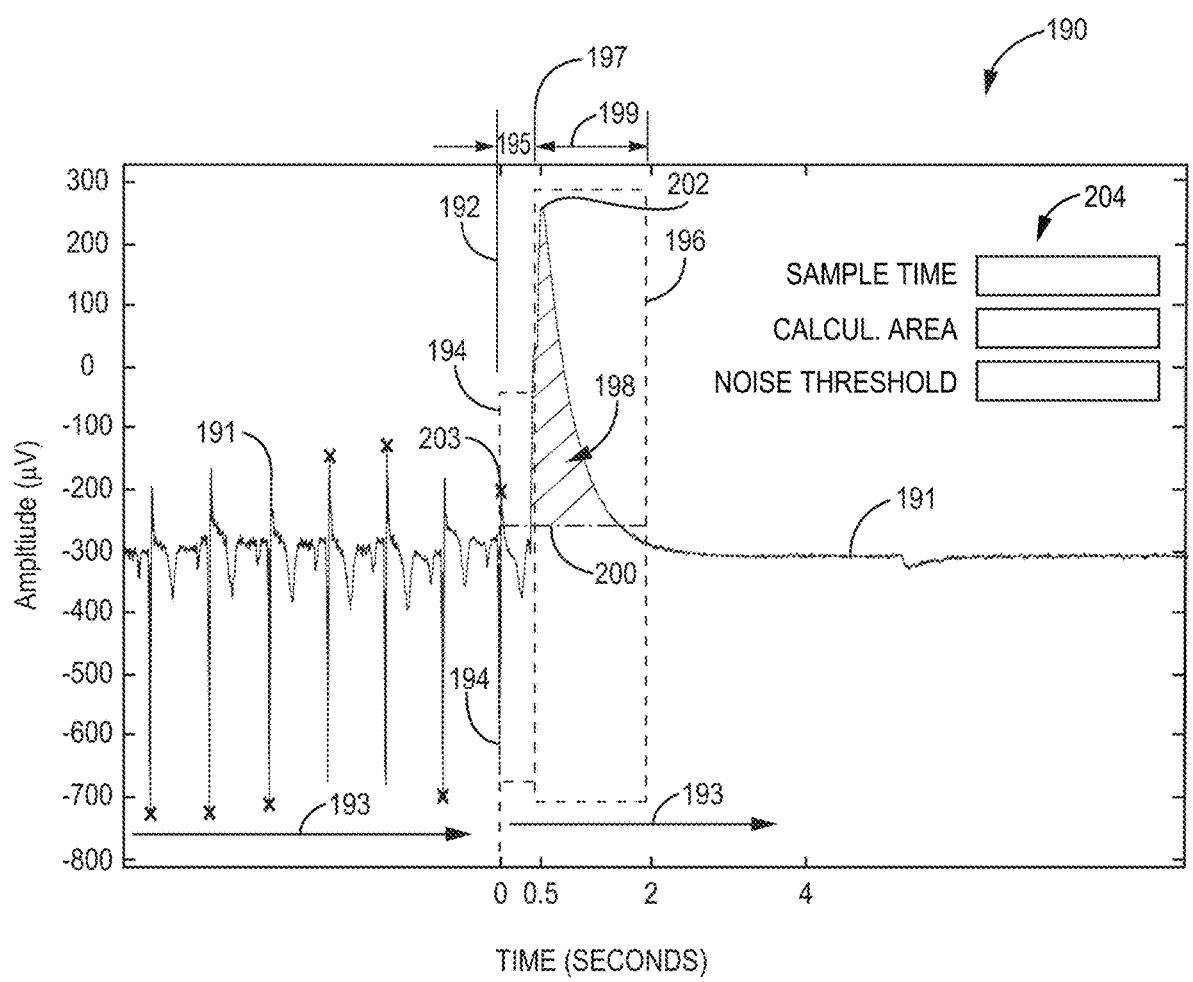
FIG. 11C includes a graphical illustration of an illustrative waveform and a set of detection windows used to detect a noise signal according to various techniques described in this disclosure.
Figure 11D:
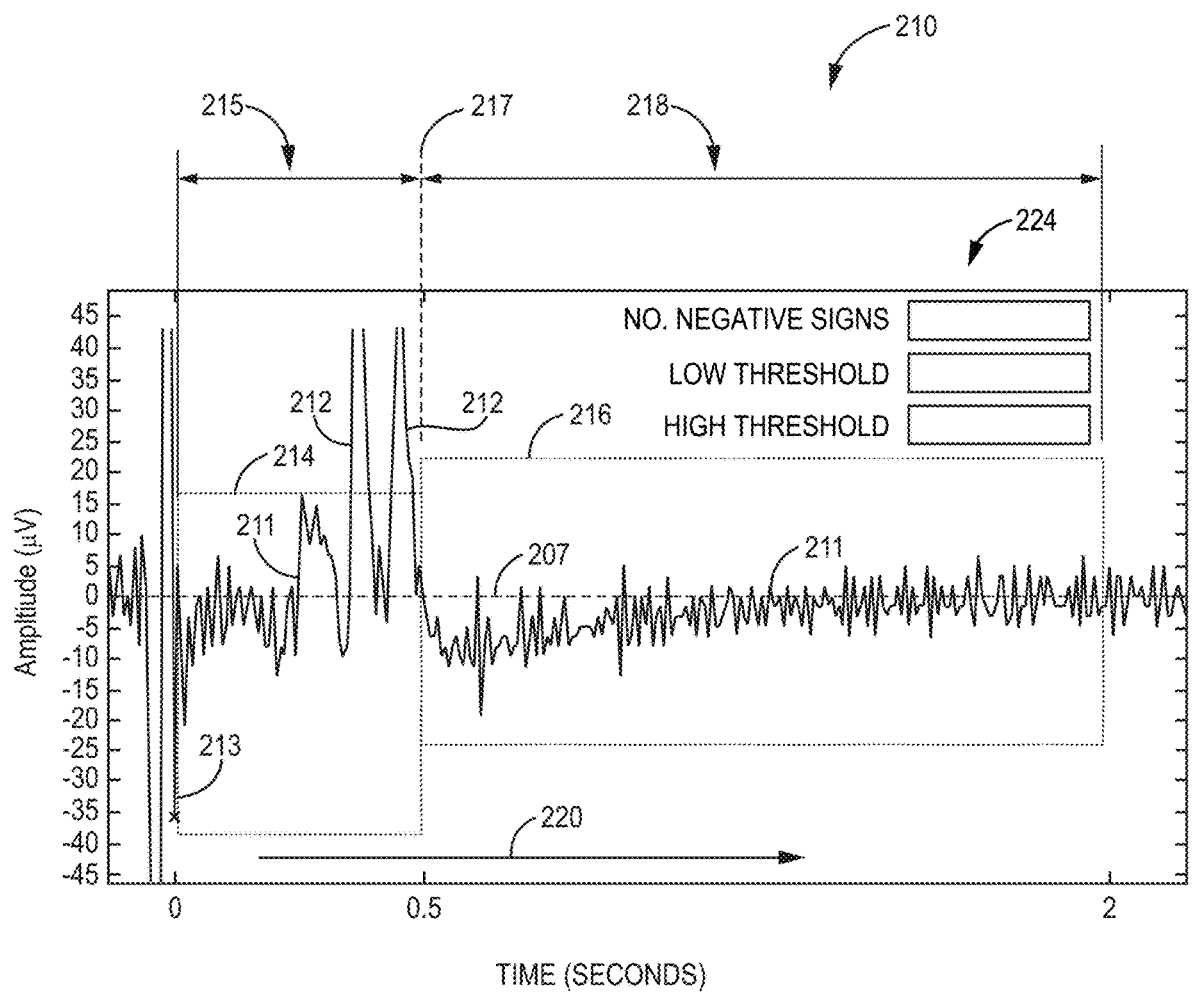
FIG. 11D includes a graphical illustration of an illustrative waveform and a set of detection windows used to detect a noise signal according to various techniques described in this disclosure.

Following the positive voltage spike 164 occurring in waveform 161, and during the time span generally indicated by bracket 165 in graphical illustration 160, waveform 161 provides a waveform that includes a larger variation in the amplitude of the signal, and may include more negative peaks and/or a lower overall average or median voltage value compared to these same parameters if measured over the time span indicated by bracket 162 for waveform 161. In various examples, the positive voltage spike occurring in waveform 161 during the time span indicated by bracket 163 and/or the variations in waveform 161 illustrated during the time span indicated by bracket 165 following the positive voltage spike 164 may be analyzed to determine if these portions of the waveform 161 are representative of a noise signal. Analysis of waveform 161 to determine if waveform 161 includes a noise signal may be used to further control sensing of the waveforms being monitored as cardiac activity of a patient, and/or or to further evaluate and/or control of therapy treatment(s) being provided to the patient. FIGS. 11B, 11C, and 11D provide further examples of techniques that may be used to analyze a cardiac signal to detect the presence of a noise signal within a sensed cardiac signal.

FIG. 11B includes a graphical illustration 170 of an illustrative waveform 171 and a set of detection windows 174, 176 used to detect a noise signal according to various techniques described in this disclosure. Waveform 171 is plotted against a vertical axis representative of amplitude of the waveform in μVolts, over time in seconds, time represented by the horizontal axis in graphical illustration 170. As shown in graphical illustration 170, waveform 171 includes a positive voltage spike 182 in the portion of waveform 171 following the time indicated as "0" (zero) seconds in graphical illustration 170. Using a set of detection windows, for example as illustratively represented by detection windows 174 and 176 in graphical illustration 170, one or more portions of waveform 171 may be analyzed to determine if waveform 171 includes a noise signal, such as the positive voltage spike 182.

In various examples, the process of analyzing waveform 171 to determine if a noise signal is present in the waveform includes determining a sample time 172 as a basis for setting detection windows 174 and 176. In various examples, determining a sample time comprises setting the sample time equal to a time where an R-wave has been detected within waveform 171. For example, as shown in graphical illustration 170 a sample time 172 is selected based on detection of an R-wave 183 represented in waveform 171. In some examples, determining a sample time can occur based on the detection of each R-wave, or based on the detection so some "N" number of R-waves wherein "N" is a positive integer, or the detection of the first or the "Nth" R-wave following some predefined time interval. Once a sample time 172 is selected, a first detection window 174 is set so that the first detection window includes a time span 175 extending from sample time 172 and for some amount of time prior to sample time 172. The width of time span 175 is not limited to any particular time span, and in some examples may be a time span in a range of 0.5 to 5 seconds. As shown in graphical illustration 170, the first detection window 174 extends from sample time 172 and comprises an illustrative time span 175 of approximately 1 second in width, extending to include the portion of waveform 171 ranging from sample time 172 to a time up to 1 second prior to sample time 172.

In various examples, a voltage value, referred to as a baseline amplitude value, which is associated with sample time 172 and the first detection window 174 is calculated. The value for the baseline amplitude value may be calculated by sampling the voltage values for waveform 171 that fall within the first detection window 174 at some sampling rate, and for example determining the value for the baseline voltage based on these sampled voltage values. In some examples, the value for the baseline voltage may be calculated by calculating an average of the voltage values of waveform 171 sampled during the first detection window 174. In some examples, the value for the baseline voltage may be calculated as the median value for the voltage values of waveform 171 sampled during the first detection window 174.

In addition to setting the first detection window once a sample time 172 has been selected, a second detection window 176 is also set so that the second detection window 176 includes a time span 177 extending from sample time 172 and for some amount of time following the sample time 172. The width of time span 177 is not limited to any particular time span, and in some examples, may be a time span in a range of 0.5 to 5 seconds. As shown in graphical illustration 170, the second detection window 176 extends from sample time 172 and includes an illustrative time span 177 of approximately 1 second in width, extending to include the portion of waveform 171 ranging from sample time 172 to a time up to one second subsequent to sample time 172. In various examples, the width of time span 177 for the second detection window 176 is equal to the width of time span 175 set for the first detention window 174 associated with a same sample time, e.g., sample time 172. However, examples of setting the widths for the first detection window and the second detection window are not limited to setting detection windows to include a same width or time span, and in some examples the width of the first detection window may be different from the width set for the second detection window associated with a same sample time. The widths of time span 175 and time span 177 may be programable values that may be set by a user, such as a physician.

Following setting of the second detection window 176 associated with sample time 172, a voltage value for the portion of waveform 171 falling within the second detection window 176 may be calculated by sampling the voltage values for waveform 171 that fall within the second detection window 176 at some sampling rate, and determining an area-under-the-curve value for the portion of waveform 171 based on these sampled voltage values. In some examples, the sampling rate used to sample the voltage values for the portion of waveform 171 that falls within the second detection window 176 is a same sampling rate as was used to sample the voltage values for the portions of waveform 171 that fell within the first detection window 174. In some examples, the calculation used to calculate the baseline amplitude value, e.g., using average or median to calculate the baseline voltage level for the sampled voltages of waveform 171 that fell within the first detection window is also used to calculate the voltage value of the waveform 171 for the second detection window 176.

Once the first detection window 174 and the second detection window 176 have been set for sample time 172, an area-under-the-curve value associated with this same sample time 172 may be calculated based on a sampled set of difference values measured between the voltage value of waveform 171 falling within the second detection window and the determined baseline amplitude value associated with the first detection window 174. By way of illustration, a baseline amplitude value associated with waveform 171 and the first detection window 174 may be represented by the horizontal dashed line 179 imposed across the second detection window 176 at a voltage level equivalent to the determined baseline amplitude value. A determination of the area-under-the-curve value may be made by calculating the area 178 that is included below the portion of waveform 171 that falls within the second detection window 176 and is above the baseline amplitude value represented by horizontal dashed line 179. The area-under-the-curve value associated with area 178 is indicated in FIG. 11B by the cross-hatched area shown within the second detection window. Calculation of the area-under-the-curve value is not limited to any particular technique for calculating this area, and may include any technique for calculating an area under a curve, as would be understood by one of ordinary skill in the art.

Once an area-under-the-curve value has been calculated for area 178, the calculated value may be compared to a noise signal threshold value. In some examples, if the area-under-the-curve value that has been calculated for area 178 exceeds the noise signal threshold value, a determination is made that a noise signal has been detected within waveform 171, and further, that the noise signal may be associated with the portion of waveform 171 just subsequent to sample time 172 of waveform 171. The detection of a noise signal associated with waveform 171 my cause a system performing the analysis and/or detecting of the noise signal, such as processing circuitry associated with computing apparatus 20 and/or associated with any of the implantable medical devices described throughout this disclosure, to generate an alarm output signal that indicates that a noise signal has been detected within the sensed cardiac signal associated with waveform 171. The alarm output signal may be further processed to control further sensing and/or application of therapy to a patient according to any of the techniques described in this disclosure associated with the detection of a noise signal within a sensed cardiac signal.

Outputting an alarm output signal may include providing some type of graphical indication on a display device, such as a graphical depiction as illustrated in FIG. 11B, provided as a display on a computer monitor or other display device. In some examples, the graphical display may utilize colors and/or other visual cues, such as flashing portion of the display, to indicate the detection of the noise signal. For example, the portion of the waveform 171 as shown in FIG. 11B included within the second detection window may be provided in a different color, for example red, compared to other portions of waveform 171, to indicate that the portion of the waveform within the second detection window 176 includes a detected noise signal. In some examples, the dashed box representing the second detection window 176 in graphical illustration 170 may be provided as a flashing element (e.g., flashing on and off) to direct attention to the portion of the waveform 171 detected as a noise signal. In some examples, the graphical display may provide textual information 184 in addition to the display of the waveform 171, which may also include display of the detection windows 174, 176. Textual information 184 is not limited to any particular type of information, and may include numerical values provide in text fields. Text fields may include fields labeled as "Sample Time," "Calcul. Area," and "Noise Threshold," as illustrated in FIG. 11B. The numerical value provided in the text field labeled "Sample Time" may correspond to the sample time indicated by dashed line 172, the numerical value provided in the text field labeled "Calcul. Area" may correspond to a calculated area-under-the-curve value for area 178, and the numerical value provided in the text field labeled "Noise Threshold" may correspond to the noise signal threshold value used in the comparison of the calculated area-under-the-curve to determine if area 178 comprises a noise signal. In various examples, a display of the waveform 171 may be provided regardless of whether the portion of the waveform 171 being analyzed and displayed includes or does not include a detected noise signal. In some examples, the detection of a noise signal in waveform 171 is not displayed to a user, thus avoiding a potential indication of a false asystole detection, and thereby lowing the review burden on a caregiver, such as a nurse or physician.

As shown in graphical illustration 170, first detection window 174 and second detection window 176 are associated with a sample time 172, and may be used to determine whether waveform 171 includes a noise signal in a portion of waveform 171 included within the second detection window 176. In various examples, detection of noise signals included in waveform 171 may be provided in association with a plurality of sample times along waveform 171, as illustratively represented by arrows 173. In various examples, the plurality of sample times may be selected based on a repetitive interval of sample times, e.g., a sample rate, wherein a sample time is set for each of the times indicated by the repetitive time interval indicated by the sample rate. For example, sample times may be set at a time interval using a preset time span, such as one second, wherein a sample time is set for each of a plurality of sample times spaced apart at a one second time interval to form a series of sample times spaced apart from one another based on the preset time span of the time interval. The preset time span in not limited to any particular time span, and in some examples, may be within a predefined range of 0.1 to 5 seconds. Using a one second time interval as an example, a plurality of sample times may be set, each sample time spaced one second apart in time and following the time that was set for the previous sample time. In other examples, the sample times may be selected based on detection of a particular event associated with waveform 171.

For example, a sample time may be selected based on the detection of an R-wave occurring in waveform 171. In some examples, a sample time may be selected based on the detection of each event, e.g., each detection of an R-wave occurring within waveform 171. In other examples, a sample time may be selected based on the occurrence of a number "N" of occurrences of a particular event, wherein N may be a positive integer. For example, a sample time may be selected based on the detection of some number "N," for example three consecutive occurrences of R-waves detected in waveform 171. Upon detection of the Nth occurrence of the event being detected within waveform 171, a sample time may be set, and subsequent sample times may be set at each further detection of next Nth occurrence of the event.

In this manner, a series of samples times may be set relative to time along waveform 171. In some examples, for each of the selected sample times, a first detection window and a second detection window may be set that are associated with the particular sample time, in a similar manner as described above with respect to sample time 172, first detection window 174, and second detection window 176. For each of the selected sample times and detection widows associated with the sample times, analysis of the portion of waveform 171 that falls within the particular detection windows may be performed using any of the techniques described above for detection windows 174, 176 to determine if waveform 171 includes a noise signal. In other words, the sequential time samples may be used to form a sliding or moving set of detection window, wherein each set of detection windows may be analyzed to determine if a noise signal exists within the portion of waveform 171 being analyzed with that respective set of detection windows. Based on the spacing in time set between the sample times and the time spans set for the detection windows, the detection windows associated with a given sample time may or may not overlap with the detection windows associated with other sample times that may be set either before, and/or after the time set for the given sample time. Following a determination that a noise signal has been detected in waveform 171 using any of the sample times and associated detection windows, any of the further processes associated with detection of a noise signal as described throughout this disclosure may be performed. In this manner, analysis of a waveform associated with sensing a cardiac signal may be performed on a continuous basis over time and at some pre-determined sample rate, or based on events occurring within the waveform, for one or more cardiac signal being sensed in association with a patient.

FIG. 11C includes a graphical illustration 190 of an illustrative waveform 191 and a set of detection windows 194, 196 used to detect a noise signal according to various techniques described in this disclosure. In graphical illustration 190, waveform 191 is plotted against a vertical axis representative of amplitude of the waveform in μVolts, over time in seconds, time represented by the horizontal axis. As shown in graphical illustration 190, waveform 191 includes a positive voltage spike 202 in the area of waveform 191 beginning at approximately the time indicated as "0.5" seconds along the horizontal axis in graphical illustration 190. Using a detection window, for example as illustratively represented by second detection window 196 in graphical illustration 190, portions of waveform 191 may be analyzed to determine if waveform 191 includes a noise signal represented as the positive voltage spike 202.

In various examples, the process of analyzing waveform 191 to determine if a noise signal is present in the waveform includes determining a sample time 192 as a basis for setting first detection window 194 and second detection window 196. In various examples, determining a sample time comprises setting the sample time based on a portion of waveform 191 where an R-wave has been detected within the waveform. For example, as shown in graphical illustration 190, a sample time 192 is selected based on detection of an R-wave 203 represented in waveform 191. Once a sample time 192 is selected, a first detection window 194 is set so that the first detection window includes a time span 195 extending from sample time 192 and for some amount of time following sample time 192. The width of time span 195 is not limited to any particular time span, and in some examples, may be a time span in a range of 0.1 to 0.5 seconds. As shown in graphical illustration 190, the first detection window extends from sample time 192 and comprises an illustrative time span 195 of approximately 0.5 seconds in width, extending to include the portion of waveform 191 ranging from sample time 192 to a time 0.5 seconds subsequent to sample time 192. The time span 195 included within the first detection window 194 may be referred to as a "blanking period" following the sample time 192.

In a manner similar to any of the techniques described above with respect to first detection window 174 and time span 175 as illustrated in FIG. 11B, a baseline amplitude value may be calculated based on the voltage values of waveform 191 that falls within first detection window 194 as illustrated in FIG. 11C. The calculated value for the baseline voltage may be used to set a level for a baseline amplitude value in the second detection window 196, as indicated by dashed horizontal line 200 in FIG. 11C. As shown in FIG. 11C, the second detection window 196 is set to begin at the end of time span 195 (indicated by vertical line 197) and extends from the end of time span 195 for a time span 199, ending at the end of time span 199. Time span 199 is not limited to a particular span of time and may include a time span ranging from 0.5 to 5 seconds. Once the second detection window including time span 199 has been set, a determination for the area-under-the-curve value may be made by calculating the area 198 that is included below the portion of waveform 191 that falls within the second detection window 196 and that is above the baseline amplitude value represented by horizontal dashed line 200. The area-under-the-curve value associated with area 198 is indicated in FIG. 11C by the cross-hatched area shown within the second detection window. Calculation of the area-under-the-curve value is not limited to any particular technique for calculating this area, and may include any technique for calculating an area under a curve, as would be understood by one of ordinary skill in the art.

Once an area-under-the-curve value has been calculated for area 198, the calculated value may be compared to a noise signal threshold value. In some examples, if the area-under-the-curve value that has been calculated for area 198 exceeds the noise signal threshold value, a determination is made that a noise signal has been detected within waveform 191, and further, that the noise signal may be associated with the portion of waveform 191 that falls at least partially within the second detection window 196. The detection of a noise signal associated with waveform 191 my cause a system performing the analysis and/or detecting the noise signal, such as processing circuitry associated with computing apparatus 20 and/or associated with any of the implantable medical devices described throughout this disclosure, to generate an alarm output signal that indicates that a noise signal has been detected within the sensed cardiac signal associated with waveform 191. The alarm output signal may be further processed to control further sensing and/or application of therapy to a patient according to any of the techniques described in this disclosure associated with the detection of a noise signal within a sensed cardiac signal.

In a manner similar to that described above with respect to graphical illustration 170 and FIG. 11B, outputting an alarm output signal with respect to the analysis performed as illustrated by graphical illustration 190 and FIG. 11C as may include providing some type of graphical indication on a display device, such a graphical depiction illustrated in FIG. 11C, provided as a display on a computer monitor or other display device. In some examples, the graphical display may utilize colors and/or other visual cues, such as flashing portion of the display, to indicate the detection of the noise signal. For example, the portion of the waveform 191 as shown in FIG. 11C included within the detection window 196 may be provided in a different color, for example red, compared to other portions of waveform 191 to indicate that the portion of the waveform within the detection window includes a detected noise signal. In some examples, the dashed box representing the detection window 196 in graphical illustration 190 may be provided as a flashing element (e.g., flashing on and off) to direct attention to the portion of the waveform 171 detected as a noise signal. In some examples, the graphical display may provide textual information 204 in addition to the display of the waveform 191, the textual information comprising information related to waveform 191 and the detection of a noise signal within waveform 191 according to any of the examples described above with respect to textual information 204. In various examples, a display of the waveform 191 as illustrated in FIG. 11C may be provided regardless of whether the portion of the waveform 191 being analyzed and displayed includes or does not include a detected noise signal. In some examples, the detection of a noise signal in waveform 191 is not displayed to a user, thus avoiding a potential indication of a false asystole detection, and thereby lowing the review burden on a caregiver, such as a nurse or physician.

In a manner similar to that described above with respect to FIG. 11B, the first detection window 194 and the second detection window 196 as illustrated and described with respect to FIG. 11C may be one of a set of sliding or moving detection windows that are set at various intervals along waveform 191, as depicted by arrows 193. These sliding or moving detection windows may be set for example based on any of the techniques described above with respect to first detection window 174 and second detection window 176, for example based the detection of a sensed R-wave, or based on some predefined time interval. In this manner, the techniques for detection of a noise signal within a waveform as illustrated and described above with respect to waveform 191 and graphical illustration 190 may be used for analysis of a waveform associated with sensing a cardiac signal performed on a continuous basis over time and at some pre-determined sample rate, or based on events occurring within the waveform, for one or more cardiac signal being sensed in association with a patient.

FIG. 11D includes a graphical illustration 210 of an illustrative waveform 211 and a set of detection windows 214, 216 used to detect a noise signal according to various techniques described in this disclosure. Waveform 211 is plotted against a vertical axis representative of amplitude of the waveform in µVolts, over time in seconds, time represented by the horizontal axis in graphical illustration 210. In contrast to the waveforms shown in FIGS. 11A-11C, which depict the actual voltage level variations of a sensed cardiac signal, waveform 211 as illustrated in FIG. 11D represents a difference signal having voltage values corresponding to a sensed cardiac signal. The values depicted for the difference signal used to form waveform 211 may be calculated by taking a voltage value for the sensed cardiac signal at time "y," and subtracting from that sensed voltage value the voltage value of the sensed cardiac signal at time "y−1", wherein time "y−1" is some time prior to time "y", and the difference in time between time "y" and "y−1" is some predetermined time, which may be based on a sample rate used to sample the voltage value of the cardiac signal used to form waveform 211. For example, a sample rate of 128 Hertz may be used to sample the voltage value for a sensed cardiac signal being analyzed for noise signals. Based on a sample rate of 128 Hertz, the difference between samples, i.e., the time span between the voltage sample at time "y" and voltage sample at time "y−1" would be 1/128 seconds, or approximately 0.0078 seconds. Sample rates used to sample the voltage level of the sensed cardiac signal used to generate the difference signal 211 are not limited to any particular sample rate and may be any sample rate deemed appropriate for sampling the voltage value of the cardiac signal for the purposes of detection of noise signals within the cardiac signal.

For each sampled voltage value for the cardiac signal (e.g., sampled voltage at time "y"), the sampled voltage value for the previously taken sample (e.g., sampled voltage at time "y−1") is subtracted from the next sampled voltage value to determine a value for waveform 211 at time "y." Waveform 211 as illustrated in graphical illustration 210 is an example of a waveform that may be calculated based on this difference signal calculation technique. As shown in FIG. 11D, some of the difference signal values within waveform 211 fall below a "zero" value line 207, and some of the signal values within waveform 211 fall above the "zero" value line 207. A noise signal, such as the positive voltage spikes 164 as illustrated in FIG. 11A, may result in a difference signal having one or more positive spikes, such as spikes 212, in the difference signal depicted by waveform 211 in FIG. 11D.

Referring still to FIG. 11D, a first detection window 214 may be set based on the detection of an event, such as sensing an R-wave, for example R-wave 213, within waveform 211. Based on the detection of R-wave 213, a first detection window 214 is set. First detection window 214 begins at the time of detection of R-wave 213, and extends over a time span 215, ending at the expiration of time span 215. As shown in FIG. 11D, time span 215 extends for a time period of 0.5 seconds. The time period included within time span 215 is not limited to any particular time span and may range from 0.2 to 1 second in some examples. At the expiration of time span 215, a second detection window 216 is set. The second detection window 216 begins at the time of expiration of time span 215, illustrated by vertical dashed line 217, and extends over time span 218, ending at the expiration of time span 218. As shown in FIG. 11D, time span 218 extends for a time period of 1.5 seconds. The time period included in time span 218 is not limited to any particular time span and may range from one to five seconds in some examples.

At the expiration of time span 218, a count of the number, the negative sampled values, negative signs, e.g., voltage values below the "zero" value line 207, may be taken and compared to the total number of samples for the voltages that were sampled within the second detection window 216. The number of negative signs may also be converted into a percentage of negative signs, or a ratio of negative signs occurring during second detection window 216 compared to the total number of samples taken during the second detection window. The calculated value (number, percentage, ratio) of negative signs may be tabulated as a quantization value and compared to one or more threshold values to determine if a noise signal is detected within waveform 211. For example, using some sampling rate, for example 128 Hertz, a set of samples of the voltage values of the portion of the waveform 211 that falls within the second detection window 216 are taken. For each sample taken, a determination is made as to whether the voltage value has a negative sign, that is, has a voltage value that falls below the "zero" value line 207. A count of the total samples that produce a negative sign may be divided by the total number of samples taken, and that value may be multiplied by 100% to obtain a percentage value of the number of samples within the second detection window 216 that have a negative sign. As similar calculation to be performed to determine for example a ratio of the number of negative signs compared to the total number of samples take could be made in the alternative. Regardless of whether a number of negative signs, a percentage of negative signs, or a ratio of negative signs, or some other measurement used, the results may be referred to as a quantification value, and that quantification value may be compared to the one or more threshold values for use in determining whether the portion of the cardiac signal being analyzed includes a noise signal.

In some examples, the calculated percentage of samples having a negative sign may be compared to one or more threshold percentage values to determine if the waveform 211 includes a noise signal. In some examples, if the percentage of negative signs determined for the waveform 211 within the second detection window 216 is less than a lower percentage threshold value, or is greater than an upper percentage threshold value, the waveform 211 may be determined to include a noise signal in the portion of waveform 211 included in the first detection window 214 and/or in the second detection window 216. A similar comparison could be performed by comparing a ratio of the number of negative signs within the second detection window 216 to the total number of samples taken to one or more threshold ratio values could be performed in the alternative. In some examples, instead of converting the number of negative signs to a percentage value, a simple count of the number of negative signs may be compared to a lower threshold value and to an upper threshold value. In these instances, if the number of negative signs counted within the second detection window 216 falls below the lower threshold value or exceeds the upper threshold value, the waveform 211 is considered to include a noise signal in the portion of the cardiac signal corresponding the portion of waveform 211 falling within the second detection window.

Although the above-described example refers to making a count or a determination of a quantification value associated with the second detection window 216 and waveform 211 based on negative signs, the determination of the quantification value is not limited to calculation based on use of negative signs. In various examples, the calculation of a quantification value may be based on some other criterion or set of criteria associated with the portion of waveform 211 included within a detection window such as detection window 216. For example, other alternatives that may be used to calculate the quantification value may include determining a number of positive sample values, determining a number of non-negative sample values (e.g., a count of zero sample values plus positive sample values) or a number of non-positive sample values (e.g., a count of zero sample values plus negative sample values).

The detection of a noise signal associated with waveform 211 may cause a system performing the analysis and/or detecting the noise signal, such as processing circuitry associated with computing apparatus 20 and/or associated with any of the implantable medical devices described throughout this disclosure, to generate an alarm output signal that indicates that a noise signal has been detected within the sensed cardiac signal corresponding to waveform 211. The alarm output signal may be further processed to control further sensing and/or application of therapy to a patient according to any of the techniques described in this disclosure associated with the detection of a noise signal within a sensed cardiac signal.

Outputting an alarm output signal may include providing some type of graphical indication on a display device, such a graphical depiction illustrated in FIG. 11D, provided as a display on a computer monitor or other display device. In some examples, the graphical display may utilize colors and/or other visual cues, such as flashing portion of the display, to indicate the detection of the noise signal. For example, the portion of the waveform 211 as shown in FIG. 11D included within the detection window 216 may be provided in a different color, for example red, compared to other portions of waveform 211 to indicate that the portion of the waveform within the detection window includes a detected noise signal. In some examples, the dashed box representing the detection window 216 in graphical illustration 210 may be provided as a flashing element (e.g., flashing on and off) to direct attention to the portion of the waveform 211 detected as a noise signal. In some examples, the graphical display may provide textual information 224 in addition to the display of the waveform 211, which may also include display of the detection window 216. Textual information 224 is not limited to any particular type of information and may include numerical values provide in text fields. Text fields may include fields labeled as "No. Negative Signs," "Low Threshold," and "High Threshold," as illustrated in FIG. 11D. The numerical value provided in the text field labeled "No. Negative Signs" may correspond to the number or percentage of negative signs falling within detection window 216, the numerical value provided in the text field labeled "Low Threshold" may correspond to a low threshold value, and the numerical value provided in the text field labeled "High Threshold" may correspond to the high threshold value used in the comparison of the number, percentage, or ratio of negative signs falling with the second detection window 216 used to determine if waveform 211 comprises a noise signal. In various examples, a display of the waveform 2111 may be provided regardless of whether the portion of the waveform 211 being analyzed and displayed includes or does not include a detected noise signal. In some examples, the detection of a noise signal in waveform 211 is not displayed to a user, thus avoiding a potential indication of a false asystole detection, and thereby lowing the review burden on a caregiver, such as a nurse or physician.

In a manner similar to that described above with respect to the detection windows of FIGS. 11B and 11C, detection windows 214, 216 as illustrated and described with respect to FIG. 11D may be provided as a sliding or moving set of detection windows, as illustratively represented by arrow 220, so that the position of detection windows 214, 216 may move along in time to different positions along waveform 211, providing a series of detection windows that may be set along waveform 211 relative to the time axis. The basis for setting each of the detection windows may be a triggering event, such as the detection of an R-wave within waveform 211 or may be set at some pre-determined and repetitive time interval. For each of the sets of detection windows, the difference signal represented by waveform 211 may be analyzed as described above to determine a number, a percentage, or a ratio of negative signs or other some particular criterion or set of criteria as described above that occur within the second detection window of the set of detection windows, and the resulting quantification value may be compared to the corresponding threshold values as described above with respect to detection windows 214, 216 to detect the presence of a noise signal within waveform 211.

By providing sets of moving or sliding detection windows relative to time along waveform 211, the difference signal represented by waveform 211 may be analyzed to detect noise signal present in the sensing cardiac signal on a continuous basis over time and at some pre-determined sample rate, or based on events occurring within the waveform, for one or more cardiac signal being sensed in association with a patient.

Figure 11E:
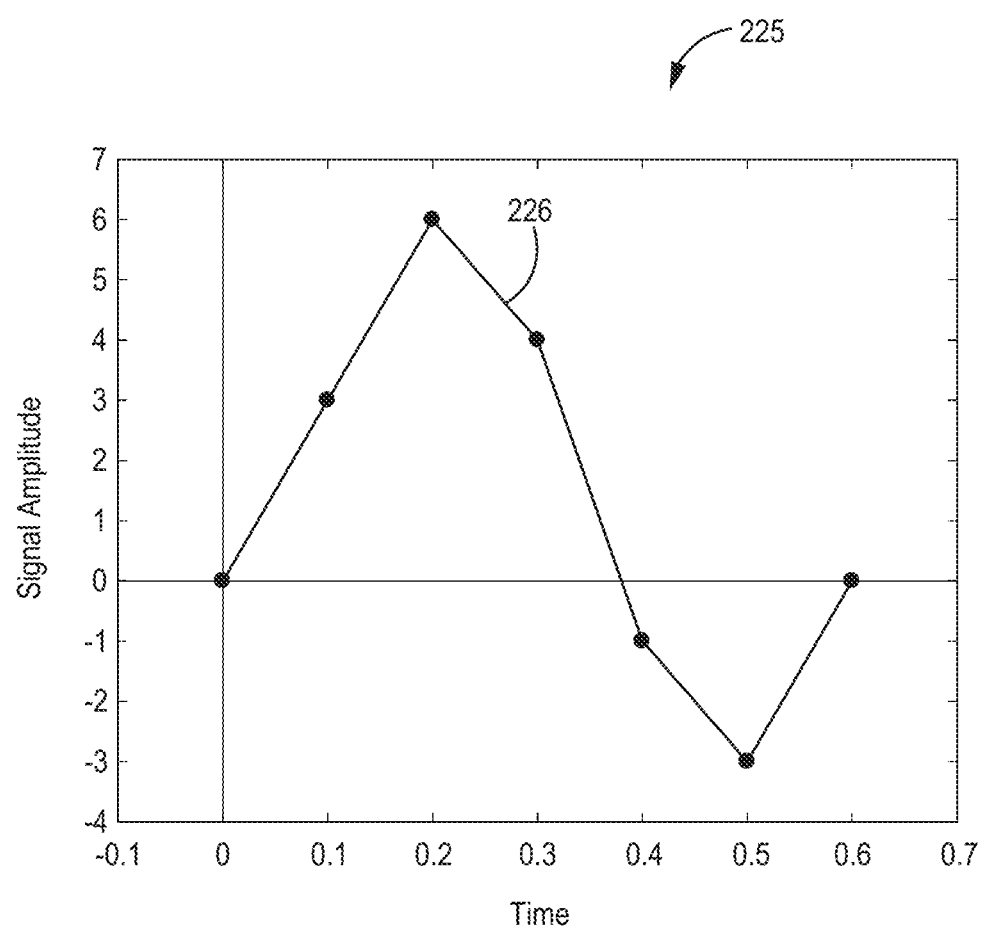
FIG. 11E includes a graphical illustration of sample data associated with a portion of a waveform according to various techniques described in this disclosure.
Figure 11F:
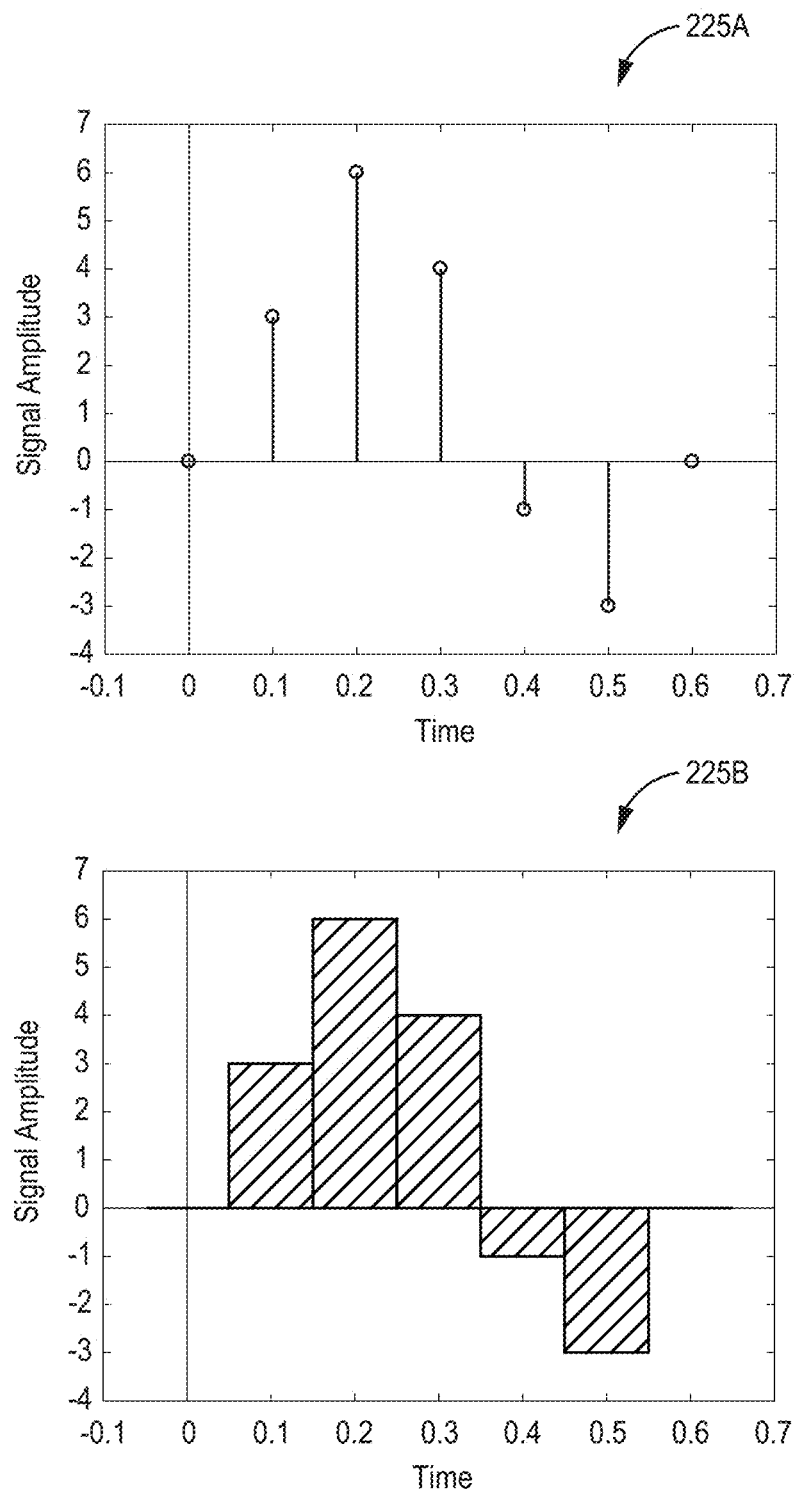
FIGS. 11F-11G include graphical illustrations of example techniques for calculating an area-under-the-curve corresponding to the sample data illustrated in FIG. 11E.
Figure 11G:
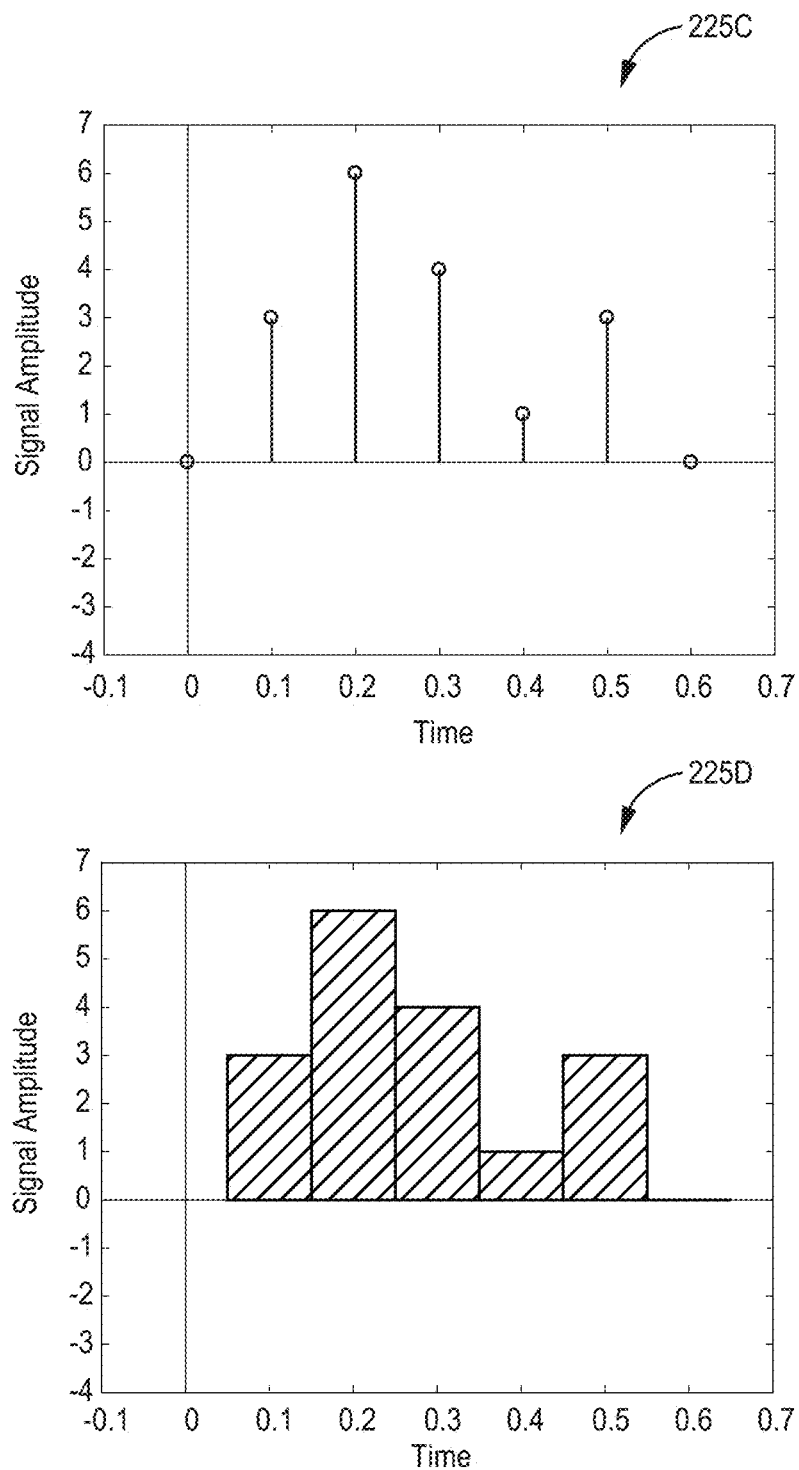

FIG. 11E includes a graphical illustration 225 of sample data associated with a portion of a waveform 226 according to various techniques described in this disclosure. As illustrated in graphical illustration 225, a series of data points associated with waveform 226 are taken at a sample times 0-0.6, represented along the horizontal axis representative of time. The vertical axis of graphical illustration 225 represents a set of nominal values, for example nominal voltage values for the waveform 226 at each of the sample times 0-0.6. In some examples, the waveform 226 may represent data sampled for a portion of a signal included within a detection window, as described above, having a width that extends from sample time "0" to sample time "0.7" as illustrated in graphical illustration 225. FIGS. 11F-11G include additional graphical illustrations illustrating example techniques for calculating an area-under-the-curve (AUC) value corresponding to the sample data and waveform 226 as illustrated in FIG. 11E.

FIG. 11F includes a graphical illustration 225A illustrating use of a sum of the signal amplitudes at the sampled times 0-0.6 as the basis for the AUC calculation associated with waveform 226. As shown in graphical illustration 225A, a value for the amplitude of waveform 226 of FIG. 11E is determined for each of the sample times 0-0.6. The value at each sample time is assigned a positive value if the sampled value at the sample time is positive (e.g., above the "0" value amplitude line), and is assigned a negative value if the sampled value is negative (e.g., below the "0" value amplitude line). Table 1 below is a summary of the signal values as depicted in graphical illustration 225A, having a row for each of the sample times.

TABLE 1

SUM OF THE SIGNAL AMPLITUDES

| Sample Time (horizontal-axis) | Amplitude (vertical-axis) | Calculated Amplitude |
|---|---|---|
| 0 | 0 | 0 |
| 0.1 | 3 | 3 |
| 0.2 | 6 | 6 |
| 0.3 | 4 | 4 |
| 0.4 | −1 | −1 |
| 0.5 | −3 | −3 |
| 0.6 | 0 | 0 |
| | AUC | 9 |

The first column in Table 1 includes a listing of each of the sample times 0-0.6, listing one sample time per row in the table. The second column of Table 1 includes a listing of an amplitude value for the waveform at the sample time for that corresponding row. The third column of Table 1 includes the calculated value for the amplitude for the corresponding sample time. The bottom row of the third column in Table 1 illustrates a value of "9," which is the sum of the calculated values for the amplitudes for each of the sample times included in the third column. The value "9" is illustrative of a value that may be calculated as the AUC value for the waveform 226 using the sum of the signal amplitudes technique illustrated by graphical illustration 225A for the waveform 226 sampled over sample times 0-0.6. This calculated AUC value may then be compared to a threshold value to determine whether the portion of the signal corresponding to waveform 226 as illustrated in graphical illustration 225A includes a noise signal. The value for the threshold used to compare with the calculated AUC values using this technique may be set to a value that would be exceeded for a noise signal when analyzing a signal using the particular technique illustrated by graphical illustration 225A and Table 1 for performing the AUC calculation.

FIG. 11F also includes a graphical illustration 225B illustrating use of a sum of the signal amplitudes with respect to sampling frequency at the sampled times 0-0.6 as the basis for the AUC calculation associated with waveform 226. As shown in graphical illustration 225B, a value for the amplitude of waveform 226 of FIG. 11E over the time period associated with the sampling frequency is determined for each of the sample times 0-0.6. The value at each sample time is assigned a positive value if the sample value at the sample time is positive (e.g., above the "0" value amplitude line), and is assigned a negative value if the sample value is negative (e.g., below the "0" value amplitude line). Table 2 below is a summary of the signal values as depicted in graphical illustration 225B, having a row for each of the sample times.

TABLE 2

SUM OF THE SIGNAL AMPLITUDES/SAMPLING FREQUENCY

| Sample Time (horizontal-axis) | Amplitude (vertical-axis) | Calculated Amplitude |
|---|---|---|
| 0.0 | 0 | 0 × 0.1 = 0 |
| 0.1 | 3 | 3 × 0.1 = 0.3 |
| 0.2 | 6 | 6 × 0.1 = 0.6 |
| 0.3 | 4 | 4 × 0.1 = 0.4 |
| 0.4 | −1 | −1 × 0.1 = −0.1 |
| 0.5 | −3 | −3 × 0.1 = −0.3 |
| 0.6 | 0 | 0 × 0.1 = 0 |
| | AUC | 0.9 |

The first column in Table 2 includes a listing of each of the sample times 0.1-0.7, having one sample time per row. The second column of Table 2 includes a listing an amplitude value for the waveform at the sample time for the corresponding row. The third column of Table 3 includes the calculated value for the amplitude value multiplied by the sampling time period (e.g., a time period of 0.1) for the corresponding sample time. The bottom row and third column in Table 2 illustrates a value of "0.9," which is the sum of the calculated values for the amplitudes for each of the calculated values included in the third column. The value "0.9" is illustrative of a value that is calculated as the AUC value for the signal 226 using the sum of the signal amplitudes based on sampling frequency technique illustrated by graphical illustration 225B for the waveform 226 sampled over sample times 0.1-0.7. This calculated AUC value may then be compared to a threshold value to determine whether the portion of the signal corresponding to waveform 226 as illustrated in graphical illustration 225 includes a noise signal as described herein. The value for the threshold used to compare the AUC value calculated using this technique may be set to a value that would be exceeded by a noise signal when analyzing a signal using the particular technique illustrated by graphical illustration 225B and Table 2 for performing the AUC calculation.

FIG. 11G includes a graphical illustration 225C illustrating use of a sum of the absolute values of the signal amplitudes at the sampled times 0-0.6 as the basis for the AUC calculation associated with signal 226. As shown in graphical illustration 225C, an absolute value for the amplitude of signal 226 of FIG. 11E is determined for each of the sample times 0-0.6. The absolute value at each sample time is assigned a positive value regardless of whether the actual sample value at the sample time is has positive or a negative value. Table 3 below is a summary of the signal values as depicted in graphical illustration 225C, having a row for each of the sample times.

TABLE 3

SUM OF THE ABSOLUTE VALUES OF THE SIGNAL AMPLITUDES

| Sample Time (horizontal-axis) | Amplitude (vertical-axis) | Calculated Amplitude |
|---|---|---|
| 0 | 0 | 0 |
| 0.1 | 3 | 3 |
| 0.2 | 6 | 6 |
| 0.3 | 4 | 4 |
| 0.4 | −1 | 1 |
| 0.5 | −3 | 3 |
| 0.6 | 0 | 0 |
| | AUC | 17 |

The first column in Table 3 including a listing of each of the sample times 0-0.6, having one sample time per row. The second column of Table 3 includes a listing an actual amplitude value for the waveform at the sample time for the corresponding row. The third column of Table 3 includes the calculated absolute value for the amplitude for the corresponding sample time. The bottom row and third column in Table 3 illustrates a value of "17," which is the sum of the calculated absolute values for the amplitudes for each of the sample times included in the third column. The value "17" is illustrative of a value that may be calculated as the AUC value for the signal 226 using the sum of the absolute values of the signal amplitudes as illustrated by graphical illustration 225C for the waveform 226 sampled over sample times 0-0.6. This calculated AUC value may then be compared to a threshold value to determine whether the portion of the signal corresponding to waveform 226 as illustrated in graphical illustration 225 includes a noise signal. The value for the threshold used to compare the AUC value calculated using this technique may be set to a value that would be exceeded by a noise signal when analyzing a signal using this particular technique illustrated by graphical illustration 225C and Table 3 for performing the AUC calculation.

FIG. 11G also includes a graphical illustration 225D illustrating use of a sum of the absolute value of the signal amplitudes with respect to sampling frequency at the sampled times 0.1-0.6 as the basis for the AUC calculation associated with waveform 226. As shown in graphical illustration 225D, an absolute value for the amplitude of waveform 226 of FIG. 11E over the time period associated with the sampling frequency is determined for each of the sample times 0.0-0.6. The value at each sample time is assigned a positive value regardless of whether the actual voltage value at the sample time over the is a positive value or is a negative value. Table 4 below is a summary of the signal values as depicted in graphical illustration 225D, having a row for each of the sample times.

TABLE 4

SUM OF THE ABSOLUTE VALUE OF THE SIGNAL AMPLITUDES/SAMPLING FREQUENCY

| Sample Time (horizontal-axis) | Amplitude (vertical-axis) | Calculated Amplitude |
|---|---|---|
| 0.0 | 0 | 0 × 0.1 = 0 |
| 0.1 | 3 | 3 × 0.1 = 0.3 |
| 0.2 | 6 | 6 × 0.1 = 0.6 |
| 0.3 | 4 | 4 × 0.1 = 0.4 |
| 0.4 | 1 | 1 × 0.1 = 0.1 |
| 0.5 | 3 | 3 × 0.1 = 0.3 |
| 0.6 | 0 | 0 × 0.1 = 0 |
| | AUC | 1.7 |

The first column in Table 4 includes a listing of each of the sample times 0.0-0.6, having one sample time per row. The second column of Table 4 includes a listing an absolute value for sampled value for the waveform at the sample time for the corresponding row. The third column of Table 3 includes the calculated value for the absolute value of the amplitude of the waveform at the sampled time multiplied by the sampling time period (e.g., a time period of 0.1) for the corresponding sample time. The bottom row and third column in Table 4 illustrates a value of "1.7," which is the sum of the calculated absolute values for the amplitudes/sampling time period for each of the calculated values included in the third column. The value "1.7" is illustrative of a value that is calculated as the AUC value for the signal 226 using the sum of the absolute values for the signal amplitudes based on a sampling frequency technique illustrated by graphical illustration 225D for the waveform 226 sampled over sample times 0.0-0.6. This calculated AUC value may then be compared to a threshold value to determine whether the portion of the signal corresponding to waveform 226 as illustrated in graphical illustration 225 includes a noise signal as described herein. The value for the threshold used to compare the AUC value calculated using this technique may be set to a value that would be exceeded by a noise signal when analyzing a signal using the particular technique illustrated by graphical illustration 225D and Table 4 for performing the AUC calculation.

Figure 12:
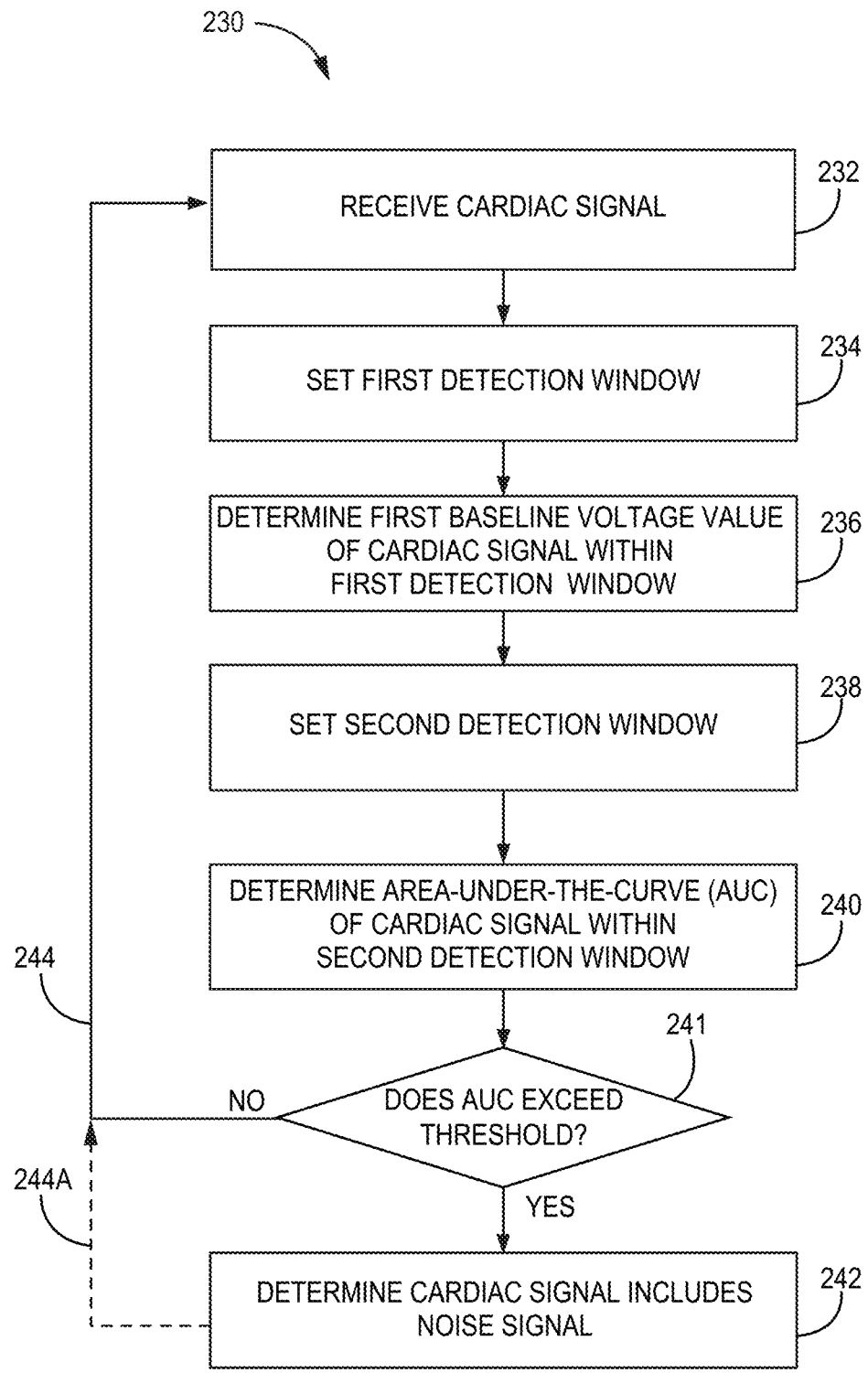
FIG. 12 illustrates a flowchart of a method according to various examples described in this disclosure.

FIG. 12 illustrates a flowchart illustrating a method 230 according to various examples described in this disclosure. Although method 230 is described with respect to the devices and systems illustrated with respect to system 10 of FIGS. 1-3, method 230 is not limited to being performed by examples of system 10, and may be performed, in whole or in part, by any of the example devices and/or systems described in this disclosure, such as system 10 of FIGS. 1-4, IMDS 52, 54, and/or 56 of FIGS. 5-8, system 120 of FIG. 9, and the equivalents thereof. Method 230 includes a method for receiving cardiac signals associated with cardiac activity of patient 12 as sensed using electrodes 16 of system 10 and performing an analysis of the sensed cardiac signals to determine if any of the sensed cardiac signals include a noise signal.

Method 230 includes computing apparatus 20 of system 10 receiving a cardiac signal sensed by electrodes 16 (block 232). Receiving a cardiac signal may include receiving a single cardiac signal sensed by a particular pair of electrodes 16, and/or receiving a plurality of cardiac signals that may be sensed by a plurality of electrodes 16. In some examples, receiving the cardiac signal or signals includes receiving the cardiac signal(s) in real-time as the cardiac signal or signals is/are being sensed by electrodes 16. In other examples, receiving the cardiac signal(s) may include retrieving data corresponding to one or more sensed cardiac signals, such as data stored in a memory, and performing the analysis provided by method 230 on the retrieved data at some time after the cardiac signal(s) has been sensed and the data stored into the memory.

Method 230 includes computing apparatus 20 setting a first detection window including a portion of a received cardiac signal (block 234). Setting the first detection window may include setting the position of the first detection window relative in time to the received cardiac signal based on a selected sample time. The sample time may be one of a plurality of sample times taken at some repetitive time interval relative to the time over which the cardiac signal is sensed. In some examples, the sample time is dependent on detection of a particular event, such as detection of a R-wave, in the cardiac signal being sensed. Once a sample time is selected, setting the first detection window may include having the first detection window superimposed over a waveform representative of the sensed cardiac signal and extending for a time span having a pre-defined width that extends from the sample time over the pre-defined period for a span of time prior to the sampling time. In some examples, the width of the time span of the first detection window is in a range of 0.5 to 5 seconds.

Once the first detection window is set, method 230 includes determining a baseline amplitude value for the portion of the cardiac signal that falls within the first detection window (block 236). In various examples, determining the baseline amplitude value of the cardiac signal that falls within the first detection window includes sampling the voltage values of the portion of the cardiac signal that falls within the first detection window at some sampling rate, and providing a baseline amplitude value based on the sampled voltage values. The baseline amplitude value may be an average value of the sampled voltage values from the portion of the cardiac signal that falls within the first detection window. The baseline amplitude value may be a mean value of the sampled voltage values from the portion of the cardiac signal that falls within the first detection window.

Method 230 further includes computing apparatus 20 setting a second detection window (block 238). Setting the second detection window may include setting the second detection window so that the second detection window is superimposed over the waveform representative of the received cardiac signal, the second detection window have a width extending over a time span that starts at the sample time used for setting the corresponding first detection window and extending for a pre-determined time span following the sample time. The width in time for the time span included within the second detection window is not limited to any particular value for the time span, and in some examples, is in a range of 0.5 to 5 seconds. In some examples, the width of the time span for the second detection window is the same as the width of the time span set for the first detection window, and in other examples the width of the time span for the second detection window is different from the width of the time span set for the first detection window.

After setting the second detection window, method 230 includes computing apparatus 20 determining an area-under-the curve value for a portion of the cardiac signal that falls within the second detection window (block 240). Determining an area-under-the-curve value may include calculating an area underneath the portion of the cardiac signal that falls within the second detection window and that is also above the baseline amplitude value that was calculated based on the voltage values for the portion of the cardiac signal that fell within the corresponding first detection window. Calculation of the value for the area-under-the-curve is not limited to any particular technique for making the calculation and may include any technique for calculating the area under a portion of a waveform as described herein, and/or any techniques as would be understood by one of ordinary skill in the art for calculating an area under a curve.

Following calculation of an area-under-the-curve value associated with the second detection windows, method 230 includes computing apparatus 20 determining that the cardiac signal includes a noise signal in response to a determination that the area-under-the-curve value exceeds a noise signal threshold value. In various examples, the noise signal threshold value is a programmable value that may be stored within a memory of computing apparatus 20. If method 230 includes a detection of a noise signal in the analyzed cardiac signal, computing apparatus 20 in some examples generates an alarm output signal that may be output to a device, such as a graphical display device, to provide an indication of the detection of the noise signal. In various examples, the alarm output signal may include a graphical display of the corresponding waveform including the portion of the waveform that includes the noise signal and may include graphical indications representative of the first and second detection windows superimposed over the graphical depiction of the waveform. Additional information related to the detection of a noise signal in the analyzed cardiac signal may include coloration, or some other form of a graphical depiction, such as a flashing graphical indication representative of the graphical portion of the displayed waveform comprising the detected noise signal.

The graphical indication of the detection of a noise signal may include display of textual information, such as display of numerical information associated with a calculated value for the amplitude and/or the area-under-the-curve value of the voltage spike determined to be the detected noise signal. In addition, upon a detection of a noise signal at block 242, method 230 may include computing apparatus 20, or other devices such as the implanted medical devices described in this disclosure and associated with the same patient as the sensed cardiac signals, to reject the signal or signal being sensed by the sensing channels (e.g., the particular electrodes 16) providing the sensed cardiac signal where the noise signal occurred. In some examples of method 230, generation of the alarm output signal may be further processed by one or more devices to reconfigure the electrodes that may be used, either currently or potentially, to provide a stimulation therapy to the patient being monitored using the received cardiac signals so that the electrodes proving the cardiac signal where the noise signal was detected may not be used for the application of therapy, either on a temporary or a permanent basis.

Detection of a noise signal using method 230 in an analyzed cardiac signal or signal may include rejection of the portion or portions of the cardiac signal(s) that include the detected low frequency noise signal or signals. Rejection of a signal or signals that are determined to include a low frequency noise signal may prevent miscounting of R-wave in the monitored signals, may prevent the false-positive indication of a cardiac event, such as asystole, occurring for a monitored patient. Detection of the noise signal or signals may also allow the system 10 to be reconfigured to stop using an affected lead and/or electrode pairs providing the cardiac signal that includes the detected noise signal for the further monitoring of the patient. Detection of the noise signal or signals and may also allow the system 10 to be reconfigured to stop using or to not use an affected lead and/or electrode pair providing the cardiac signal that included the detected noise signal for the purpose of providing therapy, such as electrical stimulation therapy, to the patient.

Method 230 may include repeatedly performing the processes of receiving the cardiac signal, setting the first detection window, determining the baseline amplitude value associated with the first detection window, setting the second detection window, determining the area-under-the-curve for the portion of the cardiac signal falling within the second detection window, and comparing the calculated area-under-the-curve to a noise signal threshold value to determine if the portion of the cardiac signal being analyzed includes a noise signal using a moving or sliding set of detection windows as described above. Method 230 may be repeated on a continuous basis by repeatedly receiving more portions of the sensed cardiac at block 232 and performing the method 230 on the newly received portions of the cardiac signal as illustratively represented by arrow 244 extending from block 242 to block 232 in FIG. 12. Each iteration of method 230 may be performed based on a different sample time and an associated first and second detection windows that are set relative to the received portions of a cardiac signal that may be received for example on a continuing basis over some period of time. The number of times the method 230 may be performed on portions of a cardiac signal is not limited to any particular number of times, and for example may be repeated over a period of several minutes in examples where the monitoring of the cardiac signals is being performed as part of a clinical visit or doctor's appointment. In some examples, method 230 may be performed over an extended period of time, such as hours or days, for example when performed by a device worn by the patient such as electrode apparatus 14, and/or when being performed for example by an implanted device, such as the IMDs described herein, that may have been implanted in the patient being monitored.

Figure 13:
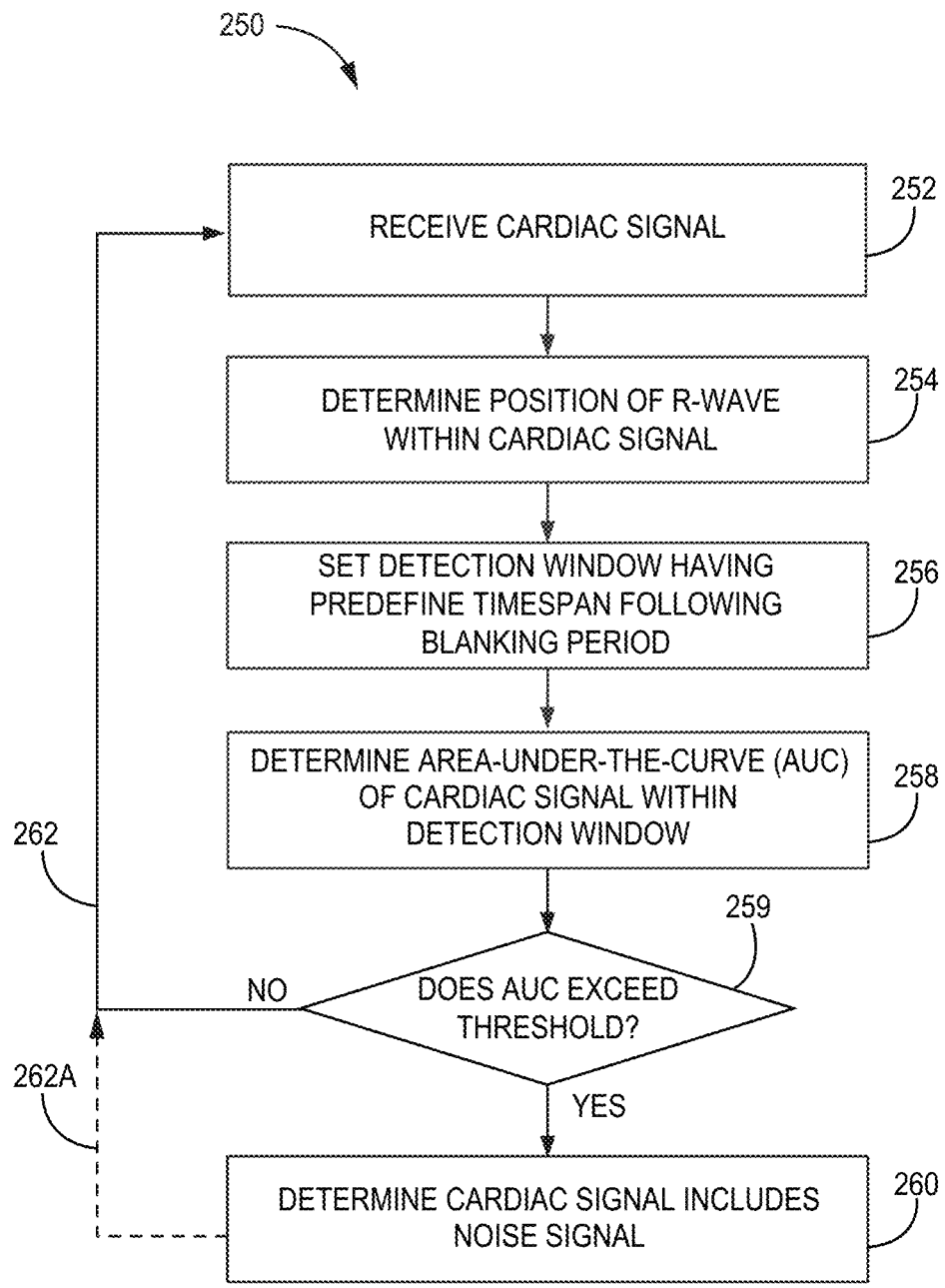
FIG. 13 illustrates a flowchart of another method according to various examples described in this disclosure.

FIG. 13 illustrates a flowchart illustrating another method 250 in according to various examples described in this disclosure. Although method 250 is described with respect to the devices and systems illustrated with respect to system 10 of FIGS. 1-3, method 250 is not limited to being performed by examples of system 10, and may be performed, in whole or in part, by any of the example devices and/or systems described in this disclosure, such as system 10 of FIGS. 1-4, IMDS 52, 54, and/or 56 of FIGS. 5-8, system 120 of FIG. 9, and the equivalents thereof. Method 250 includes a method for receiving a cardiac signal or multiple cardiac signals associated with cardiac activity of patient 12 as sensed using electrodes 16 of system 10 and performing an analysis of the sensed cardiac signal or signals to determine if any of the sensed cardiac signals include a noise signal.

Method 250 includes computing apparatus 20 of system 10 receiving a cardiac signal sensed by electrodes 16 (block 252). Receiving a cardiac signal may include receiving a single cardiac signal sensed by a particular pair of electrodes 16, and/or receiving a plurality of cardiac signals that may be sensed by a plurality of electrodes 16. In some examples, receiving the cardiac signal or signals includes receiving the cardiac signal(s) in real-time as the cardiac signal or signals is/are being sensed by electrodes 16. In other examples, receiving the cardiac signal(s) may include retrieving data corresponding to one or more sensed cardiac signals, such as data stored in a memory, and performing the analysis provided by method 250 on the retrieved data at some time after the cardiac signal(s) has been sensed and the data stored into the memory.

Method 250 includes computing apparatus 20 determining the position of a R-wave within the cardiac signal (block 254). Detection of an R-wave within the cardiac signal is not limited to any particular technique for detection of R-waves and may include for example detection of an R-wave based on the voltage value for the received cardiac signal exceeding a R-wave threshold value. Once the R-wave is detected within the received cardiac signal, determining the position of the detected R-wave may include setting a sample time at the position (relative to time) of the cardiac signal where the R-wave occurred.

Method 250 includes computing apparatus 20 setting a detection window having a pre-defined time span and a starting time following a blanking period after the sample time (block 256). Setting the detection window may include setting a blanking period starting at the sample time and having a width that extends from the sample time to a pre-defined time span following the sample time. The width of the blanking period is not limited to any particular time span, and in some examples may be in a range of 0.01 to 0.5 seconds. Method 250 further includes setting the position of the detection window so that the detection window starts at the time the blanking period ends and extends over a width in time having a predefined time span following the blanking period. The width of the detection widow is not limited to any particular width, and in some examples, may be in a range of 0.5 to 5 seconds.

Once the detection window is set, method 250 includes computing apparatus 20 determining an area-under-the curve value for a portion of the cardiac signal that falls within the detection window (block 258). Determining an area-under-the-curve value may include calculating an area underneath the portion of the cardiac signal that falls within the detection window and that is also above a baseline amplitude value. The baseline amplitude value in some examples may be a programmable value set by a user, such as a physician. The baseline amplitude value in some examples is based on a voltage values sampled from the cardiac signal during blanking period. Calculation of the value for the area-under-the-curve is not limited to any particular technique for making the calculation and may include any technique for calculating the area under a portion of a waveform as described herein, and/or any techniques as would be understood by one of ordinary skill in the art for calculating an area under a curve.

Following calculation of an area-under-the-curve value associated with the detection window, method 250 includes computing apparatus 20 determining that the cardiac signal includes a noise signal in response to a determination of the area-under-the-curve value exceeds a noise signal threshold value. In various examples, the noise signal threshold value is a programmable value that may be set by a user, such as a physician, and may be stored within computing apparatus 20. If method 250 results in a detection of a noise signal in the analyzed cardiac signal, computing apparatus 20 in some examples generates an alarm output signal that may be output to a device, such as a graphical display device, to provide an indication of the detection of the noise signal. Output of an alarm output signal may include any combination of the further processes as described above with respect to method 230 and as otherwise described throughout this disclosure associated with the detection of a noise signal in a sensed cardiac signal.

Detection of a noise signal using method 250 in an analyzed cardiac signal or signal may include rejection of the portion or portions of the cardiac signal(s) that include the detected low frequency noise signal or signals. Rejection of a signal or signals that are determined to include a low frequency noise signal may prevent miscounting of R-wave in the monitored signals, may prevent the false-positive indication of a cardiac event, such as asystole, occurring for a monitored patient. Detection of the noise signal or signals may also allow the system 10 to be reconfigured to stop using an affected lead and/or electrode pairs providing the cardiac signal that includes the detected noise signal for the further monitoring of the patient. Detection of the noise signal or signals and may also allow the system 10 to be reconfigured to stop using or to not use an affected lead and/or electrode pair providing the cardiac signal that included the detected noise signal for the purpose of providing therapy, such as electrical stimulation therapy, to the patient.

Method 250 may include repeatedly performing the processes of receiving the cardiac signal, determining the position of a R-wave within the cardiac signal, setting a detection window having a pre-defined timespan following a blanking period, determining the area-under-the-curve for the portion of the cardiac signal falling within the detection window, and comparing the calculated area-under-the-curve to a noise signal threshold value to determine if the portion of the cardiac signal being analyzed includes a noise signal using a moving or sliding detection window. Method 250 may be repeated on a continuous basis by repeatedly receiving more portions of the sensed cardiac signal at block 252 and performing the method 250 on the newly received portions of the cardiac signal as illustratively represented by arrow 262 extending from block 260 to block 252 in FIG. 13. Each iteration of method 250 may be performed based on a different sample time and an associated different detection window that are set relative to the received portions of a cardiac signal that may be received for example on a continuing basis over some period of time. Each sample time may be set based on a detection of a R-wave, or for example based on the detection of some "N" number of sensed R-waves, as previously described above. The number of times the method 250 may be performed on portions of a cardiac signal is not limited to any particular number of times, and for example may be repeated over a period of several minutes in examples where the monitoring of the cardiac signals is being performed as part of a clinical visit or doctor's appointment. In some examples, method 250 may be performed over an extended period of time, such as hours or days, for example when performed by a device worn by the patient such as electrode apparatus 14, and/or when being performed for example by an implanted device, such as the IMDs described herein, that may have been implanted in the patient being monitored.

Figure 14:
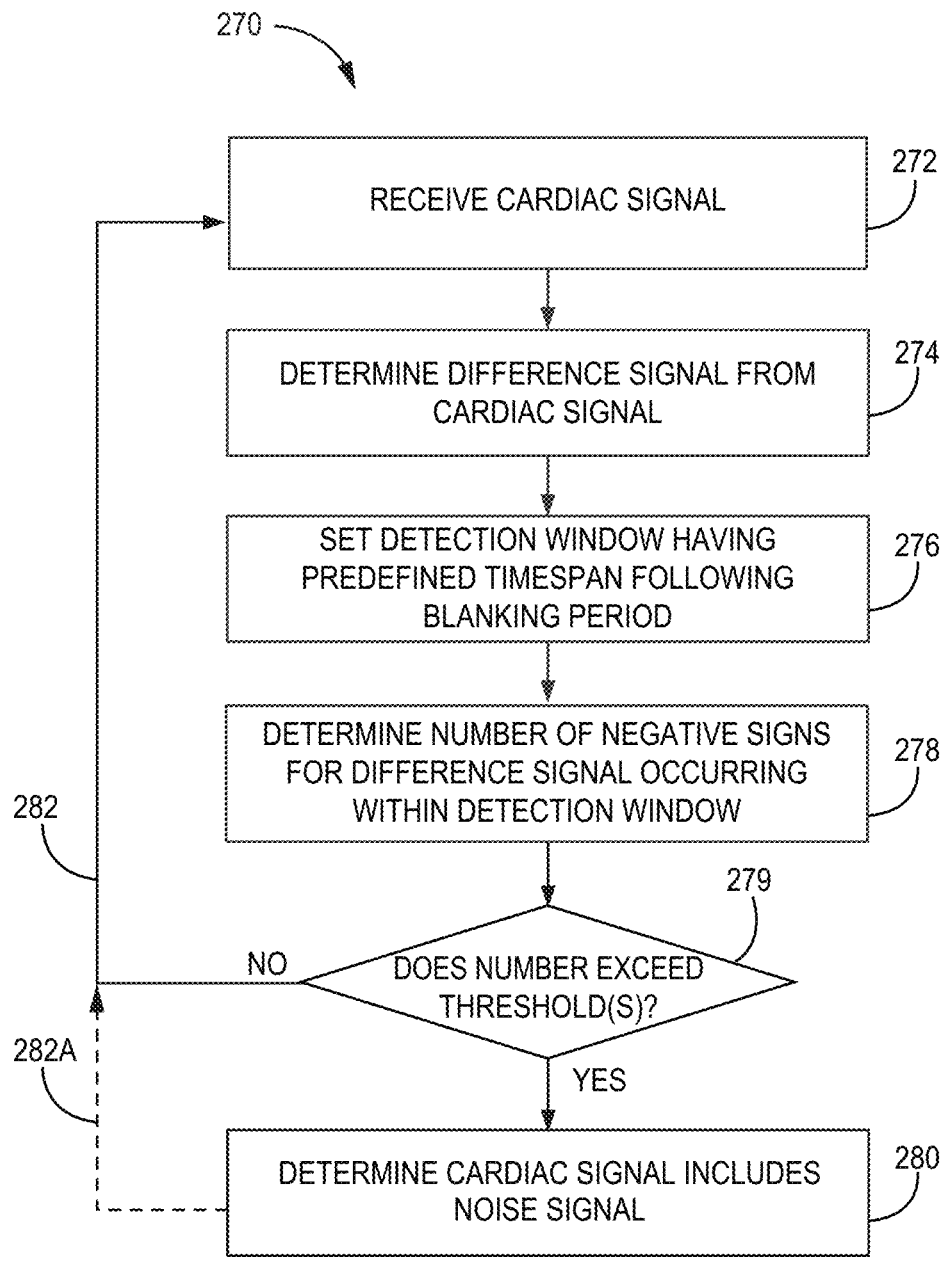
FIG. 14 illustrates a flowchart of another method according to various examples described in this disclosure.

FIG. 14 illustrates a flowchart illustrating a method 270 according to various examples described in this disclosure. Although method 270 is described with respect to the devices and systems illustrated with respect to system 10 of FIGS. 1-3, method 270 is not limited to being performed by examples of system 10, and may be performed, in whole or in part, by any of the example devices and/or systems described in this disclosure, such as system 10 of FIGS. 1-4, IMDS 52, 54, and/or 56 of FIGS. 5-8, system 120 of FIG. 9, and the equivalents thereof. Method 230 includes a method for receiving cardiac signals associated with cardiac activity of patient 12 as sensed using electrodes 16 of system 10 and performing an analysis of the sensed cardiac signals to determine if any of the sensed cardiac signals include a noise signal.

Method 270 includes computing apparatus 20 of system 10 receiving a cardiac signal sensed by electrodes 16 (block 272). Receiving a cardiac signal may include receiving a single cardiac signal sensed by a particular pair of electrodes 16, and/or receiving a plurality of cardiac signals that may be sensed by a plurality of electrodes 16. In some examples, receiving the cardiac signal or signals includes receiving the cardiac signal(s) in real-time as the cardiac signal or signals is/are being sensed by electrodes 16. In other examples, receiving the cardiac signal(s) may include retrieving data corresponding to one or more sensed cardiac signals, such as data stored in a memory, and performing the analysis provided by method 270 on the retrieved data at some time after the cardiac signal(s) has been sensed and the data stored into the memory.

Method 270 includes computing apparatus 20 determining a difference signal based on the received cardiac signal (block 274). The difference signal may comprise a set of values determined by calculating a different between the value of the cardiac signal at time "Y(n)," wherein time "Y(n)" represents a sample time where a voltage value for the cardiac signal is determined, and the voltage value of the cardiac signal at time "Y(n−1)," wherein Y(n−1) is the time value at some predefined time prior to the time Y(n).

After determining the values for the difference signal, method 270 includes computing apparatus 20 setting a detection window having a predefined time span following a blanking period (block 276). As part of setting the detection window, method 270 may include computing apparatus 20 detecting the position of a R-wave within the difference signal representative of the cardiac signal being analyzed. Detection of a R-wave within the cardiac signal is not limited to any particular technique for detection of R-waves and may include for example detection of an R-wave based on the voltage value for the received cardiac signal exceeding a R-wave threshold value. One the R-wave is detected within the received cardiac signal, determining the position of the detected R-wave may include setting a sample time at the position (relative to time) of the cardiac signal where the R-wave occurred. Based on the setting of the sample time, method 250 further includes computing apparatus 20 setting a detection window having a pre-defined time span and a starting time following a blanking period after the sample time. Setting the detection window may include setting a blanking period starting at the sample time and having a width that extends from the sample time to a pre-defined time span following the sample time. The width of the blanking period is not limited to any particular time span, and in some examples may be in a range of 0.01 to 0.5 seconds. Method 270 further includes computing apparatus 20 setting the position of the detection window so that the detection window is superimposed over the difference signal, starts at the time the blanking period ends, and extends over a width having a predefined time span following the blanking period. The width of the detection widow is not limited to any particular width, and in some examples may be in a range of 0.5 to 5 seconds.

Once the detection window is set, method 270 includes computing apparatus 20 determining a number of negative signs for the difference signal occurring within the detection window (block 278). As described above, a negative sign within the difference signal may exist in the difference signal where the value of the difference signal is negative, e.g., less than zero, at some predefined sample time interval.

Method 270 includes computing apparatus 20 determining that the difference signal, and thus the corresponding cardiac signal, includes a noise signal in response to a determination that the number of negative signs within the detection window exceeds one or more threshold values (block 280). Method 270 includes having computing apparatus 20 compare the determined number of negative signs for the difference signal falling within the detection window, or for example a percentage or a ratio of the sample times within the detection window that resulted in a negative value for the difference signal to one or more threshold values. The threshold values may be programmable values that are programmed into computing apparatus 20, for example by a user such as a physician, and stored in a memory within computing apparatus 20. As described above, in alternative examples a quantification value associated with the portion of the waveform included within the detection window may be based on a particular criterion or a set of criteria other than the number of negative signs falling within the detection window. The quantification value may be comparted at block 279 to the one or more threshold values to determine whether the cardiac signal includes a noise signal.

In some examples, the analyzed portion of the difference signal is determined to include a noise signal if the percentage of negative signs (or other criterion/criteria used to calculate a quantification value) sampled at the sample times falling with the detection window exceeds a maximum percentage threshold value, or if the percentage of negative signs (or other criterion/criteria used to calculate a quantification value) sampled at the sample times falling with the detection window is less than a minimum percentage threshold value. In other words, if the percentage of negative signs sampled at the sample times falling within the detection window does not fall within a range that is above the minimum threshold value and below the maximum threshold value, the portion of the signal occurring within the detection window is considered to be a noise signal. If method 270 results in a detection of a noise signal in the analyzed cardiac signal, computing apparatus 20 in some examples generates an alarm output signal that may be output to a device, such as a graphical display device, to provide an indication of the detection of the noise signal. Output of an alarm output signal may include any combination of the further processes as described above with respect to method 230 and as otherwise described throughout this disclosure associated with the detection of a noise signal in a sensed cardiac signal.

Detection of a noise signal using method 270 in an analyzed cardiac signal or signal may include rejection of the portion or portions of the cardiac signal(s) that include the detected low frequency noise signal or signals. Rejection of a signal or signals that are determined to include a low frequency noise signal may prevent miscounting of R-wave in the monitored signals, may prevent the false-positive indication of a cardiac event, such as asystole, occurring for a monitored patient. Detection of the noise signal or signals may also allow the system 10 to be reconfigured to stop using an affected lead and/or electrode pairs providing the cardiac signal that includes the detected noise signal for the further monitoring of the patient. Detection of the noise signal or signals and may also allow the system 10 to be reconfigured to stop using or to not use an affected lead and/or electrode pair providing the cardiac signal that included the detected noise signal for the purpose of providing therapy, such as electrical stimulation therapy, to the patient.

Method 270 may include repeatedly performing the processes of receiving the cardiac signal, determining the difference signal from the cardiac signal, setting a detection window having a pre-defined timespan following a blanking period, determining the number of negative signs (or calculation of a quantification value based on a particular criterion or set of criteria) for the difference signal occurring within the detection window, and comparing the number of negative signs (or a percentage or ratio of negative signs, or the calculated quantification value) to one or more threshold values to determine if the portion of the difference signal, and thus the corresponding portion of the cardiac signal being analyzed includes a noise signal using a moving or sliding detection window as described above. Method 270 may be repeated on a continuous basis by repeatedly receiving more portions of the sensed cardiac at block 272 and performing the method 270 on the newly received portions of the cardiac signal as illustratively represented by arrow 282 extending from block 280 to block 272 in FIG. 14. Each iteration of method 270 may be performed based on a different sample time and an associated different detection window that are set relative to the received portions of a cardiac signal that may be received for example on a continuing basis over some period of time. Each sample time may be set based on a detection of a R-wave, or for example based on the detection of some "N" number of sensed R-waves, as previously described above. The number of times the method 270 may be performed on portions of a cardiac signal is not limited to any particular number of times, and for example may be repeated over a period of several minutes in examples where the monitoring of the cardiac signals is being performed as part of a clinical visit or doctor's appointment. In some examples, method 270 may be performed over an extended period of time, such as hours or days, for example when performed by a device worn by the patient such as electrode apparatus 14, and/or when being performed for example by an implanted device, such as the IMDs described herein, that may have been implanted in the patient being monitored.

The techniques of this disclosure may be implemented in a wide variety of computing devices, medical devices, or any combination thereof. Any of the described units, modules or components may be implemented together or separately as discrete but interoperable logic devices. Depiction of different features as modules, units, circuits, or circuitry, is intended to highlight different functional aspects and does not necessarily imply that such modules, units, circuits, or circuitry must be realized by separate hardware or software components. Rather, functionality associated with one or more modules, units, circuits, or circuitry may be performed by separate hardware or software components or integrated within common or separate hardware or software components.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random-access memory (RAM), read-only memory (ROM), non-volatile random-access memory (NVRAM), electrically erasable programmable read-only memory (EEPROM), FLASH memory, magnetic media, optical media, or the like that is tangible. The computer-readable storage media may be referred to as non-transitory. A server, client computing device, or any other computing device may also contain a more portable removable memory type to enable easy data transfer or offline data analysis. The instructions may be executed to support one or more aspects of the functionality described in this disclosure.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various aspects of this disclosure have been described. These and other aspects are within the scope of the following claims.

What is claimed is:

1. A medical device system comprising:
a plurality of electrodes configured to sense electrical activity of a heart of a patient; and
processing circuitry configured to:
receive a cardiac signal generated in response to sensing the electrical activity of the heart of the patient using the plurality of electrodes;
determine a difference signal from the cardiac signal, the difference signal comprising a set of amplitude values determined by calculating a difference between an amplitude value of the cardiac signal at a first time and an amplitude value of the cardiac signal at a second time, wherein the second time is a predefined time prior to the first time;
set a first detection window having a first time period extending for a predefined amount of time and a second detection window having a second time period starting at the expiration of the first detection window and extending for a predefined amount of time following the expiration of the first detection window;
determine a quantification value for the difference signal occurring within the second detection window;
compare the quantification value to one or more threshold values;
determine that the cardiac signal includes a noise signal in response to a determination that the quantification value exceeds the one or more threshold values, and
in response to the determination that the cardiac signal includes the noise signal, output, for display to a user, an indication that the cardiac signal includes the noise signal.

2. The medical device system of claim 1, wherein the plurality of electrodes are included in an electrode apparatus configured to be worn by the patient and arranged so that the plurality of electrodes are placed in contact with a skin surface of the patient when the electrode apparatus is worn by the patient.

3. The medical device system of claim 1, wherein the plurality of electrodes are electrically coupled to an implantable medical device (IMD) that is implanted within the patient.

4. The medical device system of claim 1,
wherein the first detection window comprises the first time period, the first time period having a length in a range of 0.01 to 5 seconds, and
wherein the second detection window comprises the second time period, the second time period having a length in a range of 0.5 to 5 seconds.

5. The medical device system of claim 1,
wherein the medical device system further comprises a medical device, and
wherein the processing circuitry is further configured to control, based on the determination that the cardiac signal includes the noise signal, the medical device to reconfigure one or more sensing channels used in sensing the electrical activity of the heart of the patient to exclude using one or more of the plurality of electrodes utilized in the one or more sensing channels.

6. The medical device system of claim 1,
wherein the medical device system further comprises a medical device, and
wherein the processing circuitry is further configured to control, based on the determination that the cardiac signal includes the noise signal, the medical device to reconfigure one or more therapy parameters used in defining delivery of stimulation therapy to the patient to exclude using one or more of the plurality of electrodes utilized in delivery of the stimulation therapy.

7. The medical device system of claim 1,
wherein to receive the cardiac signal generated in response to sensing the electrical activity of the heart of the patient, the processing circuitry is configured to receive a plurality of cardiac signals generated in response to sensing the electrical activity of the heart of the patient, and
for each of the plurality of cardiac signals, the processing circuitry further configured to:
determine a difference signal from the cardiac signal, the difference signal comprising a set of amplitude values determined by calculating a difference between an amplitude value of the cardiac signal at a first time and an amplitude value of the cardiac signal at a second time, wherein the second time is a predefined time prior to the first time;
set a first detection window having a first time period extending for a predefined amount of time and a second detection window having a second time period starting at the expiration of the first detection window and extending for a predefined amount of time following the expiration of the first detection window;
determine a quantification value for the difference signal occurring within the second detection window;
compare the quantification value to one or more threshold values; and
determine that the cardiac signal includes a noise signal in response to a determination that the quantification value exceeds one or more threshold values.

8. A method performed by an implantable medical device comprising a housing and processing circuitry within the housing, the processing circuitry coupled to one or more one or more electrodes, the method comprising:
receiving, by the processing circuitry of the implantable medical device, a cardiac signal generated in response to sensing electrical activity of a heart of a patient via the one or more electrodes;
determining, by the processing circuitry of the implantable medical device, a difference signal from the cardiac signal, the difference signal comprising a set of amplitude values determined by calculating a difference between an amplitude value of the cardiac signal at a first time and an amplitude value of the cardiac signal at a second time, wherein the second time is a predefined time prior to the first time;
setting, by the processing circuitry of the implantable medical device, a detection window having a time period extending for a predefined amount of time;
determining, by the processing circuitry of the implantable medical device, a quantification value corresponding to at least one criterion associated with values for the difference signal occurring within the detection window;
comparing, by the processing circuitry of the implantable medical device, the quantification value to one or more threshold values;
determining, by the processing circuitry of the implantable medical device, that the cardiac signal includes a noise signal based on the comparison of the quantification value to the one or more threshold values; and
in response to the determination that the cardiac signal includes the noise signal, outputting, by the processing circuitry of the implantable medical device and for display to a user, an indication that the cardiac signal includes the noise signal.

9. The method of claim 8, wherein the at least one criterion comprises a number, a percentage, or a ratio of negative signs in the difference signal occurring within the detection window.

10. The method of claim 8, wherein determining that the quantification value exceeds one or more threshold values comprises determining that the quantification value is less than a minimum threshold value or greater than a maximum threshold value.

11. The method of claim 8,
wherein the detection window having the time period extending for the predefined amount of time comprises a detection window having a time period extending for a predefined amount of time following a sample time, and
wherein the sample time is set within the difference signal relative to time based on the detection of a R-wave occurring within the cardiac signal.

12. The method of claim 8, further comprising controlling, by the processing circuitry of the implantable medical device and based on the determination that the cardiac signal includes the noise signal, a medical device to reconfigure one or more sensing channels used in sensing the electrical activity of the heart of the patient to exclude using one or more electrodes utilized in the one or more sensing channels.

13. The method of claim 8, wherein receiving the cardiac signal generated in response to electrical activity of the heart of the patient comprises receiving a plurality of cardiac signals generated in response to the electrical activity of the heart of the patient, and
for each of the plurality of cardiac signals:
determining, by the processing circuitry of the implantable medical device, a difference signal from the cardiac signal, the difference signal comprising a set of amplitude values determined by calculating a difference between the amplitude value of the cardiac signal at a first time and the amplitude value of the cardiac signal at a second time, wherein the second time is a predefined time prior to the first time;

setting, by the processing circuitry of the implantable medical device, a first detection window having a first time period extending for a predefined amount of time and a second detection window having a second time period starting at the expiration of the first detection window and extending for a predefined amount of time following the expiration of the first detection window;

determining, by the processing circuitry of the implantable medical device, a quantification value for the difference signal occurring within the second detection window;

comparing, by the processing circuitry of the implantable medical device, the quantification value to one or more threshold values; and determining, by the processing circuitry of the implantable medical device, that the cardiac signal includes a noise signal in response to a determination that the quantification value exceeds one or more threshold values.

14. The method of claim 8, wherein determining the difference signal from the cardiac signal, the difference signal comprising the set of amplitude values determined by calculating the difference between the amplitude value of the cardiac signal at the first time and the amplitude value of the cardiac signal at the second time comprises:

determining the difference signal from the cardiac signal, the difference signal comprising a set of voltage values determined by calculating a difference between a voltage value of the cardiac signal at the first time and a voltage value of the cardiac signal at the second time.

15. The method of claim 8, wherein determining the difference signal from the cardiac signal, the difference signal comprising the set of amplitude values determined by calculating the difference between the amplitude value of the cardiac signal at the first time and the amplitude value of the cardiac signal at the second time comprises:

determining the difference signal from the cardiac signal, the difference signal comprising a set of current values determined by calculating a difference between a current value of the cardiac signal at the first time and a current value of the cardiac signal at the second time.

16. A method performed by processing circuitry of an implantable medical system comprising a plurality of electrodes, the method comprising:

receiving, by the processing circuitry of the medical device system, a cardiac signal generated in response to sensing electrical activity of a heart of a patient via the plurality of electrodes;

determining, by the processing circuitry of the medical device system, a difference signal from the cardiac signal, the difference signal comprising a set of amplitude values determined by calculating a difference between an amplitude value of the cardiac signal at a first time and an amplitude value of the cardiac signal at a second time, wherein the second time is a predefined time prior to the first time;

setting, by the processing circuitry of the medical device system, a first detection window having a first time period extending for a predefined amount of time and a second detection window having a second time period starting at the expiration of the first detection window and extending for a predefined amount of time following the expiration of the first detection window;

determining, by the processing circuitry of the medical device system, a quantification value for the difference signal occurring within the second detection window;

comparing, by the processing circuitry of the medical device system, the quantification value to one or more threshold values;

determining, by the processing circuitry of the medical device system, that the cardiac signal includes a noise signal in response to a determination that the quantification value exceeds the one or more threshold values, and in response to the determination that the cardiac signal includes the noise signal, outputting, by the processing circuitry of the medical device system and for display to a user, an indication that the cardiac signal includes the noise signal.

17. The method of claim 16,
wherein the first detection window comprises the first time period, the first time period having a length in a range of 0.01 to 5 seconds, and
wherein the second detection window comprises the second time period, the second time period having a length in a range of 0.5 to 5 seconds.

18. The method of claim 16, further comprising controlling, by the processing circuitry of the medical device system and based on the determination that the cardiac signal includes the noise signal, a medical device to reconfigure one or more sensing channels used in sensing the electrical activity of the heart of the patient to exclude using one or more of the plurality of electrodes utilized in the one or more sensing channels.

19. The method of claim 16, further comprising controlling, by the processing circuitry of the medical device system and based on the determination that the cardiac signal includes the noise signal, the medical device to reconfigure one or more therapy parameters used in defining delivery of stimulation therapy to the patient to exclude using one or more of the plurality of electrodes utilized in delivery of the stimulation therapy.

20. The method of claim 16,
wherein receiving the cardiac signal generated in response to sensing the electrical activity of the heart of the patient comprises receiving a plurality of cardiac signals generated in response to sensing the electrical activity of the heart of the patient, and
wherein the method further comprises:
for each of the plurality of cardiac signals:
determining, by the processing circuitry of the medical device system, a difference signal from the cardiac signal, the difference signal comprising a set of amplitude values determined by calculating a difference between an amplitude value of the cardiac signal at a first time and an amplitude value of the cardiac signal at a second time, wherein the second time is a predefined time prior to the first time;
setting, by the processing circuitry of the medical device system, a first detection window having a first time period extending for a predefined amount of time and a second detection window having a second time period starting at the expiration of the first detection window and extending for a predefined amount of time following the expiration of the first detection window;

determining, by the processing circuitry of the medical device system, a quantification value for the difference signal occurring within the second detection window;

comparing, by the processing circuitry of the medical device system, the quantification value to one or more threshold values; and determining, by the processing circuitry of the medical device system, that the cardiac signal includes a noise signal in response to a determination that the quantification value exceeds one or more threshold values.

* * * * *